(12) United States Patent
Xu

(10) Patent No.: US 11,890,304 B2
(45) Date of Patent: *Feb. 6, 2024

(54) PANCREATIC ENDOCRINE CELLS AND METHODS THEREOF

(71) Applicant: Janssen Biotech, Inc., Horsham, PA (US)

(72) Inventor: Jean Xu, Raritan, NJ (US)

(73) Assignee: Janssen Biotech, Inc., Horsham, PA (US)

(*) Notice: Subject to any disclaimer, the term of this patent is extended or adjusted under 35 U.S.C. 154(b) by 901 days.

This patent is subject to a terminal disclaimer.

(21) Appl. No.: 16/582,279

(22) Filed: Sep. 25, 2019

(65) Prior Publication Data

US 2020/0030383 A1   Jan. 30, 2020

Related U.S. Application Data

(60) Continuation of application No. 15/660,885, filed on Jul. 26, 2017, now Pat. No. 10,456,424, which is a continuation of application No. 14/751,416, filed on Jun. 26, 2015, now Pat. No. 9,744,195, which is a division of application No. 12/183,656, filed on Jul. 31, 2008, now Pat. No. 9,096,832.

(60) Provisional application No. 60/953,178, filed on Jul. 31, 2007.

(51) Int. Cl.
   *A61K 35/39*   (2015.01)
   *C12N 5/071*   (2010.01)

(52) U.S. Cl.
   CPC ............ *A61K 35/39* (2013.01); *C12N 5/0676* (2013.01); *C12N 2500/34* (2013.01); *C12N 2501/115* (2013.01); *C12N 2501/12* (2013.01); *C12N 2501/155* (2013.01); *C12N 2501/16* (2013.01); *C12N 2501/21* (2013.01); *C12N 2501/23* (2013.01); *C12N 2501/335* (2013.01); *C12N 2501/385* (2013.01); *C12N 2501/40* (2013.01); *C12N 2501/415* (2013.01); *C12N 2501/42* (2013.01); *C12N 2501/70* (2013.01); *C12N 2501/999* (2013.01); *C12N 2506/02* (2013.01); *C12N 2533/90* (2013.01)

(58) Field of Classification Search
   CPC .................................................... A61K 35/39
   See application file for complete search history.

(56) References Cited

U.S. PATENT DOCUMENTS

| | | | |
|---|---|---|---|
| 8,859,286 B2 | 10/2014 | Agulnick | |
| 9,096,832 B2 * | 8/2015 | Xu | A61P 3/10 |
| 10,456,424 B2 * | 10/2019 | Xu | A61P 3/10 |
| 2003/0138948 A1 | 7/2003 | Fisk et al. | |
| 2004/0121460 A1 | 6/2004 | Lumelsky et al. | |
| 2005/0054102 A1 | 3/2005 | Wobus et al. | |
| 2005/0260749 A1 | 11/2005 | Odorico et al. | |
| 2005/0266554 A1 | 12/2005 | D'Amour et al. | |
| 2007/0027063 A1 | 2/2007 | Boss et al. | |
| 2007/0259421 A1 | 11/2007 | D'Amour et al. | |
| 2008/0267926 A1 | 10/2008 | Martinson et al. | |
| 2009/0263896 A1 | 10/2009 | Kelly et al. | |
| 2010/0015100 A1 | 1/2010 | Xu | |
| 2010/0112693 A1 | 5/2010 | Rezania et al. | |
| 2011/0151560 A1 | 6/2011 | Xu | |
| 2011/0281355 A1 | 11/2011 | Xu | |
| 2012/0052576 A1 | 3/2012 | Rezania | |
| 2014/0186953 A1 | 7/2014 | Rezania | |

FOREIGN PATENT DOCUMENTS

| | | | |
|---|---|---|---|
| CN | 1589330 A | 3/2005 | |
| EP | 2604685 B1 | 3/2017 | |
| WO | 2003029445 A1 | 4/2003 | |
| WO | 2004016747 A2 | 2/2004 | |
| WO | 2006036925 A1 | 4/2006 | |
| WO | 2006080952 A2 | 8/2006 | |
| WO | 2006083782 A2 | 8/2006 | |
| WO | 2006125438 A1 | 11/2006 | |
| WO | 2007002086 A2 | 1/2007 | |
| WO | WO-2007030469 A2 * | 3/2007 | ........... C12N 5/0606 |
| WO | 2007047509 A2 | 4/2007 | |
| WO | 2007051038 A2 | 5/2007 | |
| WO | 2006108361 A1 | 12/2007 | |
| WO | 2007103282 A3 | 2/2008 | |
| WO | 2009012428 A2 | 1/2009 | |
| WO | 2006105152 A3 | 6/2009 | |
| WO | 2009132083 A3 | 3/2010 | |
| WO | 2010051213 A1 | 5/2010 | |
| WO | 2011079017 A2 | 6/2011 | |
| WO | 2011081222 A1 | 7/2011 | |
| WO | 2011160066 A1 | 12/2011 | |
| WO | 2012030540 A2 | 3/2012 | |
| WO | 2013095953 A1 | 6/2013 | |
| WO | 2014105543 A1 | 7/2014 | |
| WO | 2014105546 A1 | 7/2014 | |
| WO | 2015002724 | 3/2015 | |

OTHER PUBLICATIONS

D'Amour et al. (epub Oct. 19, 2006, Nature Biotechnology, vol. 24(11), pp. 1392-1401) (Year: 2006).*
Shearman et al. (2000, Biochemistry, vol. 39, pp. 8698-8704) (Year: 2000).*
Zorn, et al., Vertebrate Endoderm Development and Organ Formation, Annual Review Cell Development Biology, Aug. 12, 2009, pp. 221-251, vol. 25.
Altirriba, et al. "The Role of Transmembrane Protein 27 (TMEM27) in islet physiology and its potential use as a beta cell mass biomarker." Diabetologia (2010): 53: 1406-1414.

(Continued)

*Primary Examiner* — Anoop K Singh
*Assistant Examiner* — David A Montanari
(74) *Attorney, Agent, or Firm* — Klarquist Sparkman, LLP

(57) ABSTRACT

The present invention provides methods to promote the differentiation of pluripotent stem cells. In particular, the present invention provides an improved method for the formation of pancreatic endoderm, pancreatic hormone expressing cells and pancreatic hormone secreting cells. The present invention also provides methods to promote the differentiation of pluripotent stem cells without the use of a feeder cell layer.

14 Claims, 60 Drawing Sheets

Specification includes a Sequence Listing.

(56) References Cited

OTHER PUBLICATIONS

Banerjee and Otonkoski, "A simple two-step protocol for the purification of human pancreatic beta cells." Diabetologia (2009) 52: 621-625.

Brewer, et al. "Optimized Survivial of Hippocampal Neurons in B27-Supplemented Neurobasal, a New Serum-free Medium Combination." Journal of Neuroscience Research 35: 567-576 (1993).

Cheng, et al. "Self-Renewing Endodermnal Progenitor Lines Generated From Human Pluripotent Stem Cells." Cell Stem Cell, vol. 10, No. 4, Apr. 1, 2012, pp. 371-384.

Cho, et al. "Inhibition of Activin/Nodal Signalling is necessary for pancreatic differentiatoin of human pluripotent stem cells." Diabetologia (2012) 55: 3284-3295.

Chung Young et al, "Human embryonic stem cell lines generated without embryo destruction", Cell Stem Cell, Cell Press, US, (Feb. 7, 2008), vol. 2, No. 2, doi:10.1016/J.STEM.2007.12.013, ISSN 1934-5909, pp. 113-117, XP002604696.

Cuny, et al. Structure-activity relationship study of bone morpogenetic protein (BMP) signlaing inhibitors. Bioorg Med Chem Lett. Aug. 1, 2008; 18(15): 4388-4392.

D'Amour K A et al, "Efficient differentiation of human embryonic stem cells to definitive endoderm", Nature Biotechnology, Nature Publishing Group, New York, NY, US, (Oct. 28, 2005), vol. 23, No. 12, ISSN 1087-0156, pp. 1534-1541, XP002385437.

D'Amour K A et al, "Production of pancreatic hormone-expressing endocrine cells from human embryonic stem cells", Nature Biotechnology, Nature Publishing Group, New York, NY, US, (Jan. 1, 2006), vol. 24, No. 11, ISSN 1087-0156, pp. 1392-1401, XP002423119.

Declaration of Maria Cristina Nostro, Ph.D. dated 7/22/201 in Toronto, Canada.

Fraker, et al. "Enhanced Oxygenation Promotes B-Cell Differentiation in Vitro." Stem Cells 2007; 25: 3155-3164.

Guillemain, et al., Glucose is Necessary for Embryonic Pancreatic Endocrine Cell Differentiation*, The Journal of Biological Chemistry, May 18, 2007, pp. 15228-15237, vol. 282 Issue 20.

Hald, et al. "Pancreatic Islet and Progenitor Cell Surface Markers with Cell Sorting Potential". Diabetologia (2012) 55:154-165.

Heinis, et al., Oxygen Tension Regulates Pancreatic Beta-Cell Differentiation Through Hypoxia-Inducible Factor 1x, Diabetes, 2010, pp. 662-669, vol. 59.

Hsun Teresa Ku,et al, "Committing Embryonic Stem Cells to Early Endocrine Pancreas In Vitro", <<Stem Cells>>.

Iype, et al. "The Transcriptional Repressor Nkx6.1 Also Functions as Deoxyribonucleic Acid Context-Dependent Transcriptional Activator During Pancreatic B-cell Differntiation: Evidence for Feedback Acitivation of the nkx6.1 Gene by Nkx6.1" Molecular Endocrinology 18(6): 1363-1375.

JPN6013022118; GIBCO 2004~2005, 年版カタログ 細胞培養製品. JPN6014020429; World J. Gastroenterol. , 2004, 10 (20) , p. 3016-20.

Kevin A D'Amour, et al, "Production of pancreatic hormone-expressing endocrine cells from human embryonic stem cells", << Nature Biotechnology>>.

Korytnikov, et al. "Generation of Polyhormonal and Multipotent pancreatic progenitor lineages form human pluripotent stem cells." Methods, vol. 101, May 15, 2016, pp. 56-64.

Ku Hsun Teresa et al, "Committing embryonic stem cells to early endocrine pancreas in vitro", Stem Cells (Miamisburg), (2004), vol. 22, No. 7, ISSN 1066-5099, pp. 1205-1217, XP002507996.

Kubo A et al, "Development of definitive endoderm from embryonic stem cells in culture", Development, Company of Biologists, Cambridge, GB, (Apr. 1, 2004), vol. 131, No. 7, ISSN 0950-1991, pp. 1651-1662, XP002985523.

Kunisada, et al., Small molecules induce efficient differentiation into insulin-producing cells from human induced pluripotent stem cells, Stem Cell Research, Oct. 11, 2011, pp. 274-284, vol. 8.

Leontovyc, et al. The Effect of Epigenetic Factors on Differentiation of Pancreatic Progenitor Cells into Insulin-Producing Cells. Transplant. Proc., 2011, vol. 43, pp. 3212-3216.

Mfopou, et al. "Noggin, Retinoids, and Fibroblast Growth Factor Regulate Hepatic or Pancreatic Fate of Human Embryonic Stem Cells." Gastroenterology 2010; 138:2233-2245.

Micallef, et al. "INSGFP/W Human Emryonic Stem Cells Facilitate Isolation of in vitro derived insulin-producing cells." Diabetologia (2012) 55: 694-706.

Shi Y et al, "Inducing Embryonic Stem Cells to Differentiate Into Pancreatic Beta Cells by a Novel Three-Step Approach With Activin A and All-Trans Retinoic Acid", Stem Cells, Alphamed Press, Dayton, OH, US, (Jan. 1, 2005), vol. 23, No. 5, ISSN 1066-5099, pp. 656-662, XP008059753.

Stassi, et al. "Expression of Apotosis-Inducing CD95 (Fas/Apo-1) on Human B-Cells Sorted by Flow-Cytometry and Cultured in Vitro." Transplantation Proceedings, vol. 27, No. 6 (December), 1995: 3271-3275.

Thermofisher Scientific, B-27 Serum-Free Supplement 50x Liquid, Technical Resources, 2016, URL:https://www.thermofisher.com/nl/en/home/technical-resources/media-formulation.250.html, retrieved from the internet.

Inman, et al., SB-431542 is a Potent and Specific Inhibitor of Transforming Growth Factor-B Superfamily Type I Activing Receptor-Like Kinase (ALK) Receptors Alf.4, Alf.5, and ALK7, Molecular Pharmacology, 2002, pp. 65-74, vol. 62, No. 1.

Ku et al., Committing Embryonic Stem Cells to Early Endocrine Pancreas In Vitro, Stem Cells, 2004, vol. 22, pp. 1205-1217, AlphaMed Press.

Murtaugh, et al., Notch Signaling Controls Multiple Steps of Pancreatic Differentiation, 2003, PNAS, vol. 100, No. 25, pp. 14928-14925.

Nishimura et al., A Switch from MafB to MafA Expression Accompanies Differentiation to B-Cells, Developmental Biology, 2006, vol. 293, pp. 526-539.

Agulnick et al., Stem Cells Transl Med, 2015, Insulin-Producing Endocrine Cells Differentiated In Vitro from Human Embryonic Stem Cells Function in Macroencapsulation Devices In Vivo, 4: 1-9.

Cai et al., Prospectively Isolated NGN3-Expressing Progenitors from Human Embryonic Stem Cells give Rise to Pancreatic Endocrine Cells, Stem Cells Translational Medicine, e-pub, Feb. 2014, pp. 489-499, vol. 3, No. 4.

D'Amour et al., Production of pancreatic hormone-expressing endocrine cells from human embryonic stem cells, Nature Biotechnology, Oct. 19, 2006, 1392-1401, vol. 24 Issue 11, Nature Publishing Group, US.

Fryer, et al., Generating B-cells in vitro : progress towards a Holy Grail, Curr Opin Endocrinol Diabetes obes, 2013, pp. 112-117, vol. 20 Issue 2.

Jiang, et al., Generation of Insulin-Producing Islet-Like Clusters from Human Embryonic Stem Cells, 2007, Stem Cells, pp. 1940-1953, vol. 25.

Pagliuca et al., How to Make a Functional Beta-Cell, Development, 2013, pp. 2472-2483, vol. 140, No. 2.

Wei et al., Cdk5-dependent regulation of glucose-stimulated insulin secretion, Nature Medicine, Sep. 11, 2005, 1104-1108, 11-10, Nature Publishing Group.

Zhang et al. Highly Efficient Differentiation of Human ES Cells and IPS Cells into Mature Pancreatic Insulin-Producing Cells, Cell Research, 2009, pp. 429-438, vol. 19, Issue 4.

Zhang et al., MafA is a Key Regulator of Glucose-Stimulated Insulin Secretion, Molecular and Cellular Biology, Jun. 2005, 4969-4976, 25-12, American Society for Microbiology.

Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.

* cited by examiner

Untreated

Treated

PDX1

Untreated

RA+bFGF

SEQUENCE LISTING

<160> NUMBER OF SEQ ID NOS: 3

<210> SEQ ID NO 1
<211> LENGTH: 17
<212> TYPE: DNA
<213> ORGANISM: Artificial Sequence

```
<220> FEATURE:
<223> OTHER INFORMATION: Synthetic oligonucleotide

<400> SEQUENCE: 1
tggcgcagca gatacca                                                  17

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 2
agcgccttcc acgacttg                                                 18

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 3
ccagcatctt gctcaactcg gcg                                           23
```

PANCREATIC ENDOCRINE CELLS AND METHODS THEREOF

FIELD OF THE INVENTION

The present invention provides methods to promote the differentiation of pluripotent stem cells. In particular, the present invention provides an improved method for the formation of pancreatic endoderm, pancreatic hormone expressing cells and pancreatic hormone secreting cells. The present invention also provides methods to promote the differentiation of pluripotent stem cells without the use of a feeder cell layer.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF-3beta, GATA4, Mix11, CXCR4 and Sox-17.

Formation of the pancreas arises from the differentiation of definitive endoderm into pancreatic endoderm. Cells of the pancreatic endoderm express the pancreatic-duodenal homeobox gene, Pdx1. In the absence of Pdx1, the pancreas fails to develop beyond the formation of ventral and dorsal buds. Thus, Pdx1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form Pdx1 positive pancreatic endoderm. Retinoic acid is most effective at inducing Pdx1 expression when added to cultures at day 4 of embryonic stem cell differentiation during a period corresponding to the end of gastrulation in the embryo (Diabetes 54:301, 2005).

Miyazaki et al. reports a mouse embryonic stem cell line over-expressing Pdx1. Their results show that exogenous Pdx1 expression clearly enhanced the expression of insulin, somatostatin, glucokinase, neurogenin3, P48, Pax6, and HNF6 genes in the resulting differentiated cells (Diabetes 53: 1030, 2004).

Skoudy et al. reports that activin A (a member of the TGFβ superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into Pdx1 positive cells. They observed that TGFβ2 reproducibly yielded a higher proportion of Pdx1 positive cells (Genes Cells. 2005 June; 10(6): 503-16).

Gordon et al. demonstrated the induction of brachyury$^+$/HNF-3beta$^+$ endoderm cells from mouse embryonic stem cells in the absence of serum and in the presence of activin along with an inhibitor of Wnt signaling (US 2006/0003446A1).

Gordon et al. (PNAS, Vol 103, page 16806, 2006) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (Nature Biotechnology 2005). Transplanting these cells under the kidney capsule of mice resulted in differentiation into more mature cells with characteristics of some endodermal organs. Human embryonic stem cell-derived definitive endoderm cells can be further differentiated into Pdx1 positive cells after addition of FGF-10 (US 2005/0266554A1).

D'Amour et al. (Nature Biotechnology—24, 1392-1401 (2006)) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of sodium butyrate and activin A. The cells were then cultured with TGFβ antagonists such as Noggin in combination with EGF or betacellulin to generate Pdx1 positive cells. The terminal differentiation was induced by nicotinamide.

In one example, Benvenistry et al. states: "We conclude that over-expression of Pdx1 enhanced expression of pancreatic enriched genes, induction of insulin expression may require additional signals that are only present in vivo" (Benvenistry et al, Stem Cells 2006; 24:1923-1930).

Therefore, there still remains a significant need to develop conditions for establishing pluripotent stem cell lines that can be expanded to address the current clinical needs, while retaining the potential to differentiate into pancreatic endocrine cells, pancreatic hormone expressing cells, or pancreatic hormone secreting cells. We have taken an alternative approach to improve the efficiency of differentiating human embryonic stem cells toward pancreatic endocrine cells.

SUMMARY

In one embodiment, the present invention provides a method for differentiating pluripotent stem cells, comprising the steps of:
  a. Culturing the pluripotent stem cells,
  b. Differentiating the pluripotent stem cells into cells expressing markers characteristic of the definitive endoderm lineage,
  c. Differentiating the cells expressing markers characteristic of the definitive endoderm lineage into cells expressing markers characteristic of the pancreatic endoderm lineage, and
  d. Differentiating the cells expressing markers characteristic of the pancreatic endoderm lineage into cells expressing markers characteristic of the pancreatic endocrine lineage.

In one embodiment, cells expressing markers characteristic of the definitive endoderm lineage are differentiated from pluripotent stem cells by treating pluripotent stem cells by any one of the following methods:
  a. Culturing the pluripotent stem cells in medium containing activin A in the absence of serum, then culturing the cells with activin A and serum, and then culturing the cells with activin A and serum of a different concentration, or
  b. Culturing the pluripotent stem cells in medium containing activin A in the absence of serum, then culturing the cells with activin A with serum of another concentration, or
  c. Culturing the pluripotent stem cells in medium containing activin A and a Wnt ligand in the absence of serum, then removing the Wnt ligand and culturing the cells with activin A with serum, or
  d. Culturing the pluripotent stem cells on a tissue culture substrate coated with an extracellular matrix, and culturing the pluripotent stem cells with activin A and a Wnt ligand, or
  e. Culturing the pluripotent stem cells on a tissue culture substrate coated with an extracellular matrix, then culturing the pluripotent stem cells with activin A and a Wnt ligand in a first culture medium containing serum, then culturing the pluripotent stem cells with activin A in a second culture medium containing serum, or
  f. Culturing the pluripotent stem cells on a tissue culture substrate coated with an extracellular matrix, then culturing the pluripotent stem cells with activin A and a Wnt ligand in a first culture medium containing serum, then culturing the pluripotent stem cells with activin A and a Wnt ligand in a second culture medium containing serum of a different concentration.

In one embodiment, cells expressing markers characteristic of the pancreatic endoderm lineage are differentiated from cells expressing markers characteristic of the definitive endoderm lineage by treating cells expressing markers characteristic of the definitive endoderm lineage by any one of the following methods:
  a. Treating the cells expressing markers characteristic of the definitive endoderm lineage with a fibroblast growth factor and a hedgehog signaling pathway inhibitor, then removing the medium containing the fibroblast growth factor and the hedgehog signaling pathway inhibitor and subsequently culturing the cells in medium containing retinoic acid, a fibroblast growth factor and the hedgehog signaling pathway inhibitor, or
  b. Treating the cells expressing markers characteristic of the definitive endoderm lineage with retinoic acid and at least one fibroblast growth factor, or
  c. Treating the cells expressing markers characteristic of the definitive endoderm lineage with retinoic acid, then removing the retinoic acid and subsequently treating the cells with at least one fibroblast growth factor.

In one embodiment, cells expressing markers characteristic of the pancreatic endocrine lineage are differentiated from cells expressing markers characteristic of the pancreatic endoderm lineage by treating cells expressing markers characteristic of the pancreatic endoderm lineage by any one of the following methods:
  a. Culturing the cells expressing markers characteristic of the pancreatic endoderm lineage in medium containing DAPT and exendin 4, then removing the medium containing DAPT and exendin 4 and subsequently culturing the cells in medium containing exendin 1, IGF-1 and HGF, or
  b. Culturing the cells expressing markers characteristic of the pancreatic endoderm lineage in medium containing exendin 4, then removing the medium containing exendin 4 and subsequently culturing the cells in medium containing exendin 1, IGF-1 and HGF, or
  c. Culturing the cells expressing markers characteristic of the pancreatic endoderm lineage in medium containing DAPT and exendin 4, or
  d. Culturing the cells expressing markers characteristic of the pancreatic endoderm lineage in medium containing exendin 4, or
  e. Treating the cells expressing markers characteristic of the pancreatic endoderm lineage with a factor that inhibits the Notch signaling pathway, or
  f. Culturing the cells expressing markers characteristic of the pancreatic endoderm lineage in medium containing from about 10 mM to about 20 mM glucose and exendin 4.

In one embodiment, the present invention provides a method for treating a patient suffering from diabetes, comprising the steps of:
  a. Culturing pluripotent stem cells,
  b. Differentiating the pluripotent stem cells into cells expressing markers characteristic of the definitive endoderm lineage,
  c. Differentiating the cells expressing markers characteristic of the definitive endoderm lineage into cells expressing markers characteristic of the pancreatic endoderm lineage,
  d. Differentiating the cells expressing markers characteristic of the pancreatic endoderm lineage into cells of a β-cell lineage, and
  e. Implanting the cells of a β-cell lineage into the patient.

BRIEF DESCRIPTION OF THE DRAWINGS

FIG. 2A shows Sox-17 expression. FIG. 2B shows HNF-3beta expression. FIG. 2C shows Oct3/4 expression.

FIG. 3A shows GATA4 expression. FIG. 3B shows Sox-17 expression. FIG. 3C shows HNF-3beta expression.

FIG. 4A shows the effect of 100 ng/ml activin A on AFP expression. FIG. 4B shows the effect of 100 ng/ml activin A on Sox7 expression. Data points marked 'AA' denote activin A treatment for one (1 d), three (3 d), five (5 d), or seven days (7 d). Data points marked 'UT' denote untreated controls cultured for one (1 d), three (3 d), five (5 d), or seven days (7 d).

FIG. 5A shows the effect of 100 ng/ml activin A on Brachyury expression. FIG. 5B shows the effect of 100 ng/ml activin A on Zic1 expression. Data points marked 'AA' denote activin A treatment for one (1 d), three (3 d), five (5 d), or seven days (7 d). Data points marked 'UT' denote untreated controls cultured for one (1 d), three (3 d), five (5 d), or seven days (7 d).

FIG. 7A and FIG. 7B show Sox-17 expression. FIG. 7C and FIG. 7C show HNF-3beta expression. FIG. 7E and FIG. 7F show GATA4 expression. FIGS. 7B, 7D and 7F show counter staining of the nuclei with DAPI. The columns marked 'treated' denote activin A treatment (100 ng/ml) for five days. The columns marked 'untreated' denote untreated controls.

FIG. 8A shows Pdx1 expression. FIG. 8B shows GLUT-2 expression. FIG. 8C shows PTF1a expression.

FIG. 9A shows Pdx1 expression in the untreated control, and FIG. 9B shows Pdx1 expression in the culture treated by the stepwise differentiation protocol.

FIG. 10A shows NeuroD1 expression. FIG. 10B shows Ngn3 expression. FIG. 10C shows insulin expression. FIG. 10D shows Hes-1 expression, the expression level is normalized to pancreatic endoderm cells.

FIG. 11A shows Nkx2.2 expression. FIG. 11B shows Pdx1 expression.

FIG. 13A shows AFP expression. FIG. 13B shows albumin expression.

(CD184) is shown on the Y-axis and the expression of ES marker CD9 is shown on the X-axis.

Figure 18:
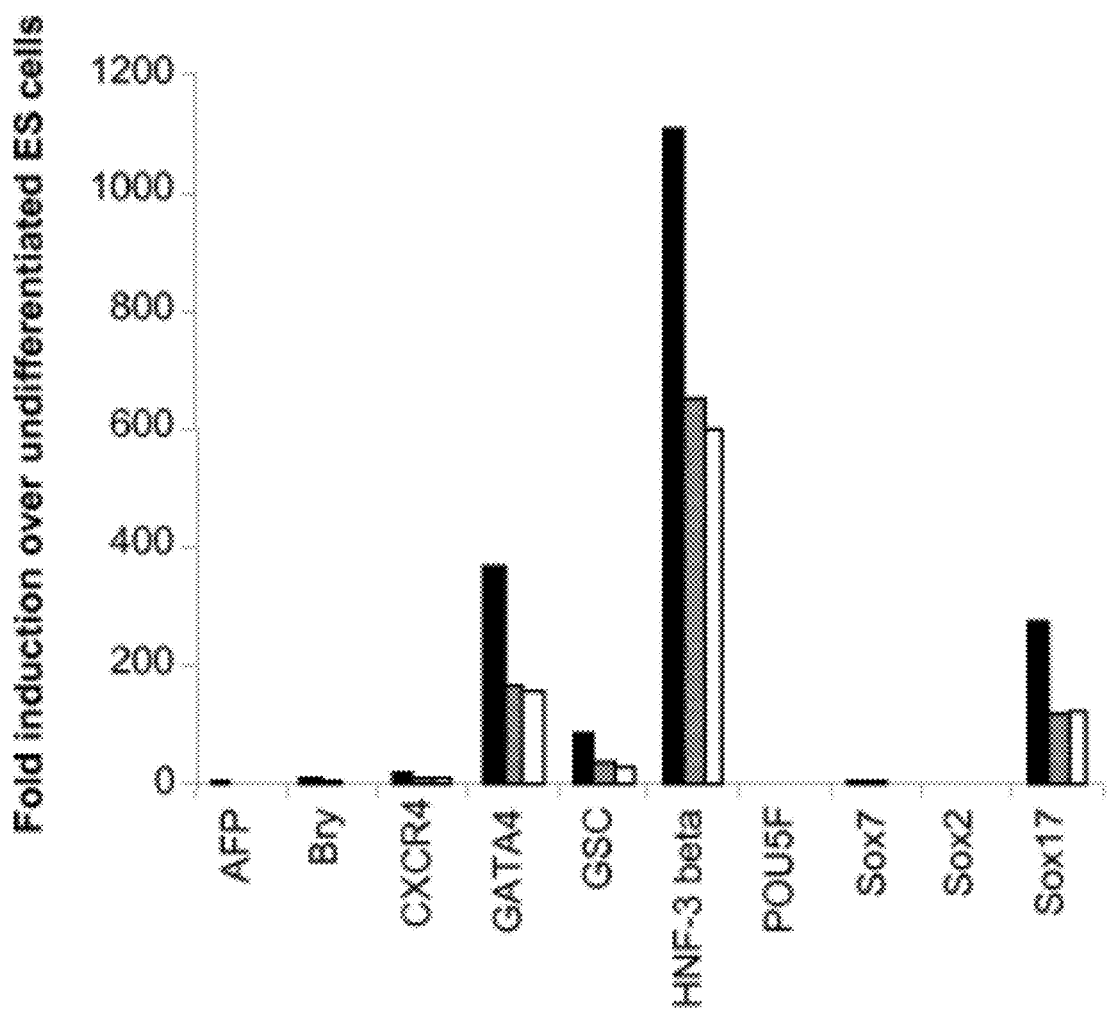

FIG. 18 shows the real-time PCR results for markers of definitive endoderm, from cultures of the human embryonic stem cell line H9 at passage 44 cultured on a 1:10 dilution of MATRIGEL (■), a 1:20 dilution of MATRIGEL (▨), or a 1:30 dilution of MATRIGEL (□) and exposed to the differentiation protocol disclosed in Example 14. The fold induction is relative to undifferentiated cells of the human embryonic stem cell line H9, at passage number 44, cultured in medium conditioned using mouse embryonic fibroblasts.

Figure 19:
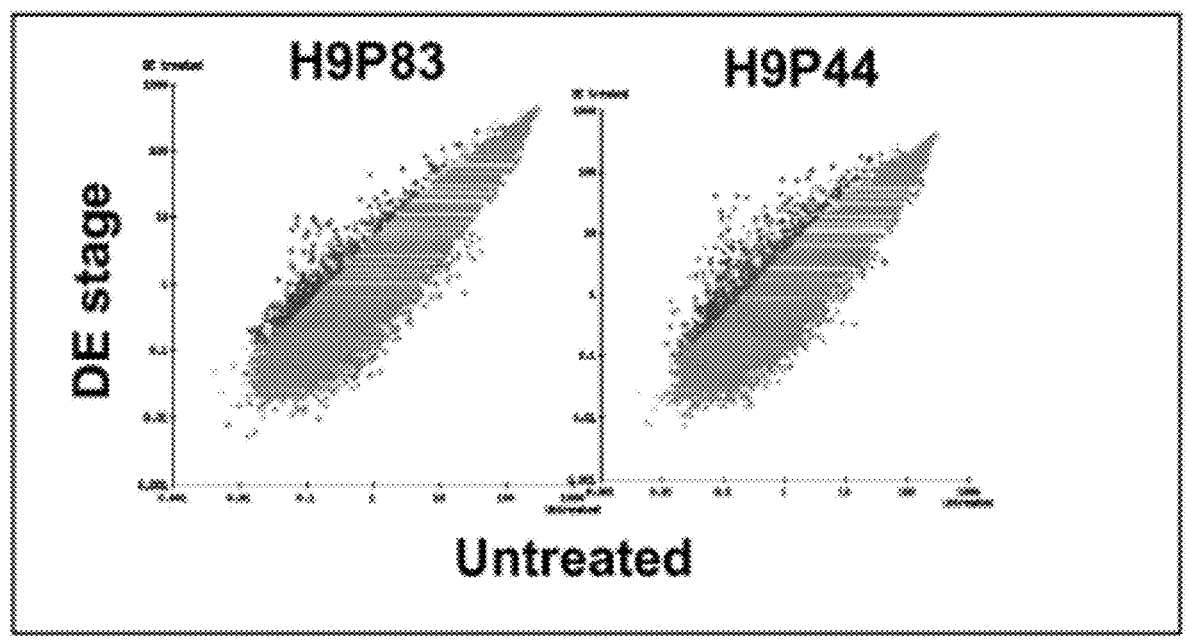

FIG. 19 shows the scatter plots for global gene expression in undifferentiated pluripotent stem cells and definitive endoderm cells obtained from differentiating pluripotent stem cells. Data shown is from cultures of the human embryonic stem cell line H9 cell line at passage 44 cultured on mouse embryonic fibroblasts (right panel) and passage 83 cultured on MATRIGEL (left panel).

Figure 20A:
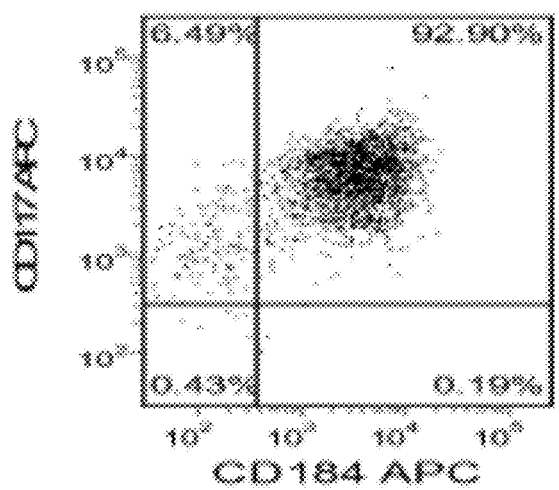
Figure 20B:
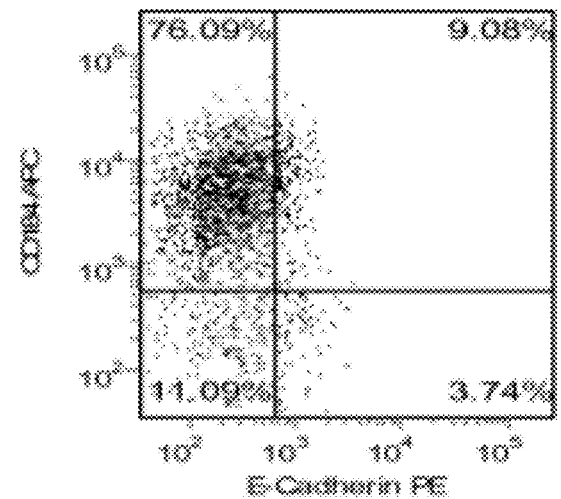
Figure 20C:
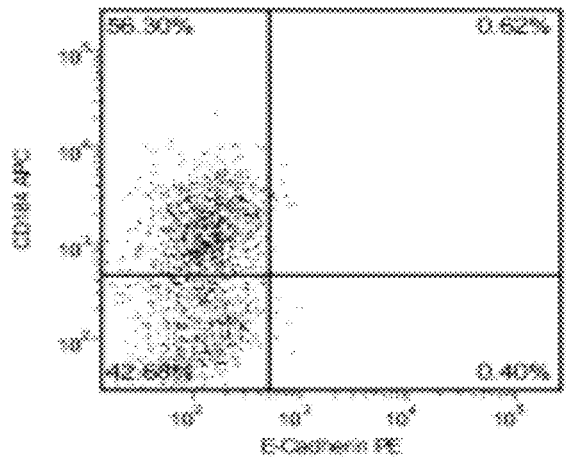

FIGS. 20A-20C depict the expression of CXCR4 by FACS at day 5 for the human embryonic stem cell line H1 (FIG. 20A), the human embryonic stem cell line H7 (FIG. 20B), and the human embryonic stem cell line H9 (FIG. 20C) cultured on mouse embryonic fibroblast feeder cells exposed to the definitive endoderm differentiation protocol disclosed in Example 4.

Figure 21A:
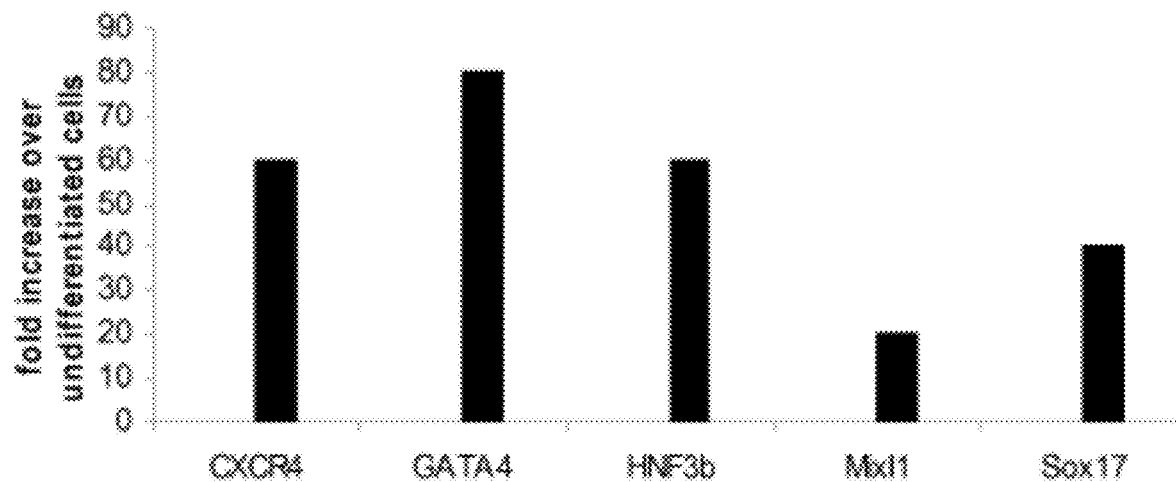
Figure 21B:
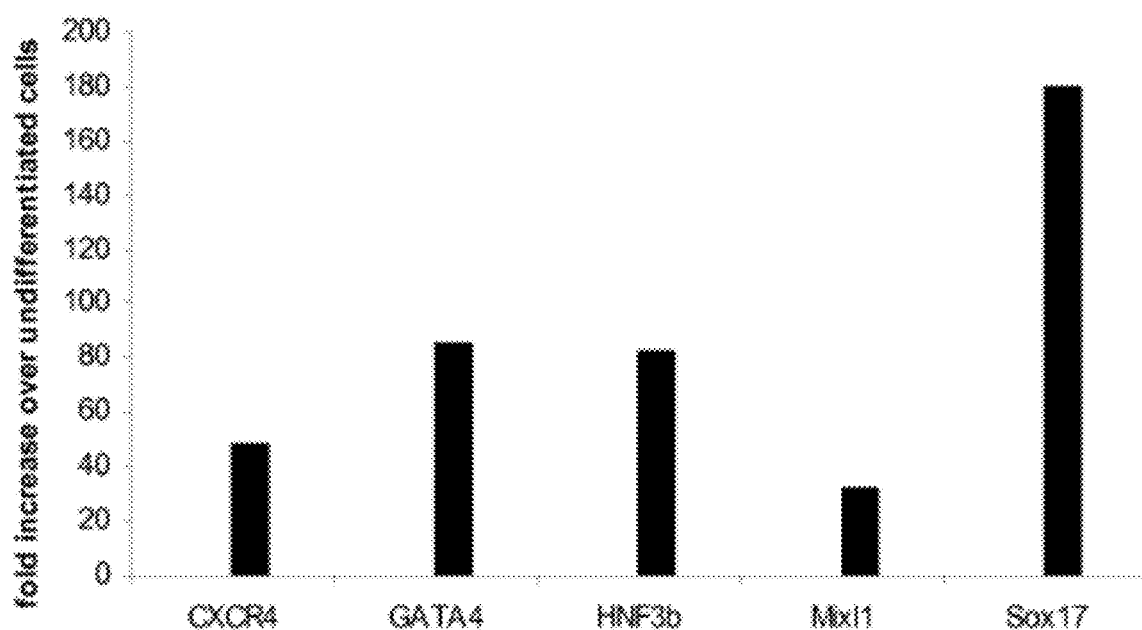

FIGS. 21A-21B shows the real-time PCR results of expression of the indicated definitive endoderm markers in cultures of the human embryonic stem cell line H7 (FIG. 21A) and the human embryonic stem cell line H9 (FIG. 21B) cultured on mouse embryonic fibroblast feeder cells. Results are expressed as fold increase over undifferentiated cells.

Figure 22A:
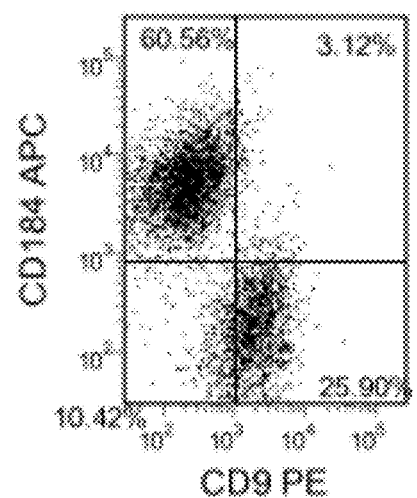
Figure 22B:
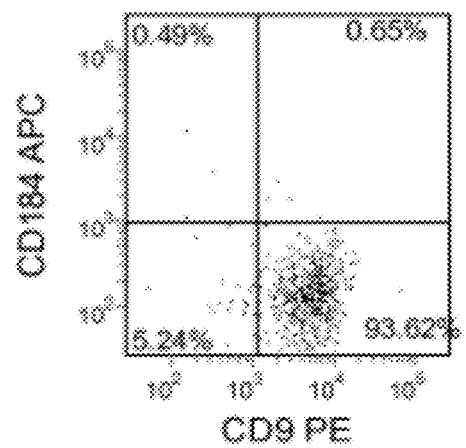
Figure 22C:
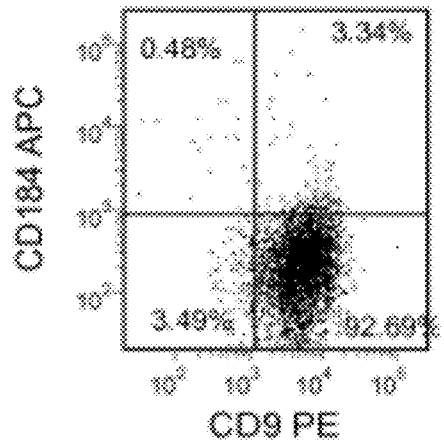

FIGS. 22A-22C depict the expression of CXCR4 by FACS at day 5 for the human embryonic stem cell line H1 (FIG. 22A), the human embryonic stem cell line H7 (FIG. 22B), and the human embryonic stem cell line H9 (FIG. 22C) cultured on MATRIGEL (1:30 dilution) and exposed to the definitive endoderm differentiation protocol disclosed in Example 4.

Figure 23A:
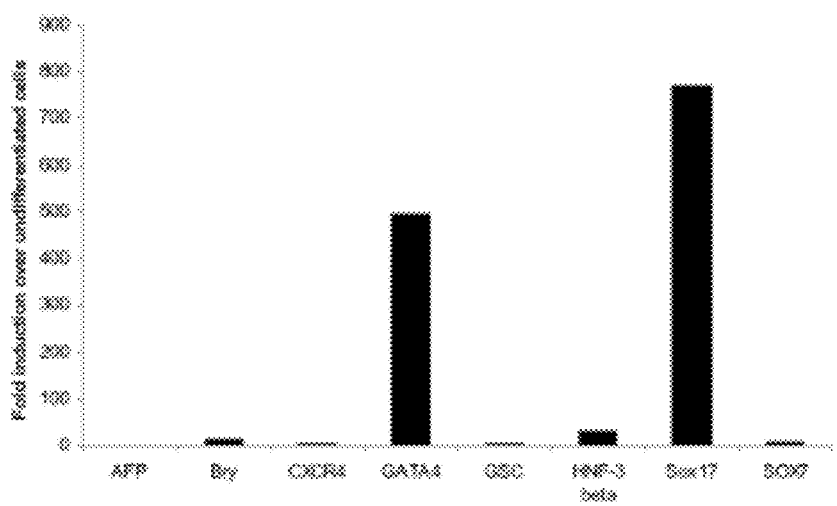
Figure 23B:
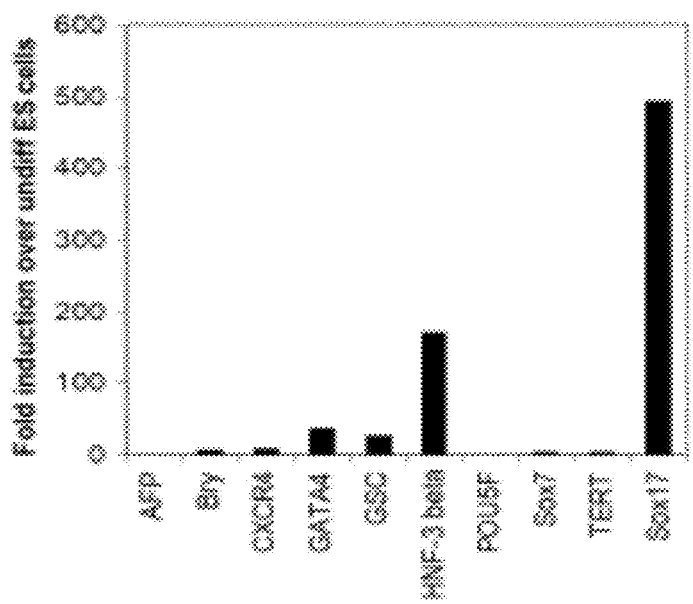
Figure 23C:
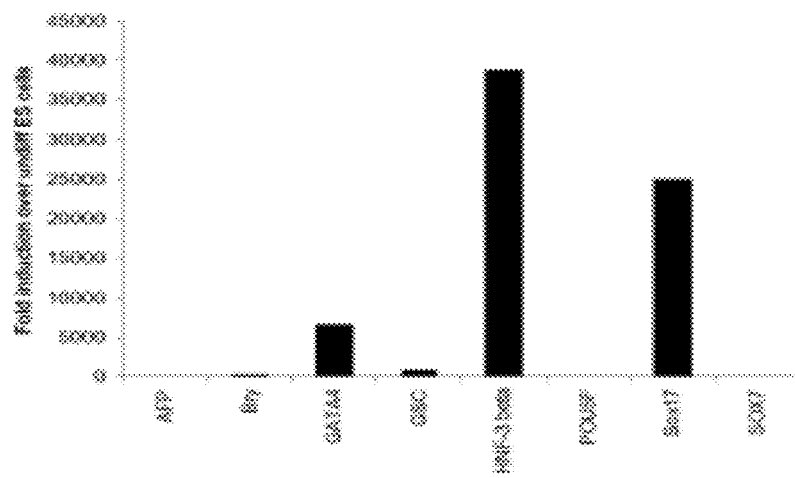

FIGS. 23A-23C show the real-time PCR results of the expression of the indicated definitive endoderm markers in cultures of the human embryonic stem cell line H7 (FIG. 23A) and the human embryonic stem cell line H9 (FIG. 23B) and the human embryonic stem cell line H1 (FIG. 23C). Results are expressed as fold increase over undifferentiated cells. Cells were treated according to the methods disclosed in Example 4.

Figure 24A:
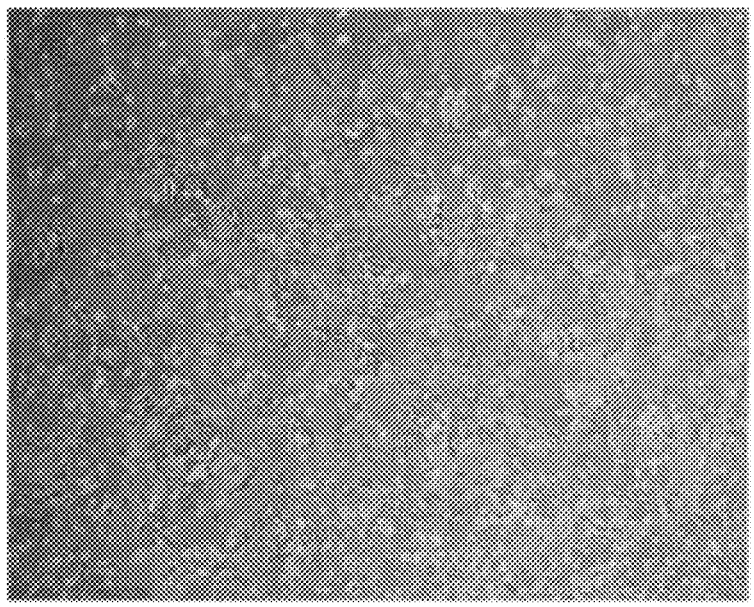
Figure 24B:
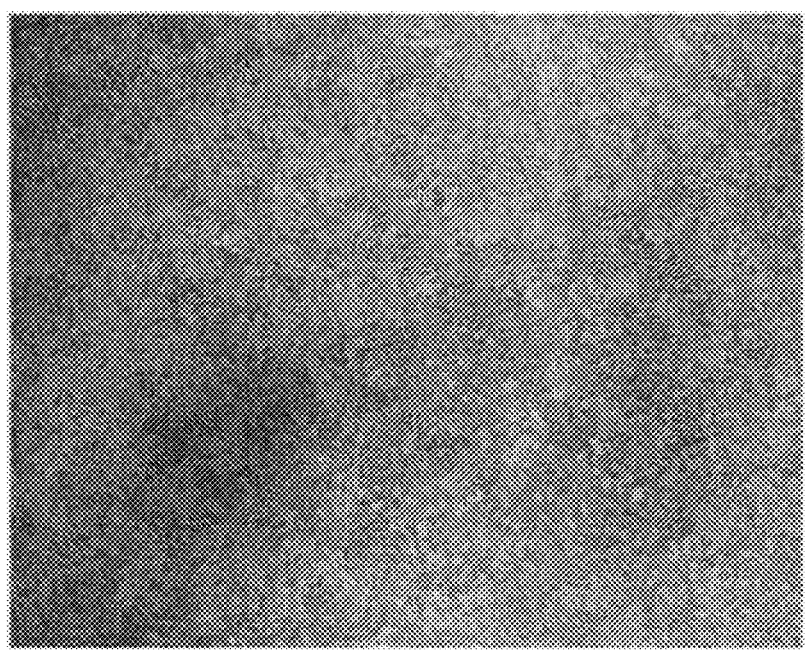

FIGS. 24A-24B depict phase contrast images of cultures of the human embryonic stem cell line H9 at passage 46 in the presence of 100 ng/ml of activin A (FIG. 24A) or 100 ng/ml of activin A+20 ng/ml Wnt-3a (FIG. 24B). Cells were treated for five days.

Figure 25A:
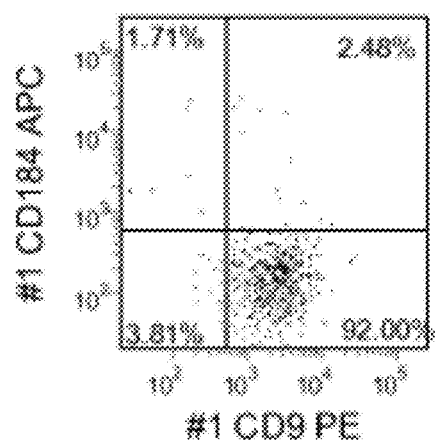
Figure 25B:
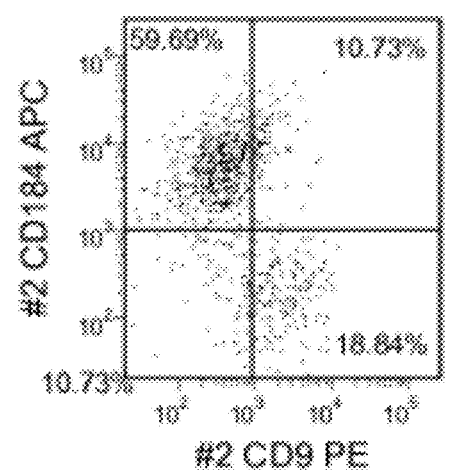
Figure 25C:
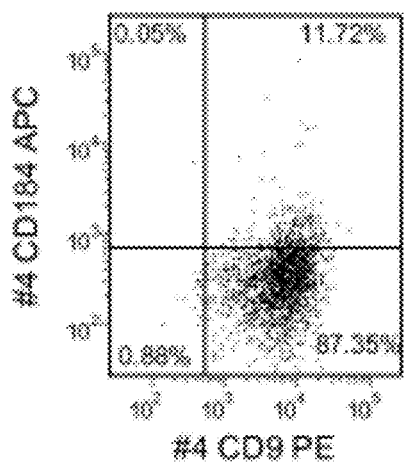
Figure 25D:
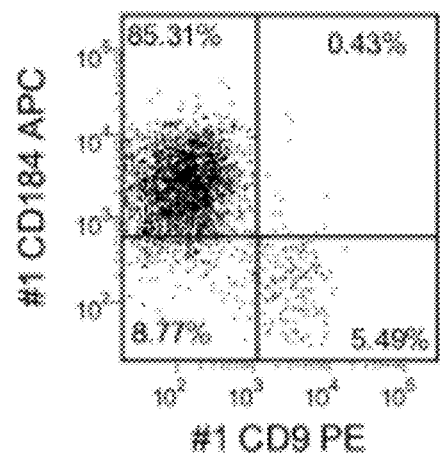

FIGS. 25A-25D depict the expression of CXCR4 by FACS in cultures of the human embryonic stem cell line H7 at passage 44 (FIGS. 25A and 25B) and H9 at passage 46 (FIGS. 25C and 25D), following treatment according to the methods disclosed in Example 4. FIGS. 25B and 25D show the effect of 20 ng/ml of Wnt-3a on CXCR4 expression. FIGS. 25A and 25C show CXCR4expression in the absence of Wnt-3a. Results were obtained 5 days post treatment.

Figure 26A:
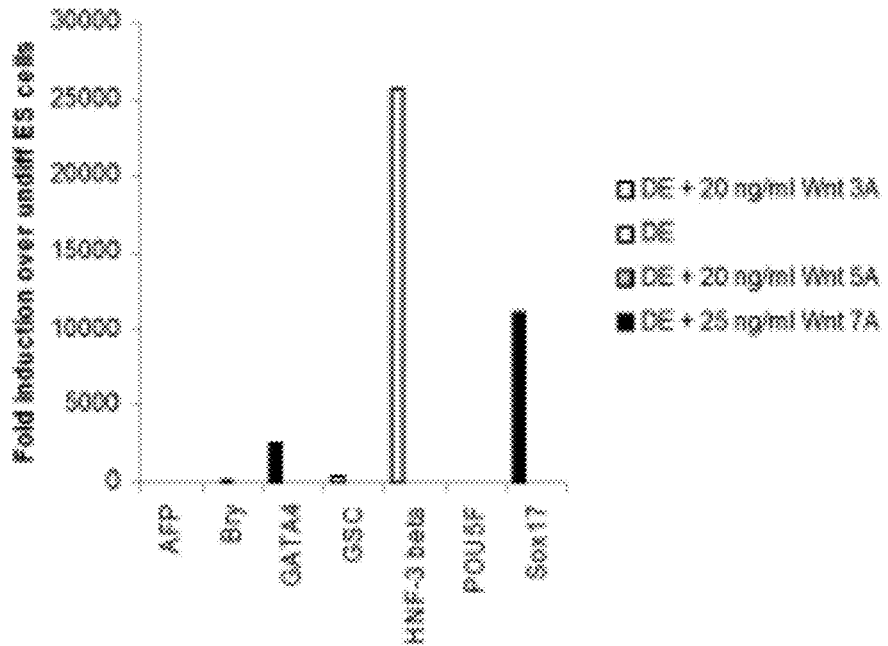
Figure 26B:
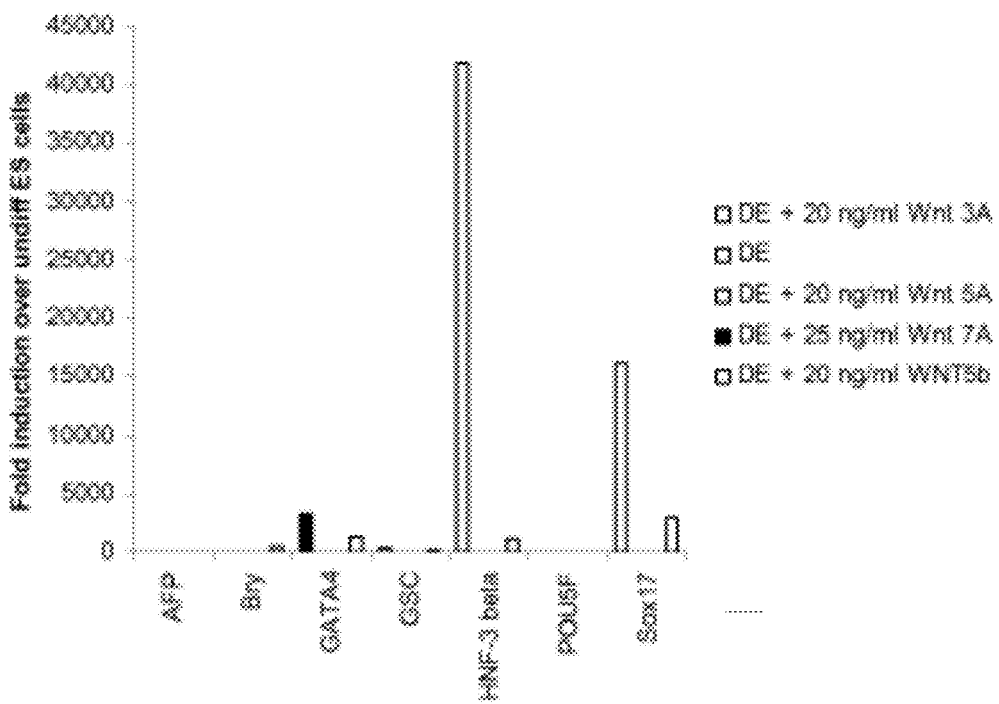

FIGS. 26A-26B display the real-time PCR data for expression of the genes indicated in cultures of the human embryonic stem cell line H7 (FIG. 26A) and H9 (FIG. 26B). Cultures were treated with the differentiation protocol disclosed in Example 4. The effects of Wnt agonists Wnt-3a (20 ng/ml), Wnt-5a (20 ng/ml) and Wnt-7a (20 ng/ml) were also tested, as indicated in the figures. Cells were treated for 5 days. Results are expressed as fold increase over undifferentiated cells.

Figure 27A:
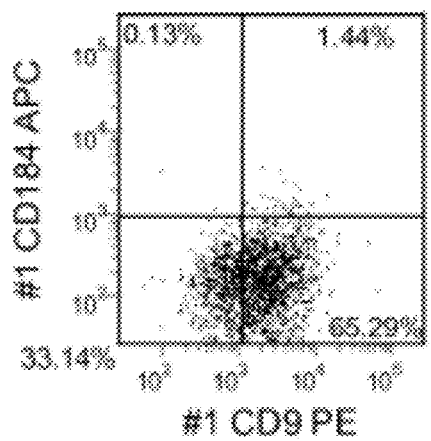
Figure 27B:
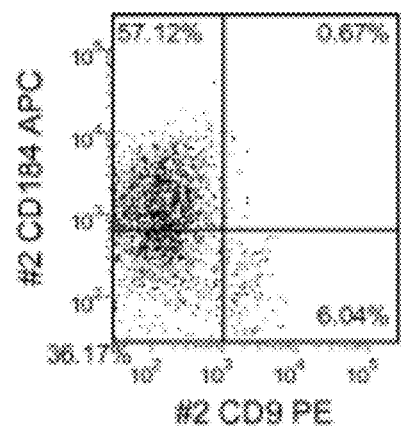
Figure 27C:
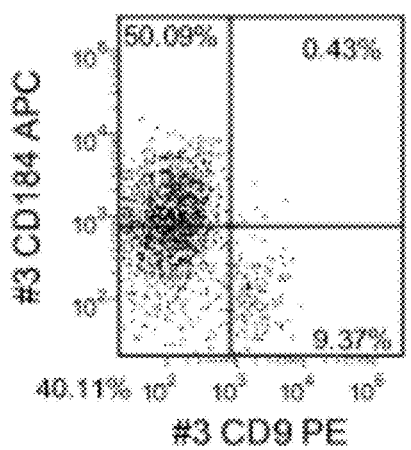
Figure 27D:
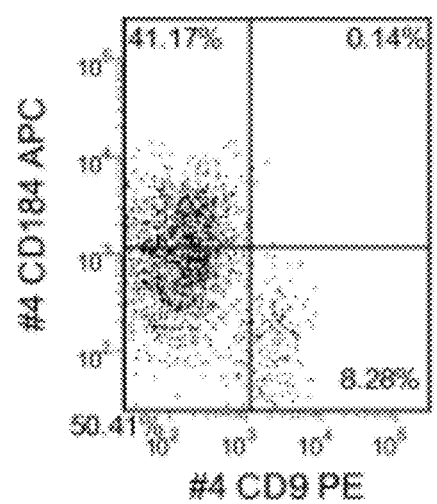

FIGS. 27A-27D depict the expression of CXCR4 in cultures of the human embryonic stem cell line H9 at passage 46, by FACS at five days post treatment. FIG. 27A depicts CXCR4 expression in the absence of Wnt-3a. FIG. 27B depicts CXCR4 expression following treatment with 10 ng/ml Wnt-3a. FIG. 27C depicts CXCR4 expression following treatment with 20 ng/ml Wnt-3a, and FIG. 27C depicts CXCR4 expression following treatment with 50 ng/ml Wnt-3a.

Figure 28A:
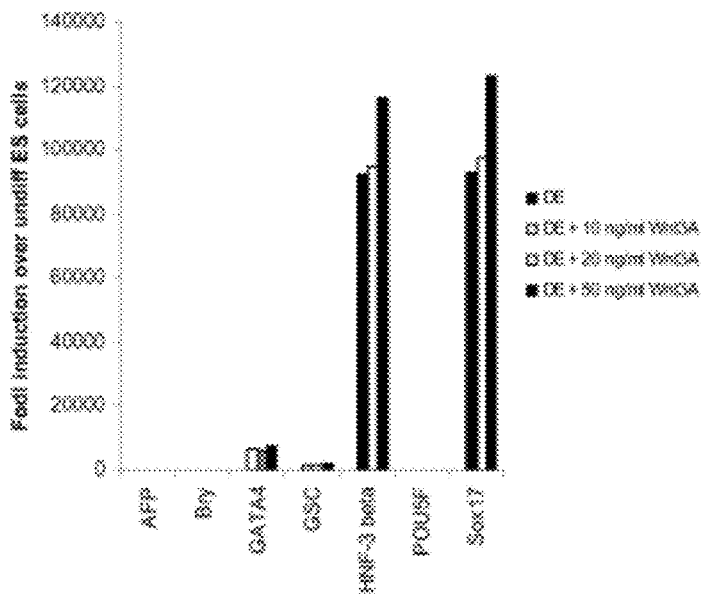
Figure 28B:
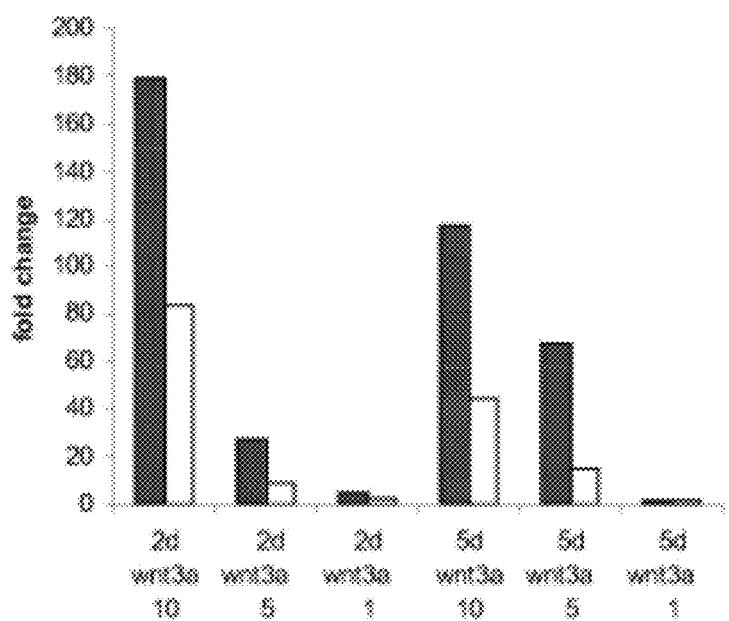
Figure 28C:
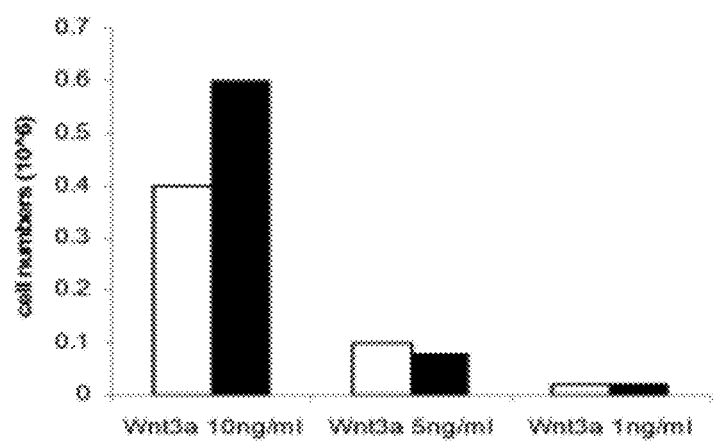

FIGS. 28A-28C depict the expression of definitive markers indicated in cultures of the human embryonic stem cell line H9 after 5 days of treatment. Results are shown as fold increase in expression over untreated cells, as determined by real-time PCR. FIG. 28A shows the effect of 10, 20 and 50 ng/ml Wnt-3a on the expression of definitive endoderm marker genes indicated. FIG. 28B shows the effect of 1, 5 or 10 ng/ml Wnt-3a (x-axis labels: 10, 5, 1) on the expression on goosecoid (■) and CXCR4 (□) expression, at 2 (2 d) and 5 (5 d) days post treatment. FIG. 28C shows the effect of 1, 5 or 10 ng/ml Wnt-3a on cell number, at 2 days (■) or 5 days (□).

Figure 29A:
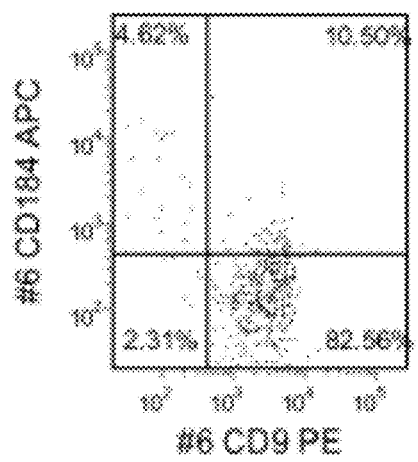
Figure 29B:
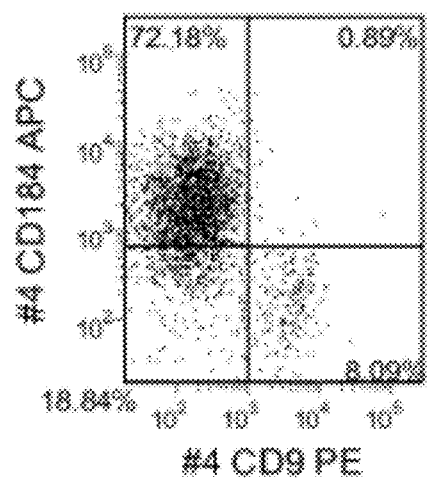
Figure 29C:
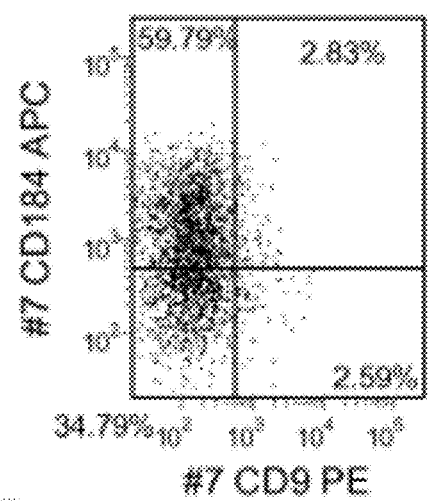
Figure 29D:
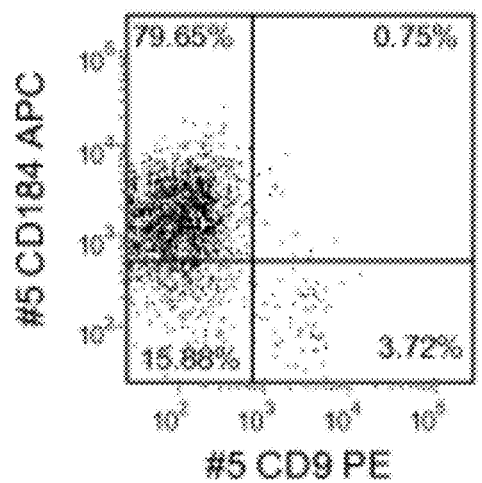
Figure 29E:
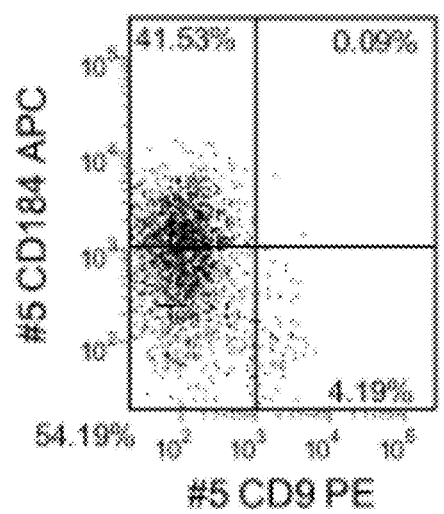
Figure 29F:
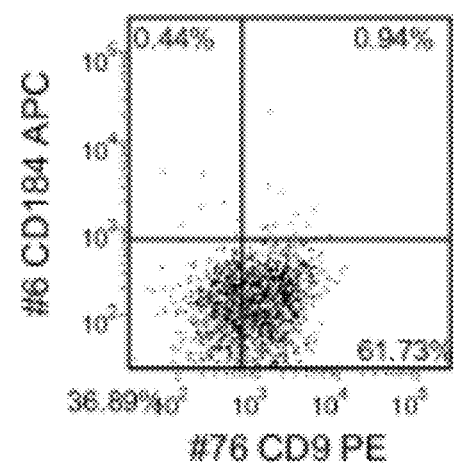
Figure 29G:
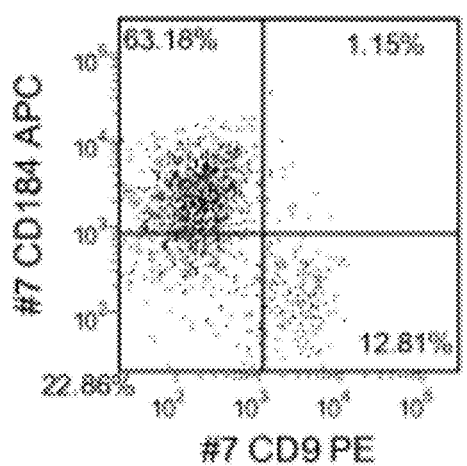
Figure 29H:
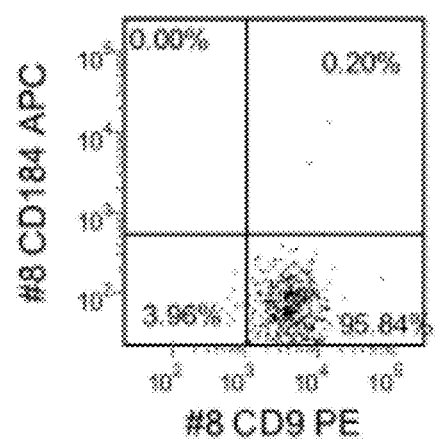

FIGS. 29A-29H depict the expression of CXCR4 in cultures of the human embryonic stem cell line H9 by FACS, following a 5 day treatment with the differentiation protocol disclosed in Example 4. Cells were cultured in the absence of Wnt-3a or GSK-3B inhibitor (FIG. 29A), 20 ng/ml Wnt-3a for the entire 5 day period (FIG. 29B), 1000 nM GSK-3B inhibitor IX for the entire 5 day period (FIG. 29C), 500 nM GSK-3B inhibitor IX for the entire 5 day period (FIG. 29D), 100 nM GSK-3B inhibitor IX for the entire 5 day period (FIG. 29E), 10 nM GSK-3B inhibitor IX for the entire 5 day period (FIG. 29F), 100 nM GSK-3B inhibitor IX for days 1-2 (FIG. 29G), 10 nM GSK-3B inhibitor IX for days 1-2 (FIG. 29H).

Figure 30A:
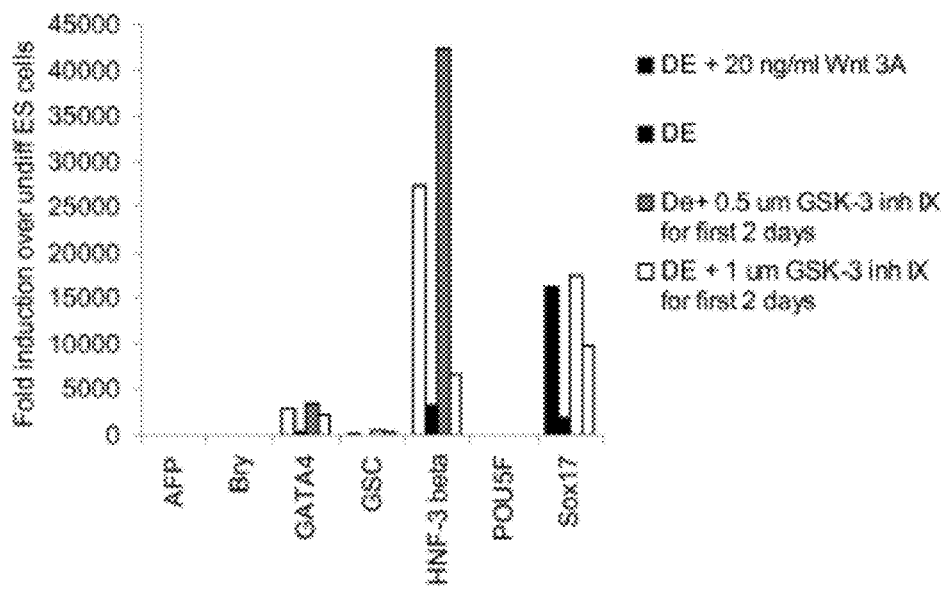
Figure 30B:
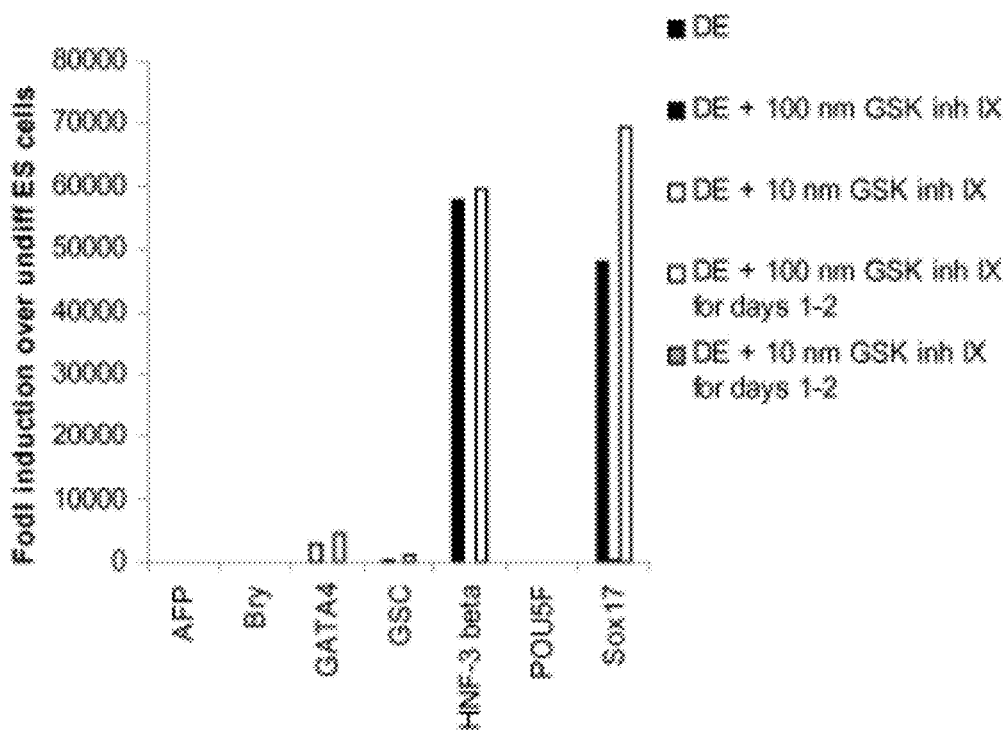

FIGS. 30A-30B depict the gene expression of definitive endoderm markers by real-time PCR. Results are expressed as fold increase over untreated cells. FIG. 30A shows data obtained from the human embryonic cell line H9 at passage number 48, treated to the definitive endoderm protocol disclosed in Example 4, containing the Wnt-3a or GSK-3B inhibitor at the concentrations and the times indicated. FIG. 30B shows data obtained from the human embryonic cell line H9 at passage number 46, treated to the definitive endoderm protocol disclosed in Example 4, containing the Wnt-3a or GSK-3B inhibitor at the concentrations and the times indicated.

Figure 31A:
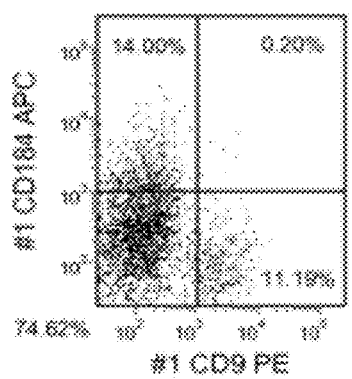
Figure 31B:
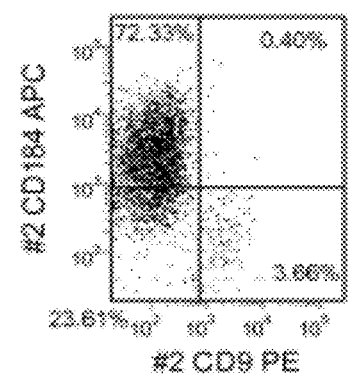
Figure 31C:
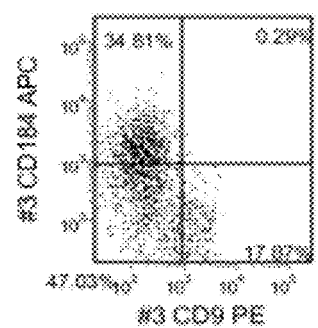
Figure 31D:
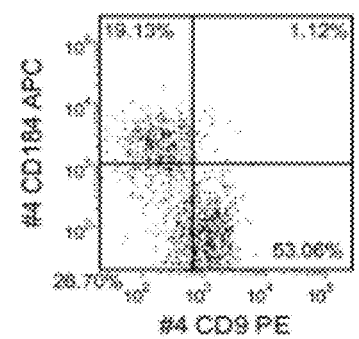
Figure 31E:
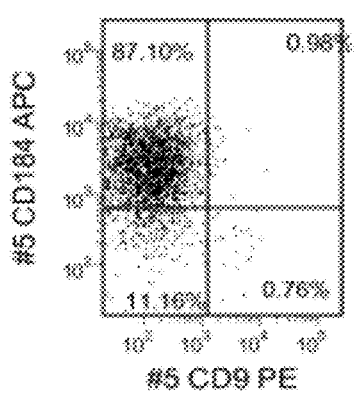
Figure 31F:
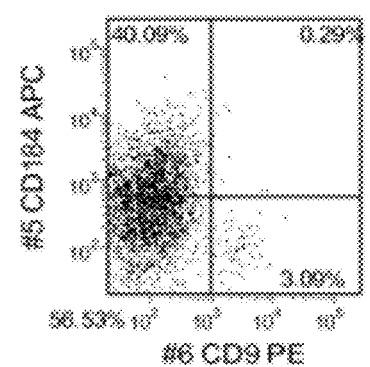

FIGS. 31A-31F depict the expression of CXCR4 by FACS for embryonic stem cell lines used in the present invention. FIGS. 31A-31D show data obtained from the human embryonic stem cell line H9 at passage number 49. FIGS. 31E-31F show data obtained from the human embryonic stem cell line H1 at passage number 46. Data was obtained 5 days post treatment. Cells were treated with the following conditions: FIG. 31A: 10 ng/ml activin A for all five days plus 20 ng/ml of Wnt-3a for the first two days; FIG. 31B: 100 ng/ml activin A for all five days plus 20 ng/ml of Wnt-3a for the first two days; FIG. 31C: 100 ng/ml activin A for all five days plus 100 nM of GSK-3B inhibitor IX for the first two days; FIG. 31D: 10 ng/ml activin A for all five days plus 100 nM GSK-3B IX inhibitor for the first two days, FIG. 31E: 100 ng/ml activin A for all five days plus 20 ng/ml of Wnt-3a for the first two days, and FIG. 31F: 10 ng/ml activin A for all five days plus 20 ng/ml of Wnt-3a for the first two days.

Figure 32A:
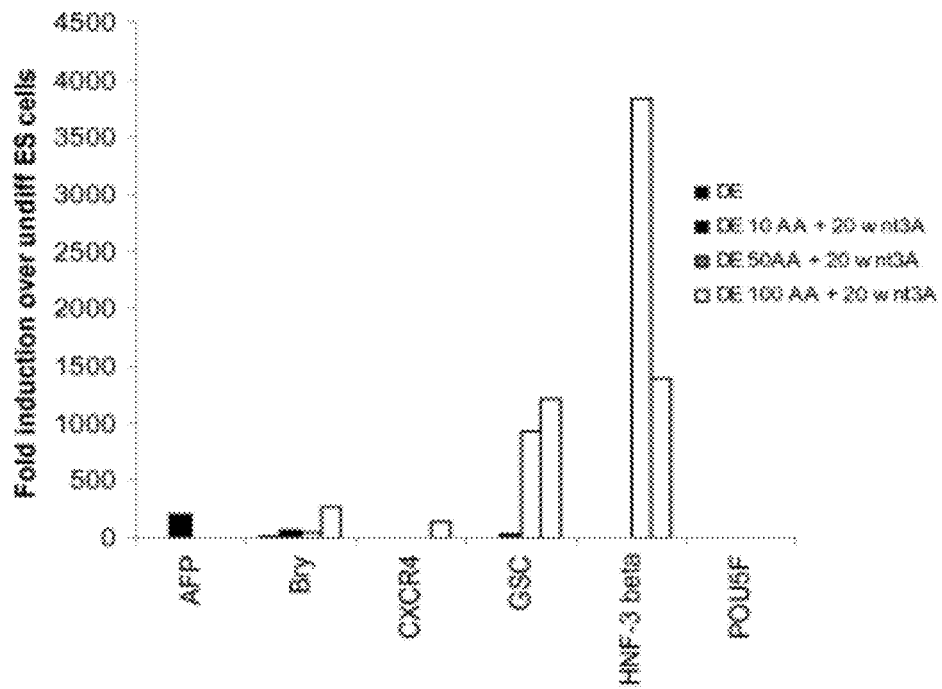
Figure 32B:
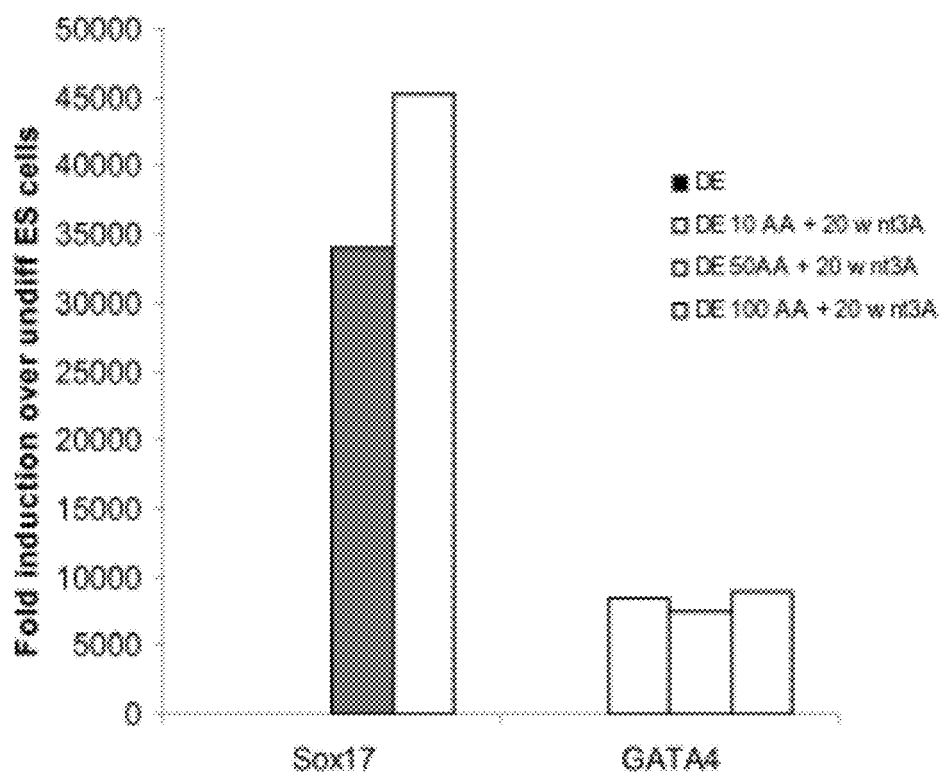

FIGS. 32A-32B depicts the gene expression of definitive endoderm markers, as determined by real-time PCR for cultures of the human embryonic stem cell line H9 at passage 49, treated with 10, 50, or 100 ng/ml of activin A plus 20 ng/ml of Wnt-3a: FIG. 32A: expression of AFP, Bry, CXCR4, GSC, HNF-3B, and POU5F (Oct-4) and FIG. 32B: SOX-17 and GATA4. Results are expressed as fold increase over untreated cells.

Figure 33A:
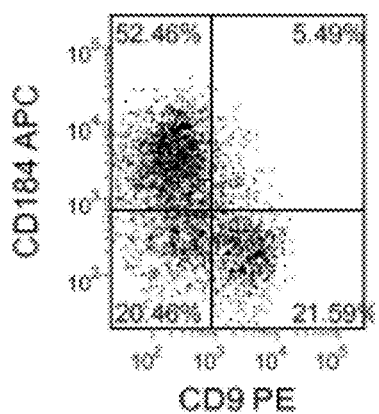
Figure 33B:
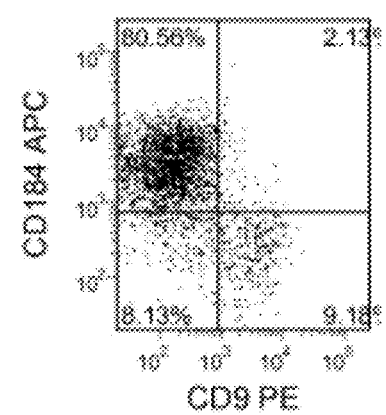
Figure 33C:
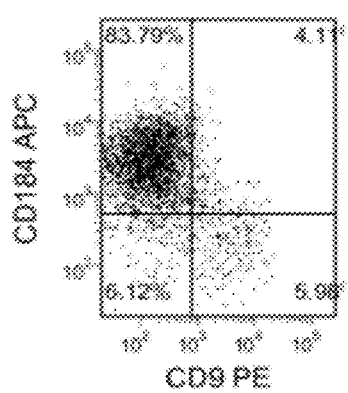
Figure 33D:
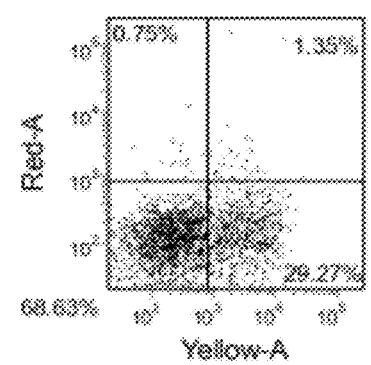
Figure 33E:
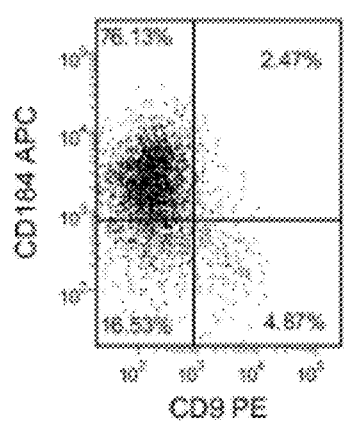
Figure 33F:
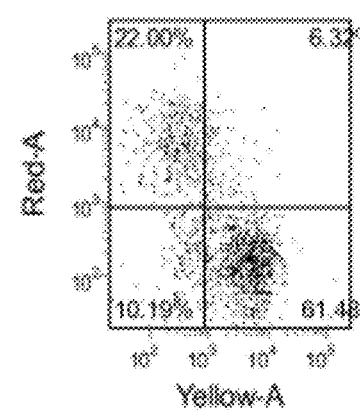

FIGS. 33A-33F depict the expression of CXCR4 by FACS for the embryonic stem cell line H9 at passage 53. Data was obtained 5 days post treatment. Cells were treated with the following conditions: FIG. 33A: 100 ng/ml activin A for all five days plus 20 ng/ml of Wnt-3a for the first two days and 25 ng/ml BMP-4 for days 3-5; FIG. 33B: 100 ng/ml activin A for all five days plus 20 ng/ml of Wnt-3a for the first two days; FIG. 33C: 100 ng/ml activin A for all five days plus 100 nM of GSK-3B inhibitor IX for the first two days; FIG. 33D: 20 ng/ml Wnt-3a+25 ng/ml BMP-4 for all five days; FIG. 33E: 100 ng/ml activin A for all five days plus 20 ng/ml of Wnt-3a+100 nm GSK-3B inhibitor IX for the first two days, and FIG. 33F: 100 ng/ml activin A+25 ng/ml BMP-4 for all five days. For all figures, the X-axis represents expression of CD9 and the Y-axis represents expression of CXCR4 (CD184).

Figure 34A:
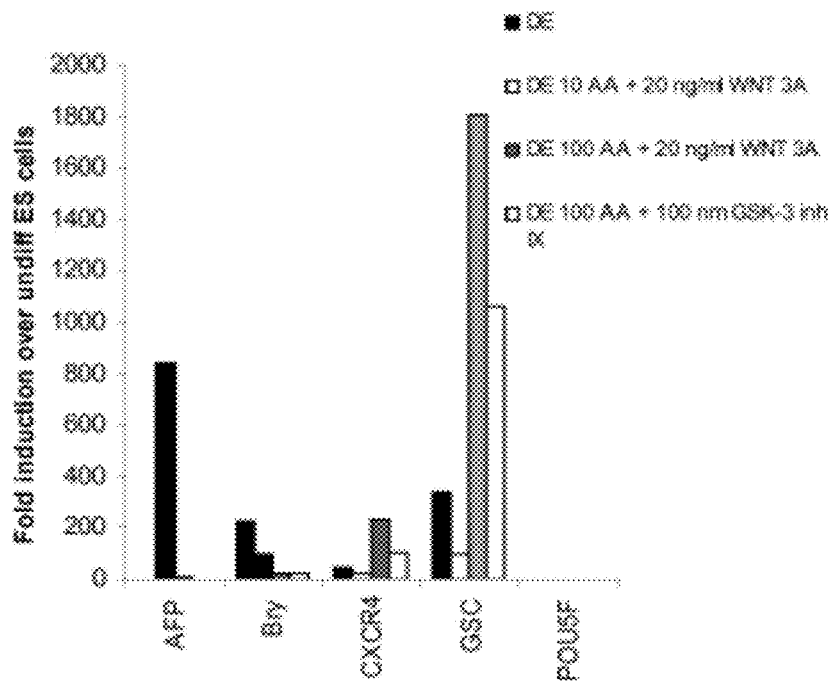
Figure 34B:
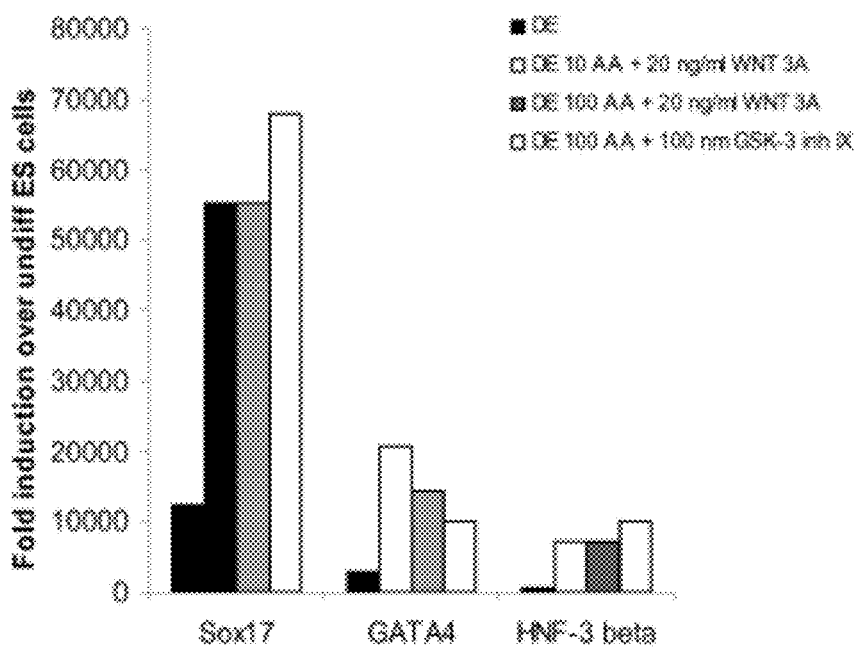

FIGS. 34A-34B depict the gene expression of definitive endoderm markers, as determined by real-time PCR for cultures of the human embryonic stem cell line H1 at passage 46, treated with 10 or 100 ng/ml of activin A plus 20 ng/ml of Wnt-3a or 100 NM GSK-3B inhibitor: FIG. 34A: expression of AFP, Bry, CXCR4, GSC, and POU5F (Oct-4) and FIG. 34B: SOX-17, HNF-3B, and GATA4. Results are expressed as fold increase over untreated cells.

Figure 35A:
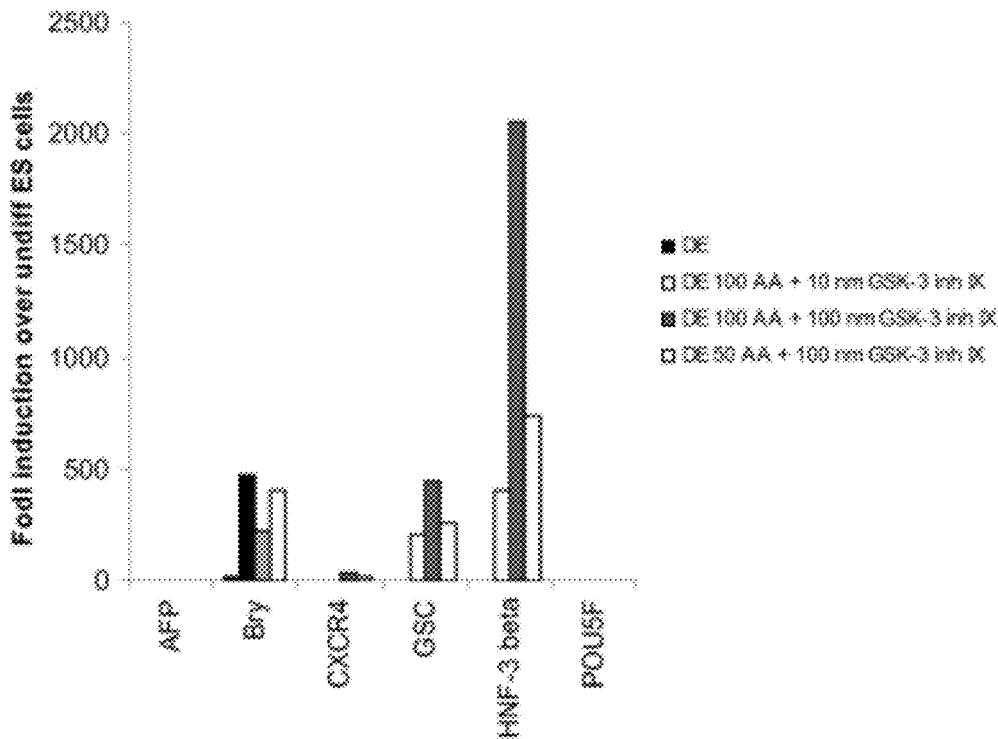
Figure 35B:
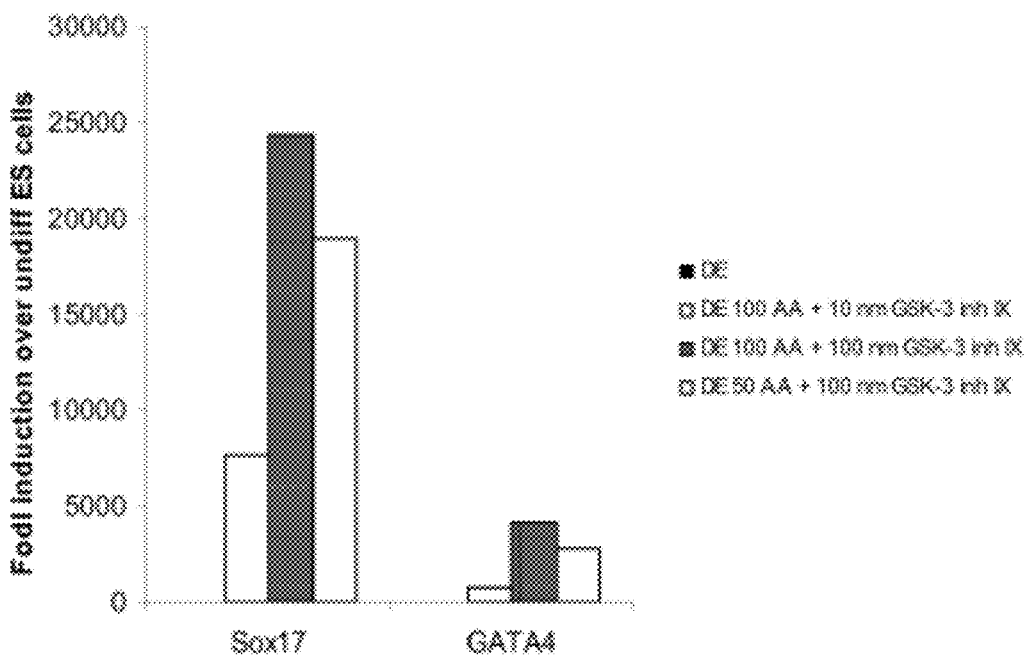

FIGS. 35A-35B depict the gene expression of definitive endoderm markers, as determined by real-time PCR for cultures of the human embryonic stem cell line H9 at passage 49, treated with 50 or 100 ng/ml of activin A plus 10 or 100 nM GSK-3B inhibitor: FIG. 35A: expression of AFP, Bry, CXCR4, GSC, HNF-3B, and POU5F (Oct-4) and FIG. 35B: SOX-17 and GATA4. Results are expressed as fold increase over untreated cells.

Figure 36A:
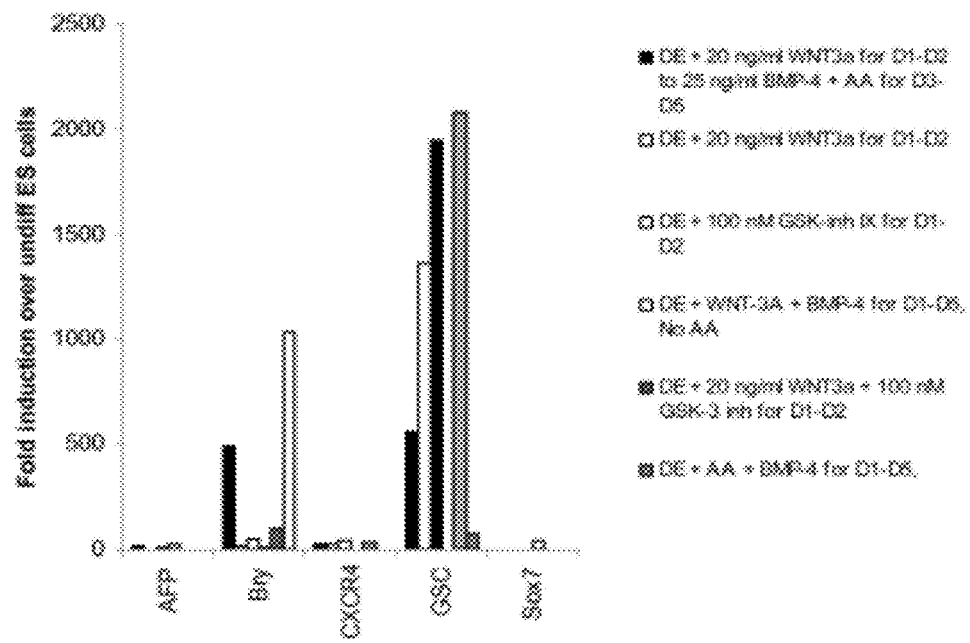
Figure 36B:
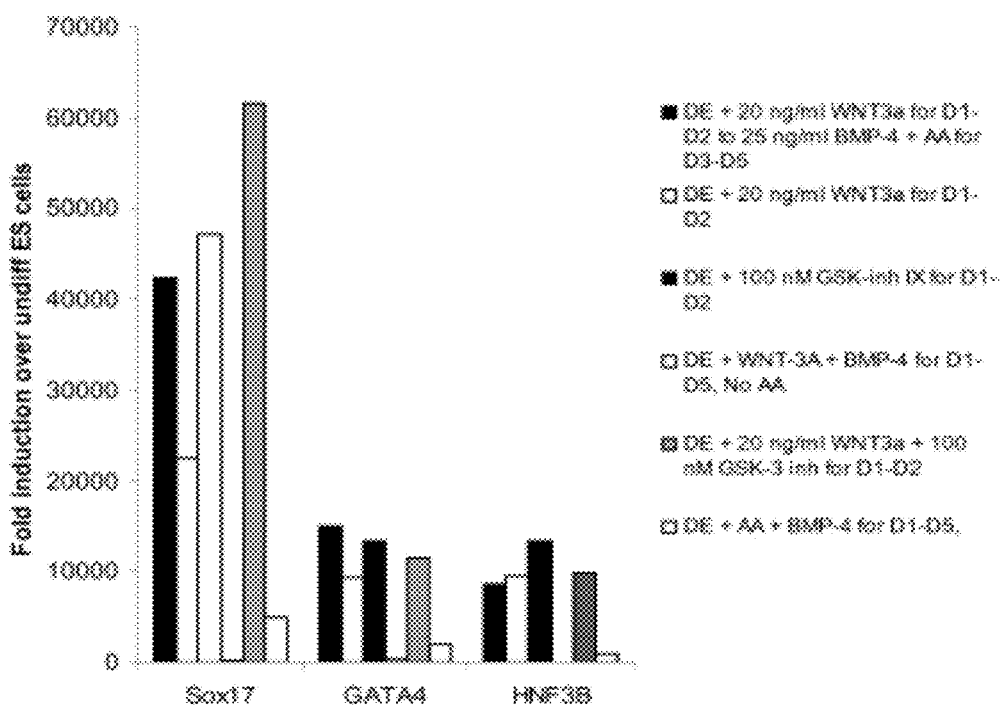

FIGS. 36A-36B depict the gene expression of definitive endoderm markers, as determined by real-time PCR for cultures of the human embryonic stem cell line H9 at passage 53, treated with combinations of activin A, Wnt-3a, GSK-3 inhibitor, and BMP-4, for five days: FIG. 36A: expression of AFP, Bry, CXCR4, GSC, HNF-3B, and SOX7 and FIG. 36B: SOX-17, HNF-3B and GATA4.

Figure 37:
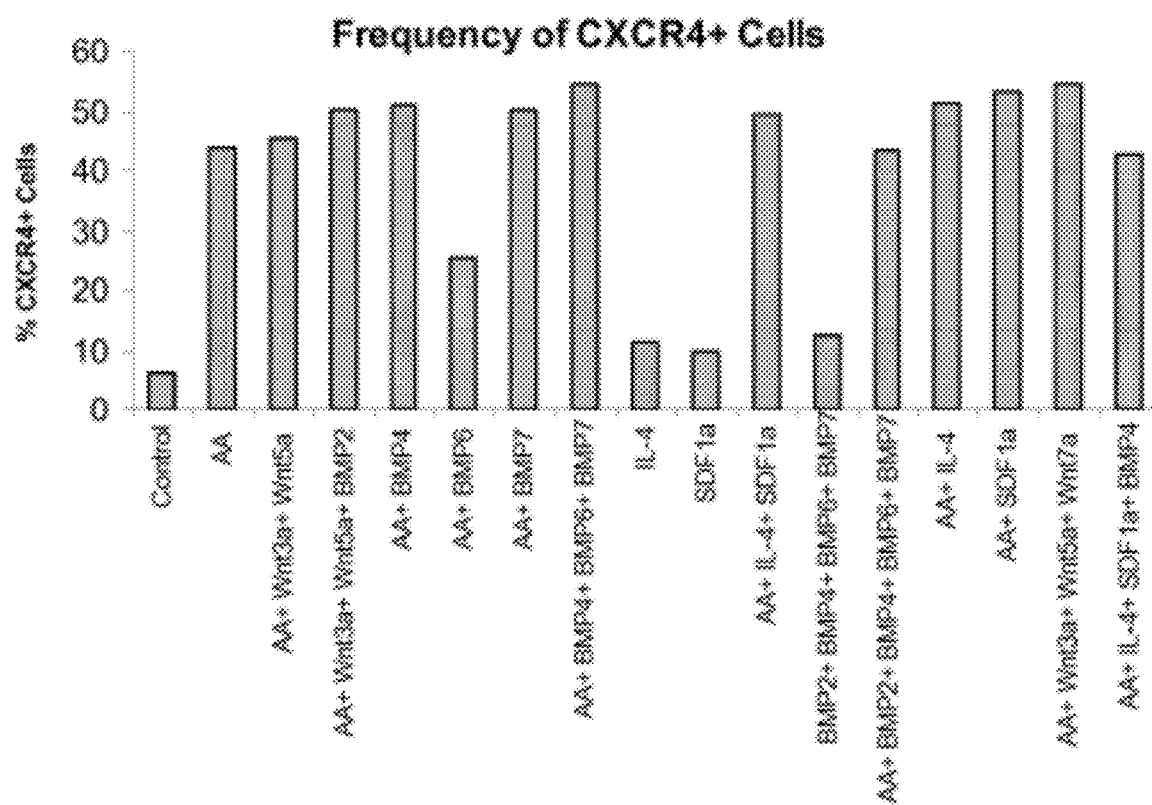

FIG. 37 depicts the percentage of CXCR4 expression, determined by FACS, in cultures of the human embryonic stem cell line H9, treated with the conditions listed in Example 22.

Figure 38A:
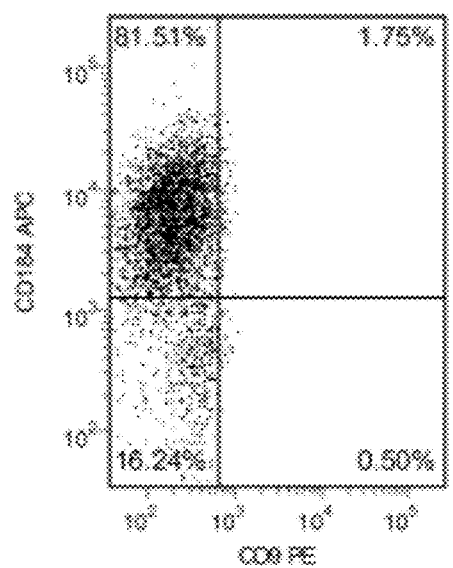
Figure 38B:
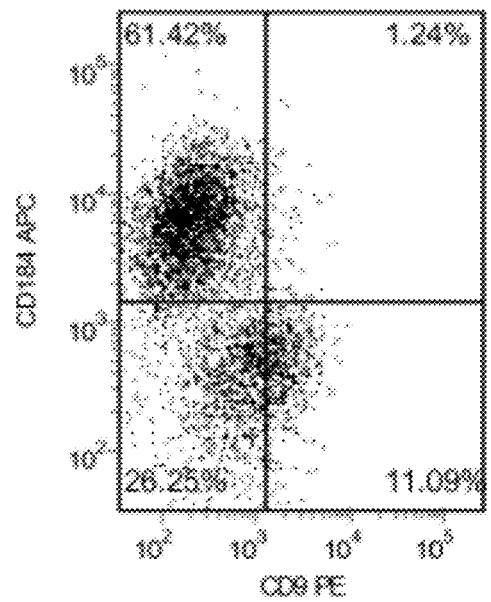

FIGS. 38A-38B depict the expression of definitive endoderm markers as determined by FACS in cultures of the human embryonic stem cell line H9, cultured on fibronectin (FIG. 38A) or MATRIGEL™ (FIG. 38B).

Figure 39:
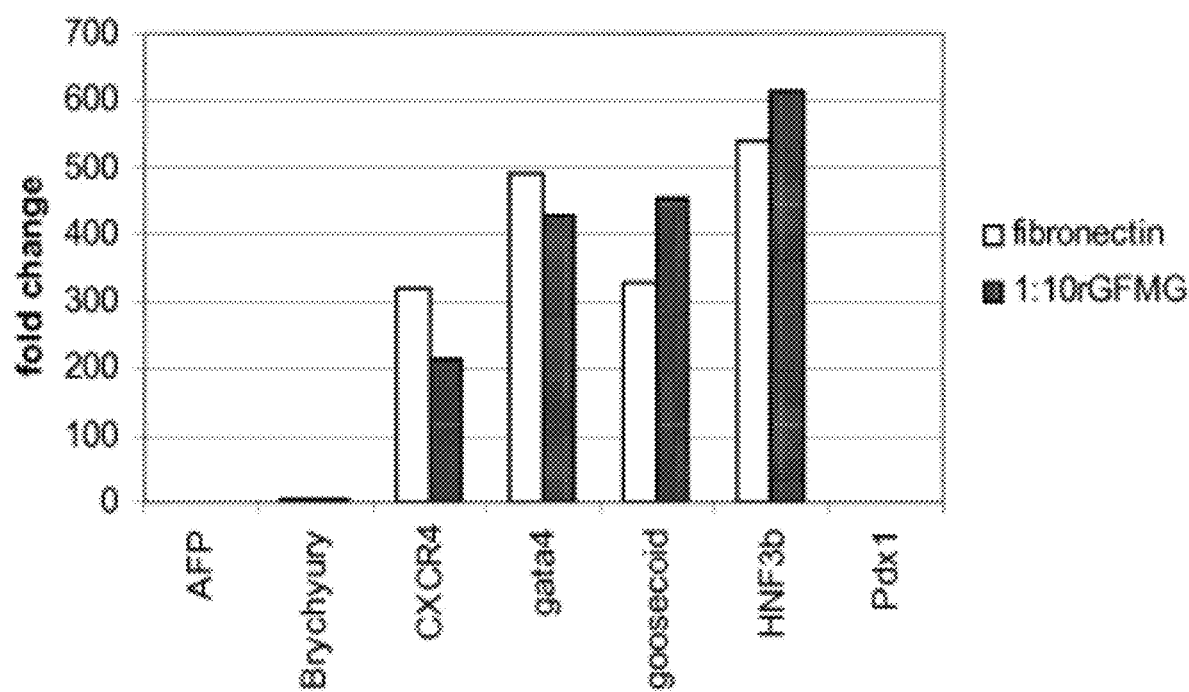

FIG. 39 depicts the expression of definitive endoderm markers as determined by real-time PCR in cultures of the human embryonic stem cell line H9, cultured on fibronectin (□) or a 1:10 dilution of growth factor reduced MATRIGEL (■).

Figure 40:
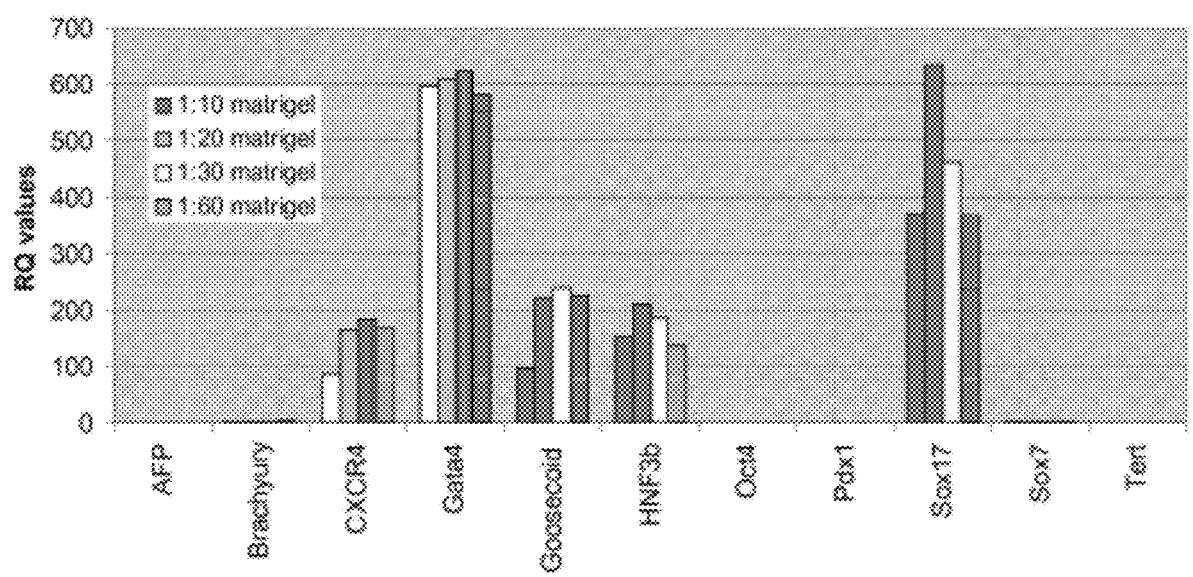

FIG. 40 depicts the effect of various concentrations of MATRIGEL in the presence of low serum, 100 ng/ml of activin A and 20 ng/ml of Wnt-3a on differentiating human embryonic stem cells into definitive endoderm. Cells were treated according to the methods disclosed in Example 4. Results shown are the expression levels of the genes indicated, as determined by real-time PCR.

Figure 41A:
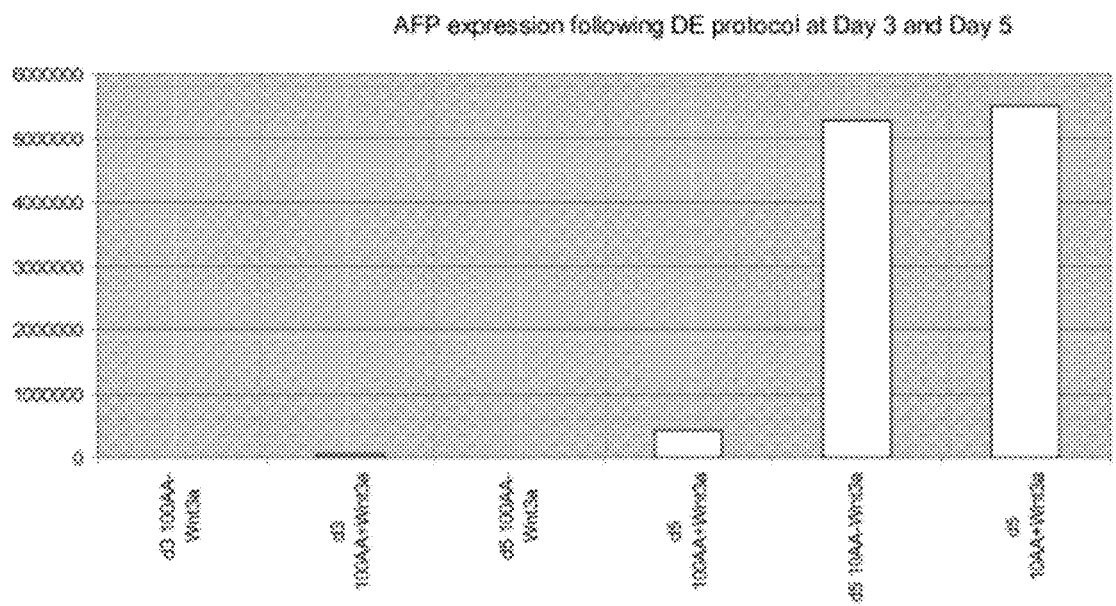
Figure 41B:
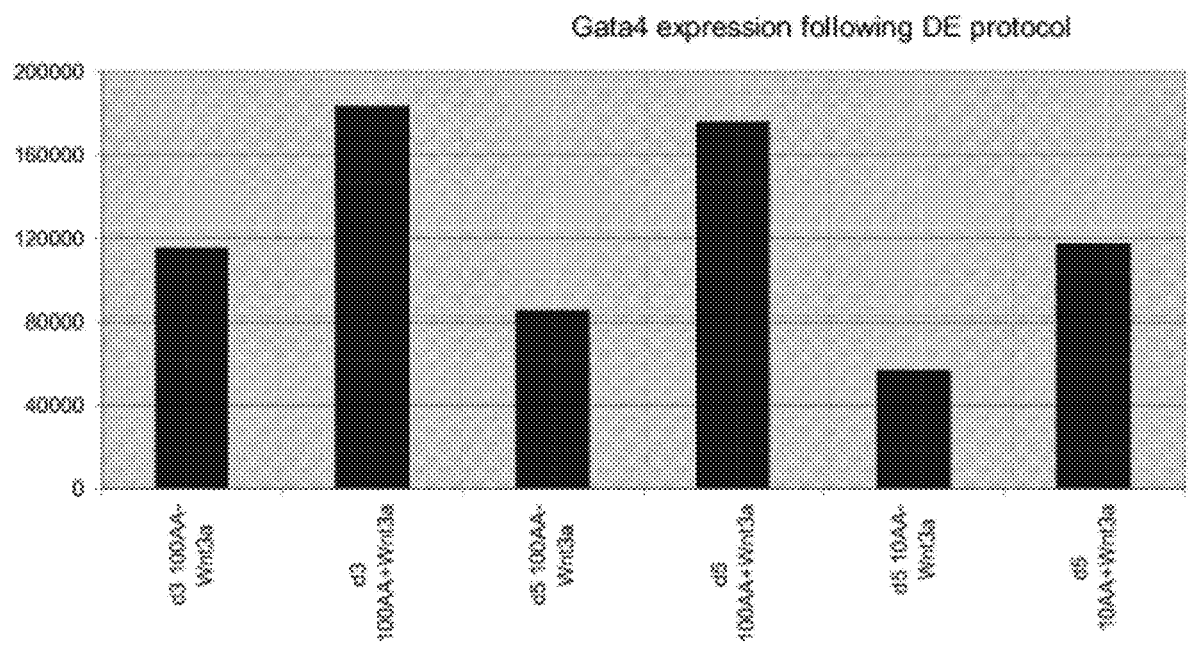
Figure 41C:
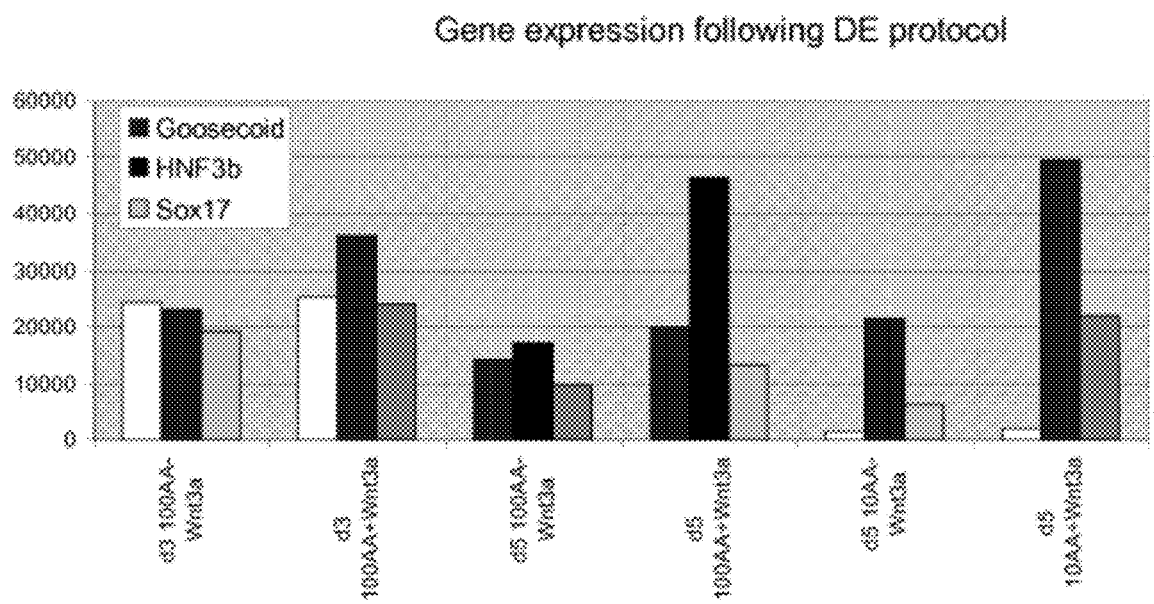
Figure 41D:
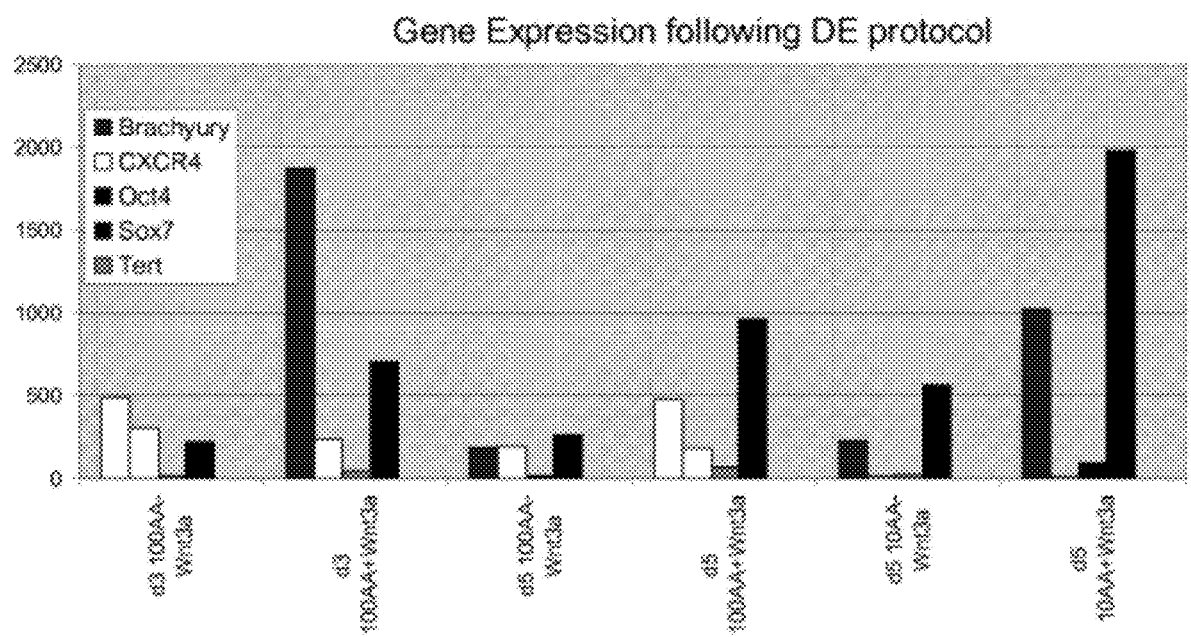
Figures 41E, 41F:
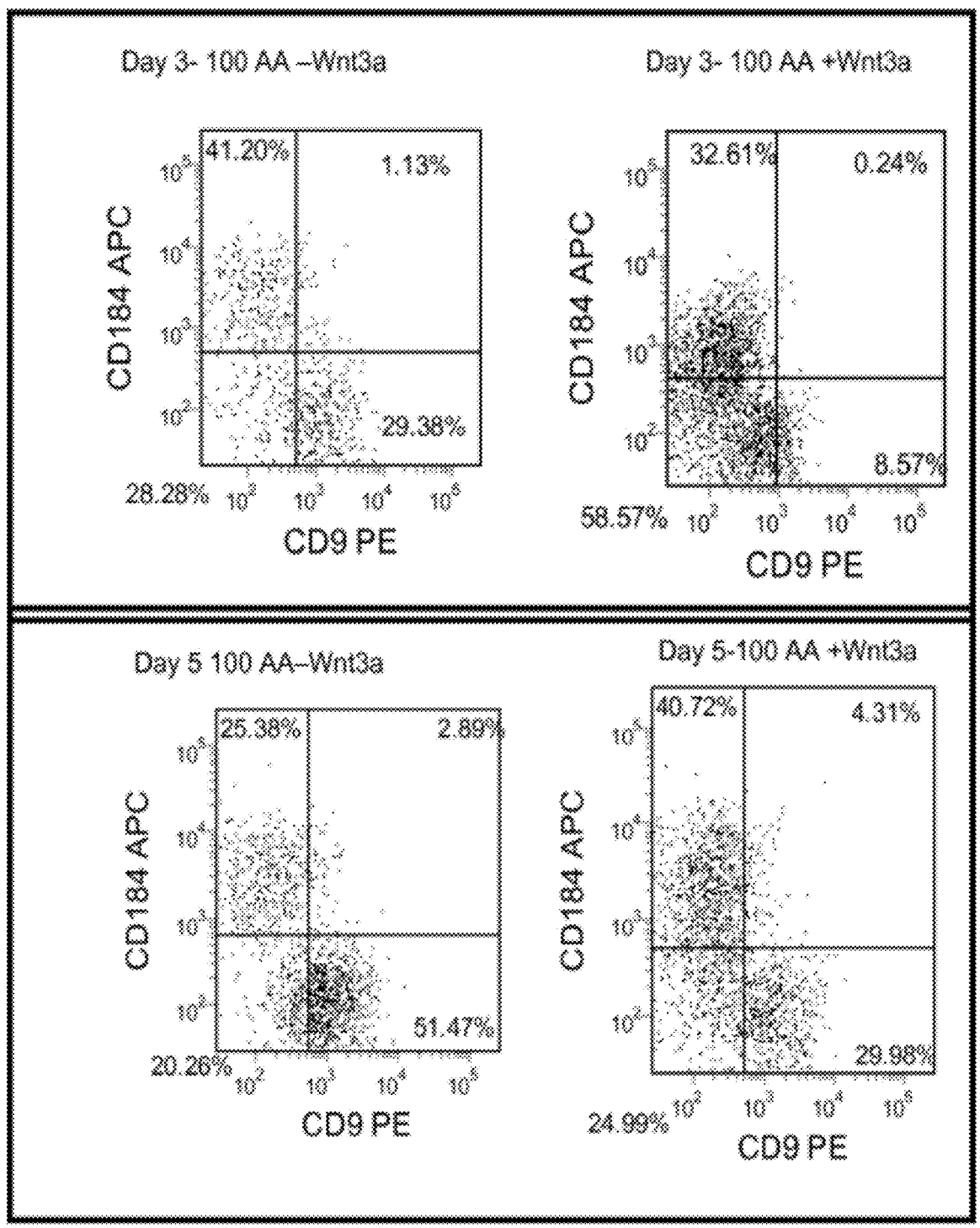
Figure 41G:
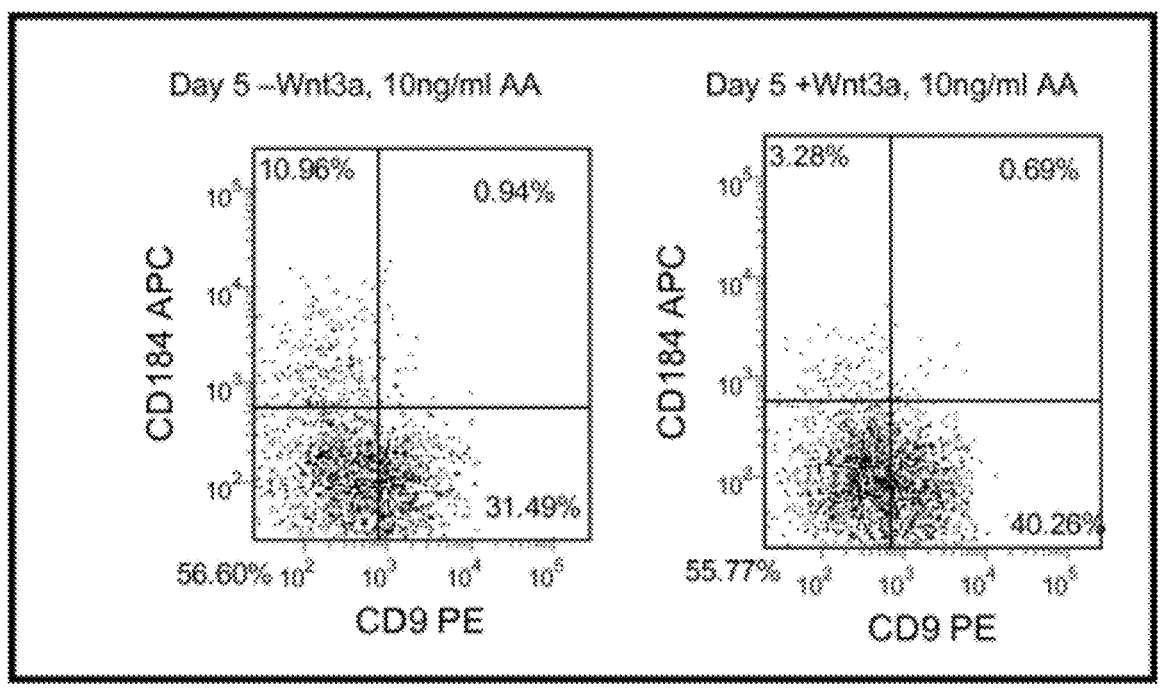

FIGS. 41A-41G depict the role of Wnt-3a in definitive endoderm formation by human embryonic stem cells maintained on MATRIGEL, but differentiated on mouse embryonic fibroblasts. FIGS. 41A-41D show real-time PCR data for the genes indicated. FIGS. 41E-41G show FACS data for the conditions indicated.

Figure 42:
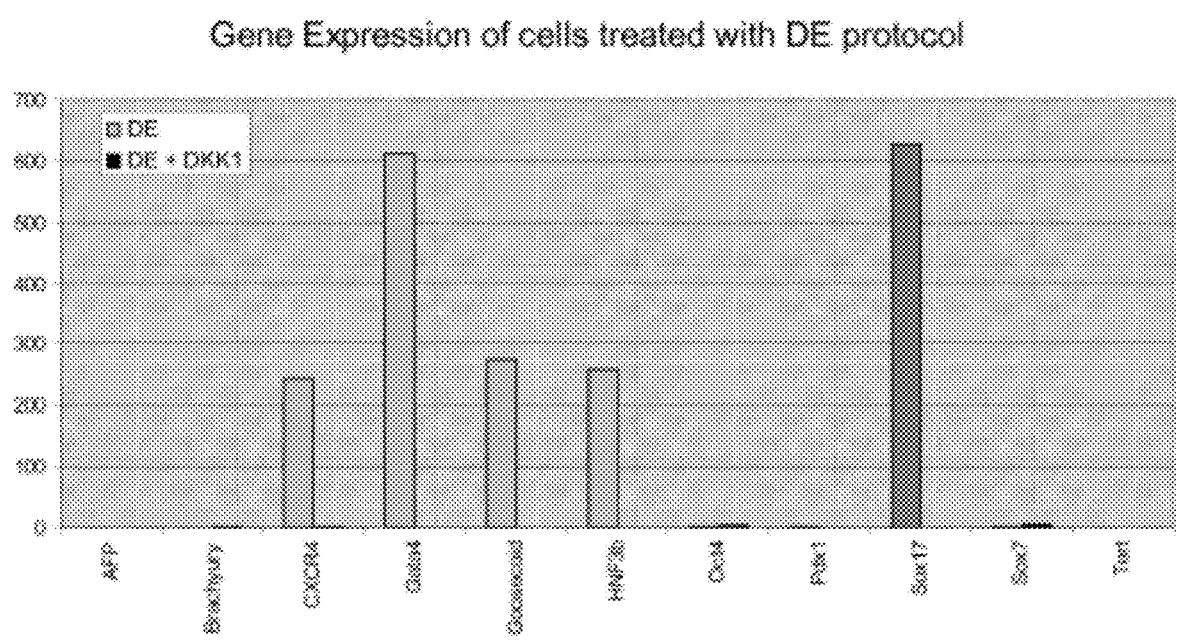

FIG. 42 shows the differentiation of human embryonic stem cells cultured on tissue culture substrate coated with MATRIGEL™ to definitive endoderm following treatment with the Wnt Inhibitor DKK-1. Results shown are the expression of the genes indicated, as determined by real-time PCR in H9 cells treated according to the methods disclosed in Example 4 in the presence of 20 ng/ml of Wnt-3A plus 100 ng/ml of DKK1 (DE+DKK1), or in the absence of DKK1 (DE).

Figure 43A:
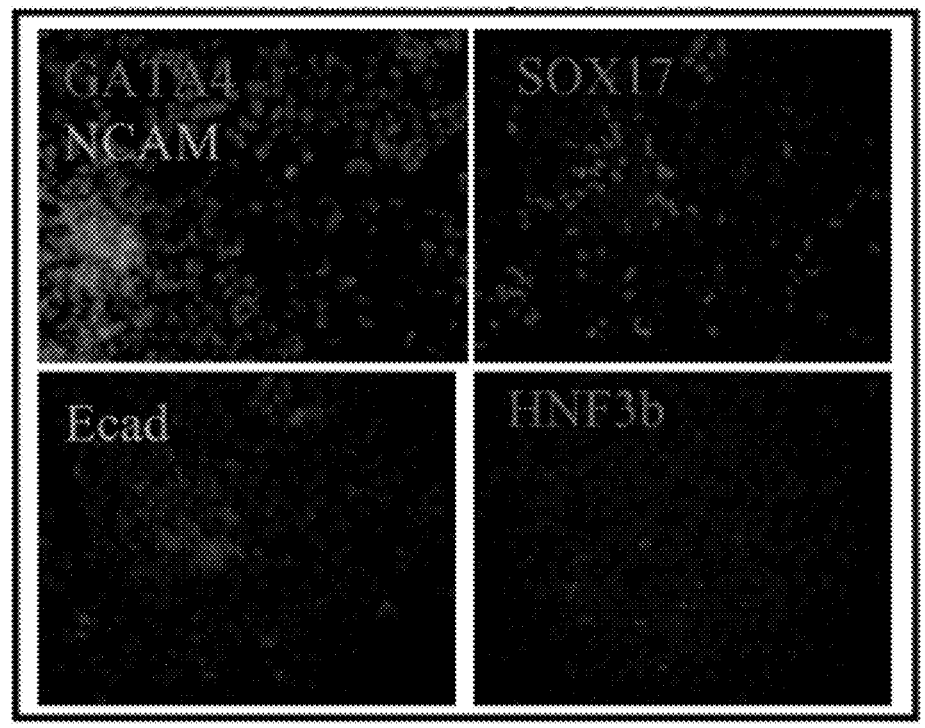
Figure 43B:
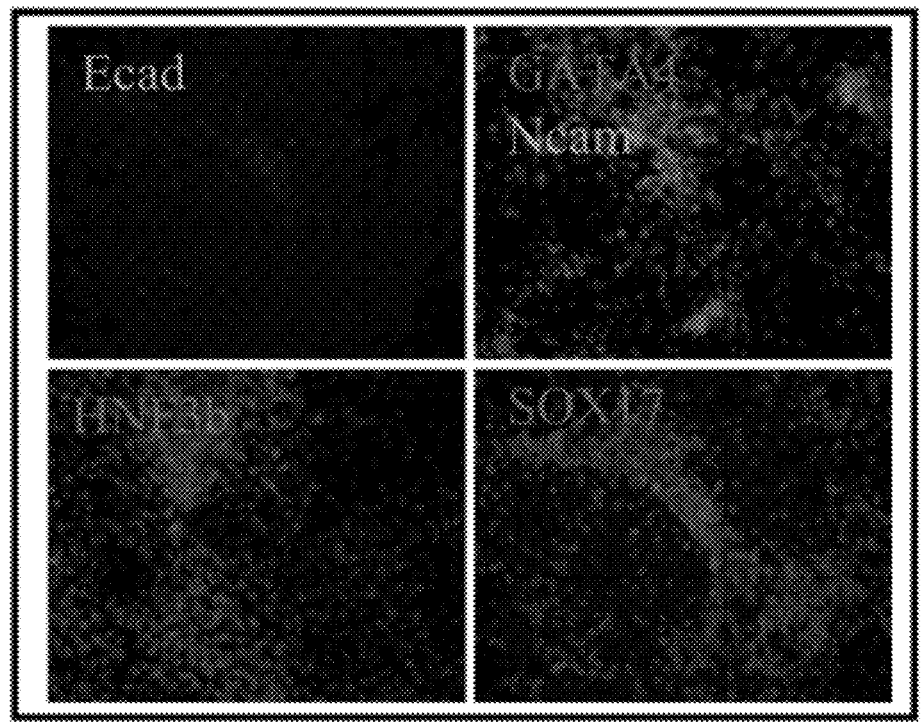
Figure 44A:
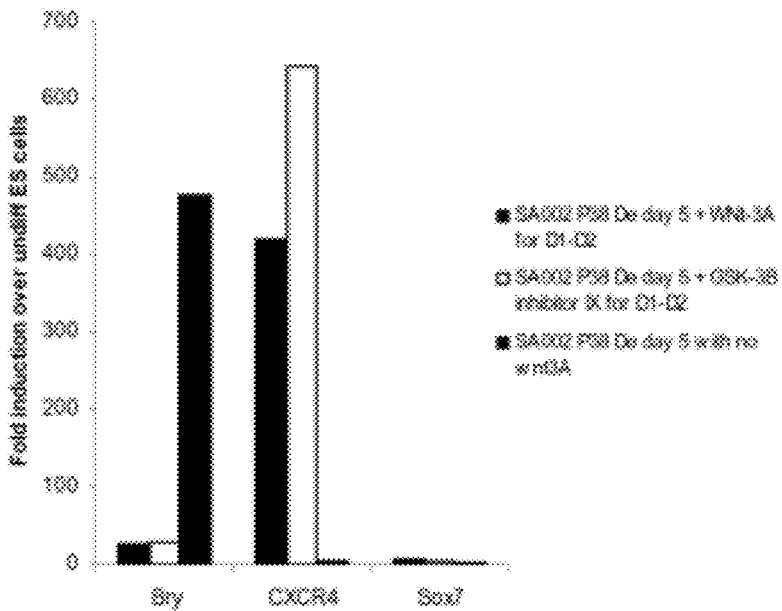
Figure 44B:
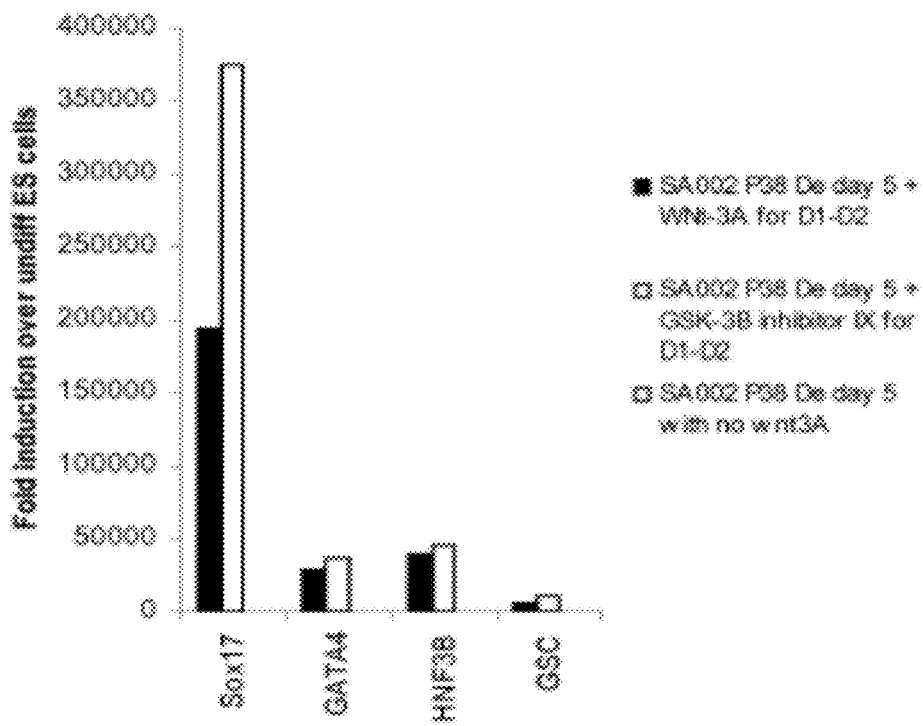

FIGS. 43A-43B show immunofluorescence staining of definitive endoderm markers in cultures of the human embryonic stem cell line H9 cultured on tissue culture substrate coated with MATRIGEL and differentiated in low serum plus 100 ng/ml of activin-A without (FIG. 43A), or with (FIG. 43B) 20 ng/ml of Wnt-3a. Ecad=E-cadherin, NCAM=N-cadherin, FIGS. 44A-44B show the differentiation of the human embryonic stem cell line SA002 at passage 38 into definitive endoderm. Cells were treated for five days with the conditions indicated and gene expression was determined by real-time PCR, for the genes indicated in the figures.

Figure 45A:
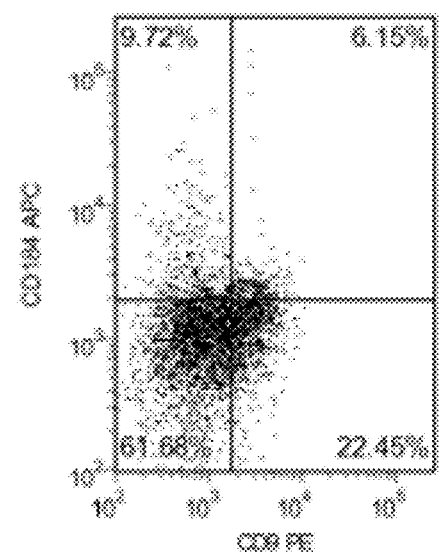
Figure 45B:
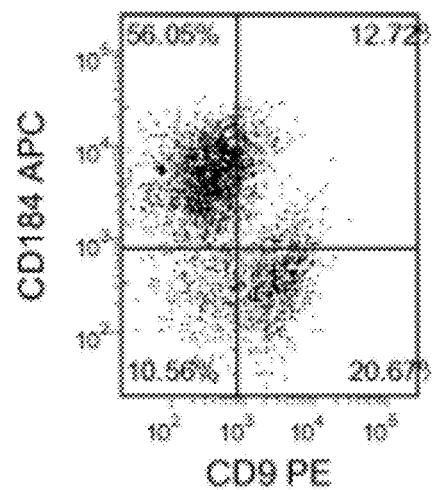
Figure 45C:
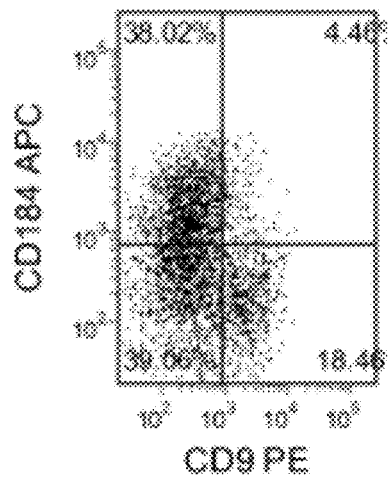

FIGS. 45A-45C show the expression of CXCR4 by FACS in the human embryonic stem cell line SA002 at passage 38, following treatment with 100 ng/ml activin A treatment (FIG. 45A), 100 ng/ml activin A+20 ng/ml Wnt-3a (FIG. 45B), or 100 ng/ml activin A+100 nM GSK-3B inhibitor IX (FIG. 45C). Cells were treated for five days.

Figure 46A:
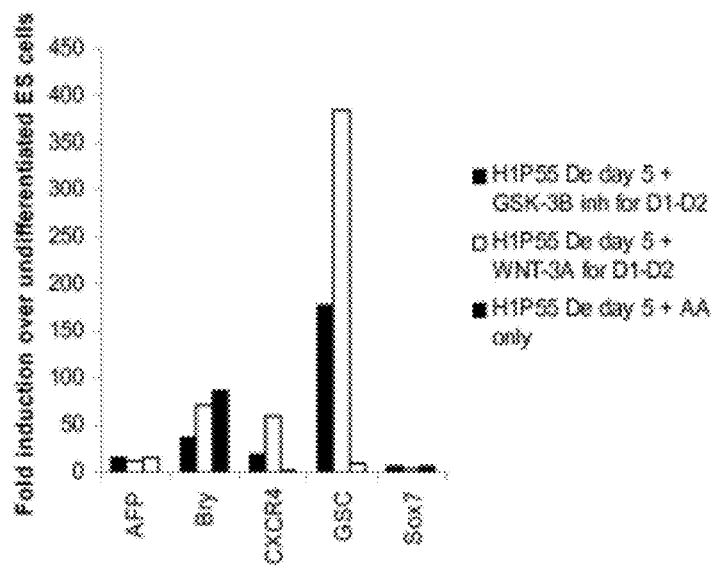
Figure 46B:
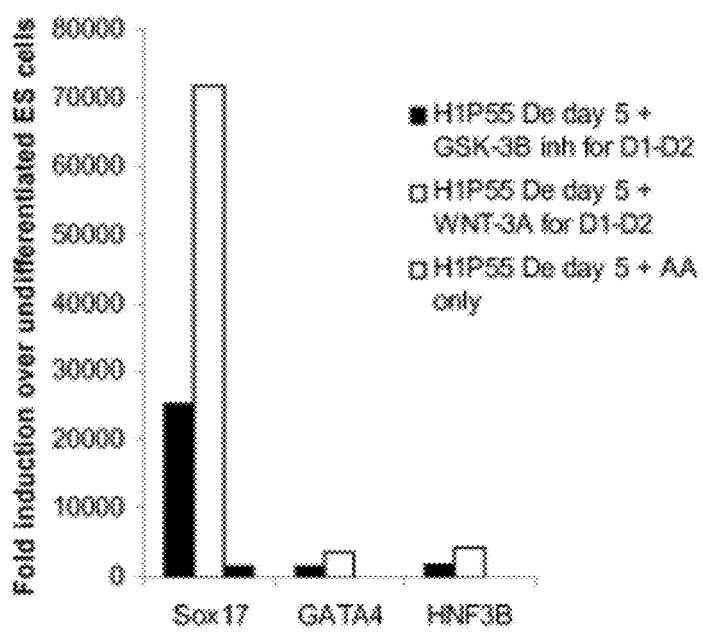

FIGS. 46A-46B show the differentiation of the human embryonic stem cell line H1 at passage 55 into definitive endoderm on tissue culture substrate coated with human serum. Cells were treated with the conditions indicated and gene expression was determined by real-time PCR, for the genes indicated in the figures.

Figure 47A:
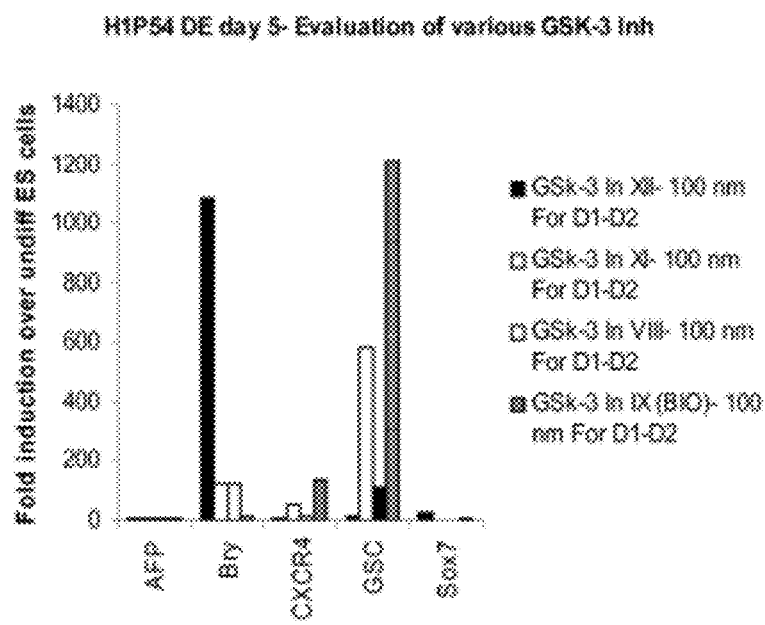
Figure 47B:
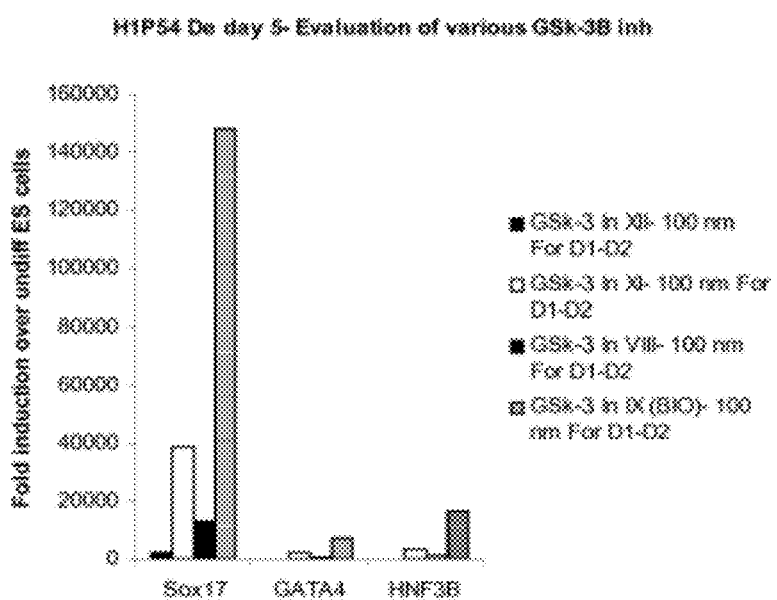
Figure 48A:
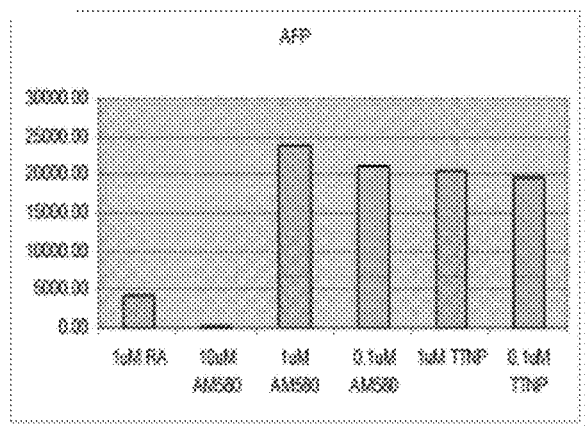
Figure 48B:
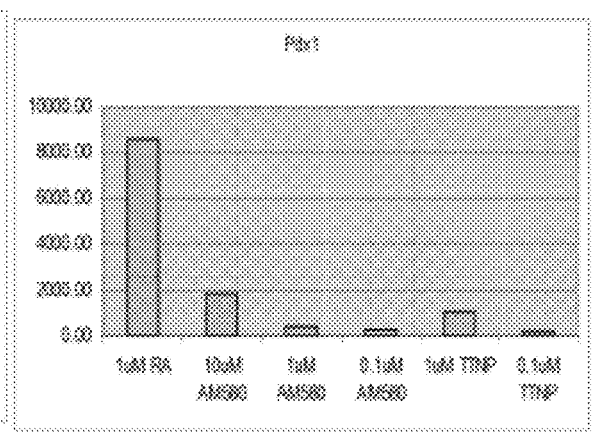
Figure 48C:
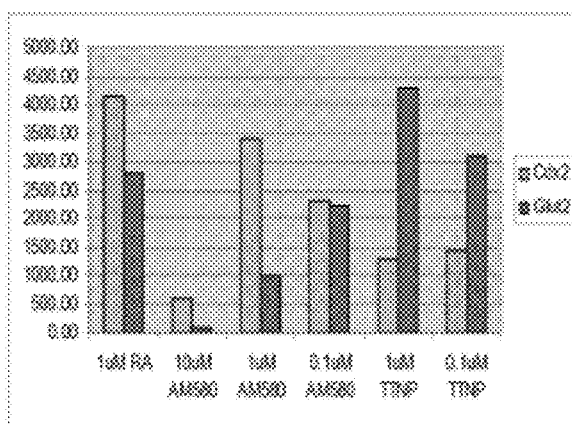
Figure 48D:
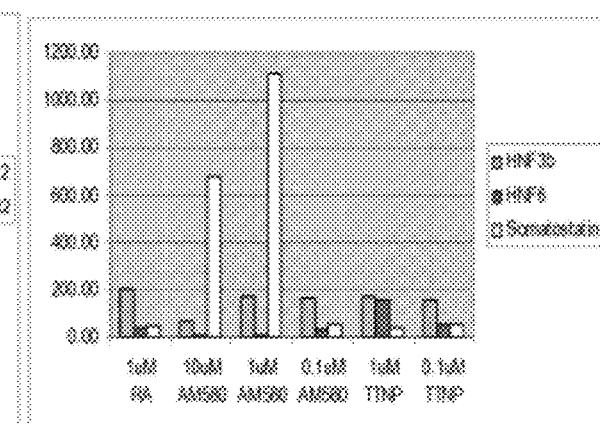

FIGS. 47A-47B show the differentiation of cultures of the human embryonic stem cell line H1 at P54, on tissue culture substrate coated with MATRIGEL™ to definitive endoderm. The effects of various GSK-B inhibitors were tested following a five-day DE protocol. The following GSK-3B inhibitors were evaluated at 100 nM for the first two days of treatment: GSK-3B VIII, IX, XI, and XII.

FIGS. 48A-48D show the expression of AFP (FIG. 48A), Pdx-1 (FIG. 48B), Cdx-2 and Glut-2 (FIG. 48C) and HNF-3beta, HNF-6 and somatostatin (FIG. 48D) in cultures of the human embryonic stem cell line H9 at passage 49, cultured and treated according to the methods disclosed in Example 4 in the presence of 20 ng/ml of Wnt-3a for the first two days of treatment. Following the treatment, the cells were treated for three additional days with 2% FBS plus 1 μM retinoic acid, 0.1 to 1 μM TTNPB (4-[(E)-2-(5,6,7,8-Tetrahydro-5,5,8,8-tetramethyl-2-naphthalenyl)-1-propenyl]benzoic acid Arotinoid acid), or 0.1-10 μM AM-580 (4-[(5,6,7,8-Tetrahydro-5,5,8,8-tetramethyl-2-naphthalenyl)carboxamido] benzoic acid). The cells were next treated for three additional days in 2% FBS plus 20 ng/ml of bFGF.

Figure 49A:
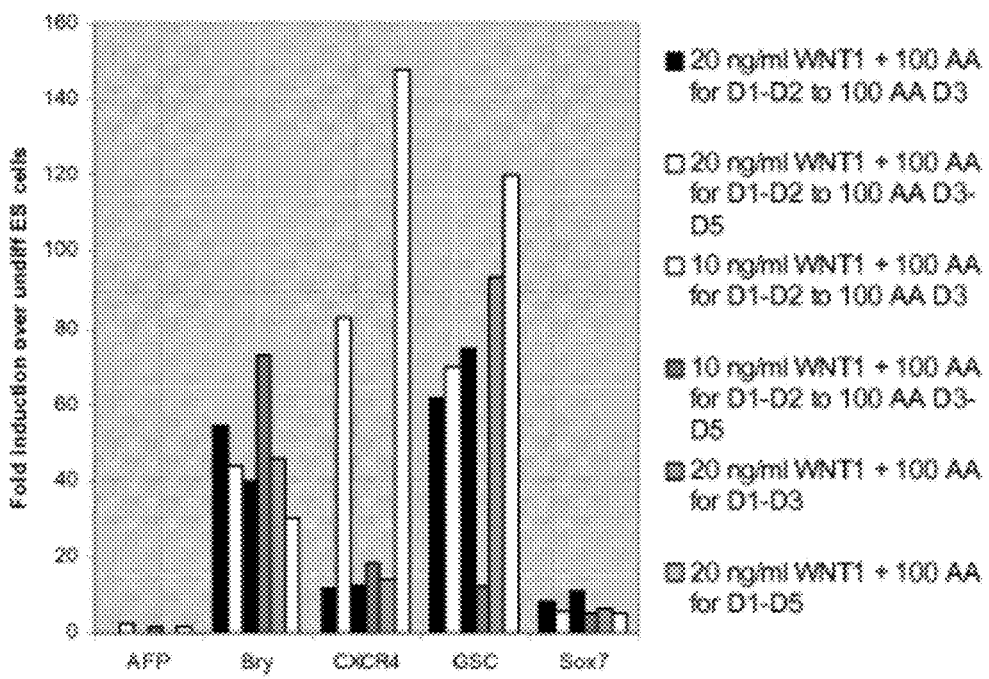
Figure 49B:
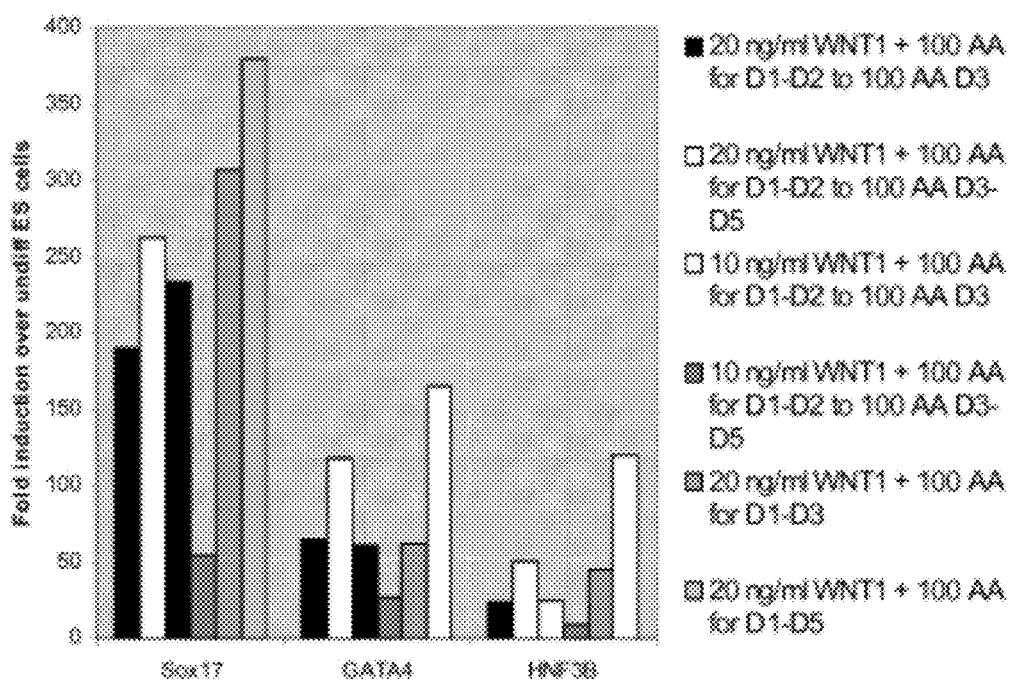

FIGS. 49A-49B show the real-time PCR results of the expression of the definitive endoderm markers indicated in FIGS. 49A and 49B. in cultures of the human embryonic stem cell line H1 treated with activin A and Wnt-1 for the times and concentrations indicated.

Figure 50A:
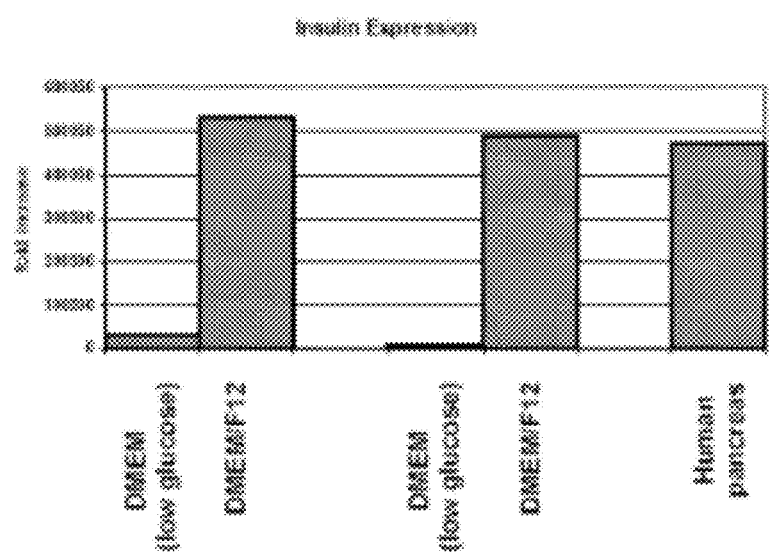
Figure 50B:
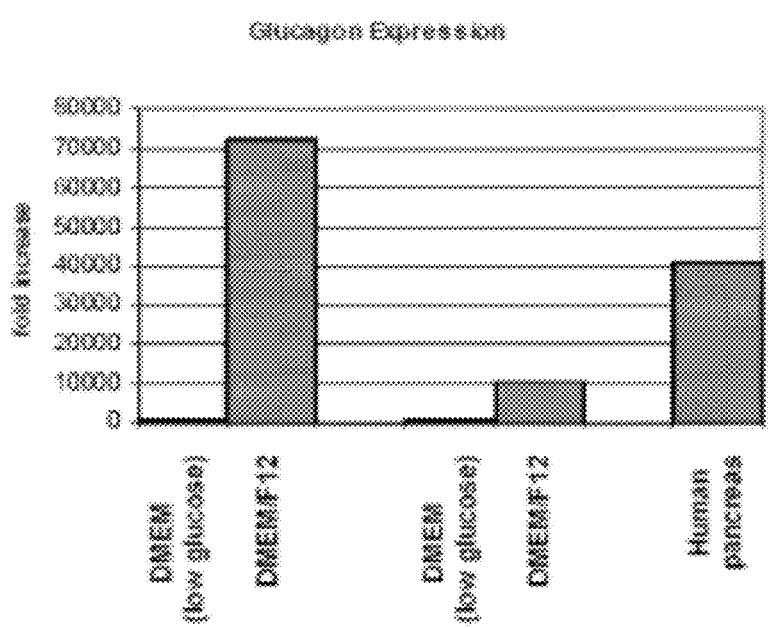

FIGS. 50A-50B depict insulin (FIG. 50A) and glucagon (FIG. 50B) mRNA expression in cultures of pancreatic endocrine cells, formed from the treatment of pancreatic endoderm cells in DMEM/F12 or DMEM-low glucose. Data shown are results observed from two separate experiments.

Figure 51A:
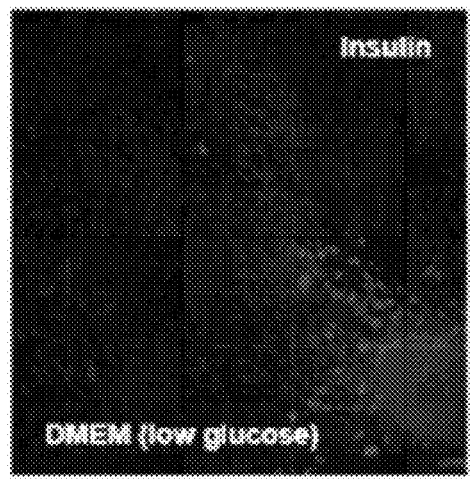
Figure 51B:
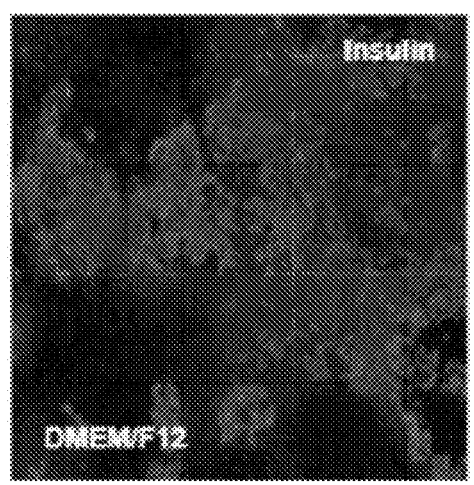
Figure 51C:
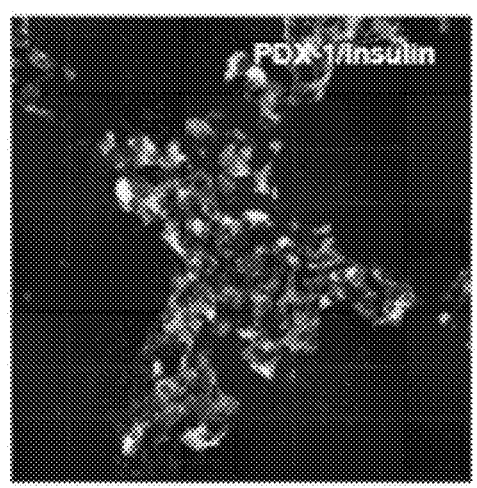

FIGS. 51A-51C depict insulin expression as determined by immunocytochemistry in cells treated in DMDM-low glucose (FIG. 51A), DMEM/F12 (FIG. 51B). FIG. 51C shows the co-staining of PDX-1 and insulin.

FIGS. 52A-52G show the effect of glucose concentration on gene expression in pancreatic endocrine cells derived from the human embryonic stem cell line H9. Genes are identified in the figures.

Figure 53:
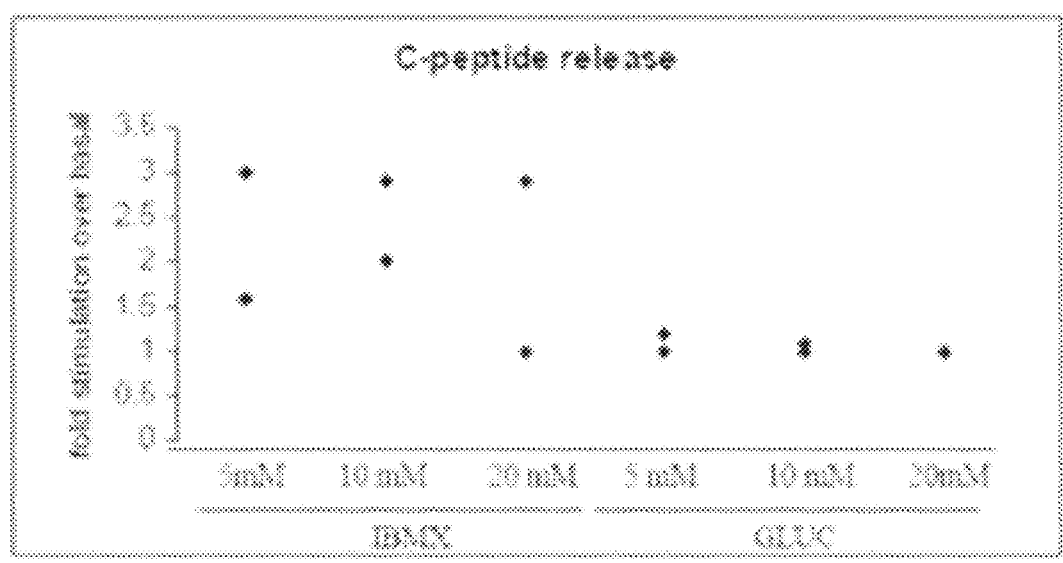

FIG. 53 shows c-peptide release from pancreatic endocrine cells formed in 2, 10 and 20 mM glucose. Cells were stimulated with IBMX or 20 mM glucose.

DETAILED DESCRIPTION

For clarity of disclosure, and not by way of limitation, the detailed description of the invention is divided into the following subsections that describe or illustrate certain features, embodiments or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

Various terms are used to describe cells in culture. "Maintenance" refers generally to cells placed in a growth medium under conditions that facilitate cell growth and/or division, which may or may not result in a larger population of the cells. "Passaging" refers to the process of removing the cells from one culture vessel and placing them in a second culture vessel under conditions that facilitate cell growth and/or division.

A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passages depends on many factors, including but not limited to the seeding density, substrate, medium, growth conditions, and time between passaging.

"β-cell lineage" refer to cells with positive gene expression for the transcription factor PDX-1 and at least one of the following transcription factors: NGN-3, Nkx2.2, Nkx6.1, NeuroD, Is1-1, HNF-3 beta, MAFA, Pax4, and Pax6. Cells expressing markers characteristic of the β cell lineage include β cells.

"Cells expressing markers characteristic of the definitive endoderm lineage" as used herein refer to cells expressing at least one of the following markers: SOX-17, GATA-4, HNF-3 beta, GSC, Cer1, Nodal, FGF8, Brachyury, Mixlike homeobox protein, FGF4 CD48, eomesodermin (EOMES), DKK4, FGF17, GATA-6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage" as used herein refer to cells expressing at least one of the following markers: PDX-1, HNF-1beta, HNF-3beta, PTF-1 alpha, HNF-6, or HB9. Cells expressing markers characteristic of the pancreatic endoderm lineage include pancreatic endoderm cells.

"Cells expressing markers characteristic of the pancreatic endocrine lineage" as used herein refer to cells expressing at least one of the following markers: NGN-3, NeuroD, Islet-1, PDX-1, NKX6.1, Pax-4, Ngn-3, or PTF-1 alpha. Cells expressing markers characteristic of the pancreatic endocrine lineage include pancreatic endocrine cells, pancreatic hormone expressing cells, and pancreatic hormone secreting cells, and cells of the β-cell lineage.

"Definitive endoderm" as used herein refers to cells which bear the characteristics of cells arising from the epiblast during gastrulation and which form the gastrointestinal tract and its derivatives. Definitive endoderm cells express the following markers: CXCR4, HNF-3 beta, GATA-4, SOX-17, Cerberus, OTX2, goosecoid, c-Kit, CD99, and Mix11.

"Extraembryonic endoderm" as used herein refers to a population of cells expressing at least one of the following markers: SOX-7, AFP, and SPARC.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell" as used herein refers to a cell expressing at least one of the following markers: CD48, eomesodermin (EOMES), SOX-17, DKK4, HNF-3 beta, GSC, FGF17, GATA-6.

"Pancreatic endocrine cell" or "pancreatic hormone expressing cell" as used herein refers to a cell capable of expressing at least one of the following hormones: insulin, glucagon, somatostatin, pancreatic polypeptide and ghrelin.

"Pancreatic hormone secreting cell" as used herein refers to a cell capable of secreting at least one of the following hormones: insulin, glucagon, somatostatin, and pancreatic polypeptide.

"Pre-primitive streak cell" as used herein refers to a cell expressing at least one of the following markers: Nodal, or FGF8.

"Primitive streak cell" as used herein refers to a cell expressing at least one of the following markers: Brachyury, Mix-like homeobox protein, or FGF4.

Isolation, Expansion and Culture of Pluripotent Stem Cells

Characterization of Pluripotent Stem Cells

Pluripotent stem cells may express one or more of the stage-specific embryonic antigens (S SEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame CA) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, GA).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

For example, Reubinoff et al (Nature Biotechnology 18: 399-404 (2000)) and Thompson et al (Science 6 Nov. 1998: Vol. 282. no. 5391, pp. 1145-1147) disclose the culture of pluripotent stem cell lines from human blastocysts using a mouse embryonic fibroblast feeder cell layer.

Richards et al, (Stem Cells 21: 546-556, 2003) evaluated a panel of 11 different human adult, fetal and neonatal feeder cell layers for their ability to support human pluripotent stem cell culture. Richards et al, states: "human embryonic stem cell lines cultured on adult skin fibroblast feeders retain human embryonic stem cell morphology and remain pluripotent".

US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al (Stem Cells 23: 1221-1227, 2005) discloses methods for the long-term growth of human pluripotent stem cells on feeder cell layers derived from human embryonic stem cells.

In another example, Stojkovic et al (Stem Cells 2005 23: 306-314, 2005) disclose a feeder cell system derived from the spontaneous differentiation of human embryonic stem cells.

In a further example, Miyamoto et al (Stem Cells 22: 433-440, 2004) disclose a source of feeder cells obtained from human placenta.

Amit et al (Biol. Reprod 68: 2150-2156, 2003) discloses a feeder cell layer derived from human foreskin.

In another example, Inzunza et al (Stem Cells 23: 544-549, 2005) disclose a feeder cell layer from human postnatal foreskin fibroblasts.

U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

In another example, WO2005014799 discloses conditioned medium for the maintenance, proliferation and differentiation of mammalian cells. WO2005014799 states: "The culture medium produced in accordance with the present invention is conditioned by the cell secretion activity of murine cells, in particular, those differentiated and immortalized transgenic hepatocytes, named MMH (Met Murine Hepatocyte)."

In another example, Xu et al (Stem Cells 22: 972-980, 2004) discloses conditioned medium obtained from human embryonic stem cell derivatives that have been genetically modified to over express human telomerase reverse transcriptase.

In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al (BioReprod DOI:10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGFβ) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, a suitable culture substrate is MATRIGEL® (Becton Dickenson). MATRIGEL® is a soluble preparation from Engelbreth-Holm Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Differentiation of Pluripotent Stem Cells in to Cells Expressing Markers Characteristic of the Pancreatic Endocrine Lineage Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FoxD3, Connexin43, Connexin45, Oct4, Sox2, Nanog, hTERT, UTF-1, ZFP42, SSEA-3, SSEA-4, Tra1-60, Tra1-81.

Markers characteristic of the definitive endoderm lineage are selected from the group consisting of SOX-17, GATA4, Hnf-3beta, GSC, Cer1, Noda1, FGF8, Brachyury, Mix-like homeobox protein, FGF4 CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of Pdx1, HNF-1beta, PTF1a, HNF-6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of the pancreatic endocrine lineage are selected from the group consisting of NGN-3, NeuroD, Islet-1, Pdx-1, NKX6.1, Pax-4, Ngn-3, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In one aspect of the present invention, the pancreatic endocrine cell is a cell expressing markers characteristic of the β cell lineage. A cell expressing markers characteristic of the β cell lineage expresses Pdx1 and at least one of the following transcription factors: NGN-3, Nkx2.2, Nkx6.1, NeuroD, Is1-1, HNF-3 beta, MAFA, Pax4, and Pax6. In one aspect of the present invention, a cell expressing markers characteristic of the β cell lineage is a β cell.

Formation of Cells Expressing Markers Characteristic of the Definitive Endoderm Lineage Pluripotent stem cells may be differentiated into cells expressing markers characteristic of the definitive endoderm lineage by any method in the art or by any method proposed in this invention.

For example, pluripotent stem cells may be differentiated into cells expressing markers characteristic of the definitive endoderm lineage according to the methods disclosed in D'Amour et al, Nature Biotechnology 23, 1534-1541 (2005).

For example, pluripotent stem cells may be differentiated into cells expressing markers characteristic of the definitive endoderm lineage according to the methods disclosed in Shinozaki et al, Development 131, 1651-1662 (2004).

For example, pluripotent stem cells may be differentiated into cells expressing markers characteristic of the definitive endoderm lineage according to the methods disclosed in McLean et al, Stem Cells 25, 29-38 (2007).

For example, pluripotent stem cells may be differentiated into cells expressing markers characteristic of the definitive endoderm lineage according to the methods disclosed in D'Amour et al, Nature Biotechnology 24, 1392-1401 (2006).

For example, pluripotent stem cells may be differentiated into cells expressing markers characteristic of the definitive endoderm lineage by culturing the pluripotent stem cells in medium containing activin A in the absence of serum, then culturing the cells with activin A and serum, and then culturing the cells with activin A and serum of a different concentration. An example of this method is disclosed in Nature Biotechnology 23, 1534-1541 (2005).

For example, pluripotent stem cells may be differentiated into cells expressing markers characteristic of the definitive endoderm lineage by culturing the pluripotent stem cells in medium containing activin A in the absence of serum, then culturing the cells with activin A with serum of another concentration. An example of this method is disclosed in D'Amour et al, Nature Biotechnology, 2005.

For example, pluripotent stem cells may be differentiated into cells expressing markers characteristic of the definitive endoderm lineage by culturing the pluripotent stem cells in medium containing activin A and a Wnt ligand in the absence of serum, then removing the Wnt ligand and culturing the cells with activin A with serum. An example of this method is disclosed in Nature Biotechnology 24, 1392-1401 (2006).

In one aspect of the present invention, pluripotent stem cells may be differentiated into cells expressing markers characteristic of the definitive endoderm lineage by plating the pluripotent stem cells on a tissue culture substrate coated with an extracellular matrix, then culturing the pluripotent stem cells with activin A and a Wnt ligand in a first culture medium containing serum for a period of time, and then culturing the pluripotent stem cells with activin A in a second culture medium containing a greater concentration of serum for about another period of time.

The concentration of serum in the first culture medium disclosed above may be from about zero to about 0.5 percent, and the culture time may be from about one to about three days. The concentration of serum in the second culture medium disclosed above may be from about 0.5 percent to about two percent, and the culture time may be from about one to about four days.

In an alternate embodiment of the present invention, pluripotent stem cells may be differentiated into cells expressing markers characteristic of the definitive endoderm lineage by plating the pluripotent stem cells on a tissue culture substrate coated with an extracellular matrix, then culturing the pluripotent stem cells with activin A and a Wnt ligand in a first culture medium containing serum for about a period of time, and then culturing the pluripotent stem cells with activin A and a Wnt ligand in a second culture medium containing a greater concentration of serum for another period of time.

The concentration of serum in the first culture medium disclosed above may be from about zero to about 0.5 percent, and the culture time may be from about one to about three days. The concentration of serum in the second culture medium disclosed above may be from about 0.5 percent to about two percent, and the culture time may be from about one to about four days.

In one embodiment, the present invention provides a method for differentiating pluripotent stem cells expressing markers characteristic of the definitive endoderm lineage, comprising the steps of:
a. Plating the pluripotent stem cells on a tissue culture substrate coated with an extracellular matrix, and
b. Culturing the pluripotent stem cells with activin A and a Wnt ligand.

Culturing the pluripotent stem cells with activin A and a Wnt ligand may be performed in a single culture medium. Alternatively, culturing the pluripotent stem cells with activin A and a Wnt ligand may be performed separately or together in more than one culture media. In one embodiment, culturing the pluripotent stem cells with activin A and a Wnt ligand is performed in two culture media.

Extracellular Matrix

In one aspect of the present invention, the pluripotent stem cells are cultured and differentiated on a tissue culture substrate coated with an extracellular matrix. The extracellular matrix may be a solubilized basement membrane preparation extracted from mouse sarcoma cells (which is sold by BD Biosciences under the trade name MATRIGEL). Alternatively, the extracellular matrix may be growth factor-reduced MATRIGEL. Alternatively, the extracellular matrix may fibronectin. In an alternate embodiment, the pluripotent stem cells are cultured and differentiated on tissue culture substrate coated with human serum.

The extracellular matrix may be diluted prior to coating the tissue culture substrate. Examples of suitable methods for diluting the extracellular matrix and for coating the tissue culture substrate may be found in Kleinman, H. K., et al., Biochemistry 25:312 (1986), and Hadley, M. A., et al., J. Cell. Biol. 101:1511 (1985).

In one embodiment, the extracellular matrix is MATRIGEL. In one embodiment, the tissue culture substrate is coated with MATRIGEL at a 1:10 dilution. In an alternate embodiment, the tissue culture substrate is coated with MATRIGEL at a 1:15 dilution. In an alternate embodiment, the tissue culture substrate is coated with MATRIGEL at a 1:30 dilution. In an alternate embodiment, the tissue culture substrate is coated with MATRIGEL at a 1:60 dilution.

In one embodiment, the extracellular matrix is growth factor-reduced MATRIGEL. In one embodiment, the tissue culture substrate is coated with growth factor-reduced MATRIGEL at a 1:10 dilution. In an alternate embodiment, the tissue culture substrate is coated with growth factor-reduced MATRIGEL at a 1:15 dilution. In an alternate embodiment, the tissue culture substrate is coated with growth factor-reduced MATRIGEL at a 1:30 dilution. In an alternate embodiment, the tissue culture substrate is coated with growth factor-reduced MATRIGEL at a 1:60 dilution.

Differentiation of Pluripotent Stem Cells into Cells Expressing Markers Characteristic of the Definitive Endoderm Lineage on an Extracellular Matrix, Using a Single Culture Medium When a single culture medium is used, it should contain sufficiently low concentrations of certain factors to allow the differentiation of pluripotent stem cells to definitive endoderm, such as, for example insulin and IGF (as disclosed in WO2006020919). This may be achieved by lowing the serum concentration, or alternatively, by using chemically defined media that lacks insulin and IGF. Examples of chemically defined media are disclosed in Wiles et al (Exp Cell Res. 1999 Feb. 25; 247(1): 241-8).

The culture medium may have a serum concentration in the range of about 0% to about 10%. In an alternate embodiment, the concentration may be in the range of about 0% to about 5%. In an alternate embodiment, the concentration may be in the range of about 0% to about 2%. In an alternate embodiment, the concentration may be about 2%.

The time of culturing with activin A and a Wnt ligand may range from about 1 day to about 7 days. In an alternate embodiment, the time of culturing may range from about 1 day to about 3 days. In an alternate embodiment, the time of culturing may be about 3 days.

Activin A may be used at any concentration suitable to cause differentiation of the pluripotent stem cells. The concentration maybe from about 1 pg/ml to about 100 µg/ml. In an alternate embodiment, the concentration may be about 1 pg/ml to about 1 µg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The choice of the Wnt ligand may be optimized to improve the efficiency of the differentiation process. The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The Wnt ligand may be at a concentration of about 1 ng/ml to about 1000 ng/ml. In an alternate embodiment, the concentration may be about 10 ng/ml to about 100 ng/ml.

The single culture medium may also contain a GSK-3B inhibitor. The GSK-3B inhibitor may be selected from the group consisting of GSK-3B inhibitor IX and GSK-3B inhibitor XI. In one embodiment, the GSK-3B inhibitor is GSK-3B inhibitor IX.

When culturing pluripotent stem cells with a GSK-3B inhibitor, the concentration of the GSK-3B inhibitor may be from about 1 nM to about 1000 nM. In an alternate embodiment, the pluripotent stem cells are cultured with the GSK-3B inhibitor at a concentration of about 10 nM to about 100 nM.

The single culture medium may also contain at least one other additional factor that may enhance the formation of cells expressing markers characteristic of the definitive endoderm lineage from pluripotent stem cells. Alternatively, the at least one other additional factor may enhance the proliferation of the ells expressing markers characteristic of the definitive endoderm lineage formed by the methods of the present invention. Further, the at least one other additional factor may enhance the ability of the cells expressing markers characteristic of the definitive endoderm lineage formed by the methods of the present invention to form other cell types, or improve the efficiency of any other additional differentiation steps.

The at least one additional factor may be, for example, nicotinamide, members of the TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valproic acid, trichostatin A, sodium butyrate, hepatocyte growth factor (HGF), sphingosine 1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), intestinal cell lines such as, for example, FHs 74 (ATCC No: CCL-241), and primary or transformed endothelial cells.

Differentiation of Pluripotent Stem Cells into Cells Expressing Markers Characteristic of the Definitive Endoderm Lineage on an Extracellular Matrix, Using Two Culture Media Differentiation of pluripotent stem cells into cells of a definitive endoderm lineage may be accomplished by culturing the pluripotent stem cells with activin A and a Wnt ligand using two culture media. Thus, the differentiation of the pluripotent stem cells may be accomplished as follows:
a. Plating the pluripotent stem cells on a tissue culture substrate coated with an extracellular matrix,
b. Culturing the pluripotent stem cells with activin A and a Wnt ligand in a first culture medium, and
c. Culturing the pluripotent stem cells with activin A in a second culture medium.

The first culture medium may contain serum at a low concentration, and the second culture medium may contain serum at a higher concentration than the first culture medium.

The second culture medium may contain a Wnt ligand.

First Culture Medium: The first culture medium should contain sufficiently low concentrations of certain factors to allow the differentiation of pluripotent stem cells into cells expressing markers characteristic of the definitive endoderm lineage, such as, for example insulin and IGF (as disclosed in WO2006020919). This may be achieved by lowing the serum concentration, or alternatively, by using chemically defined media that lacks insulin and IGF. Examples of chemically defined media are disclosed in Wiles et al (Exp Cell Res. 1999 Feb. 25; 247(1):241-8).

In the first culture medium there may be a lower concentration of serum, relative to the second culture medium. Increasing the serum concentration in the second culture medium increases the survival of the cells, or, alternatively, may enhance the proliferation of the cells. The serum concentration of the first medium may be in the range of about 0% to about 10%. Alternatively, the serum concentration of the first medium may be in the range of about 0% to about 2%. Alternatively, the serum concentration of the first medium may be in the range of about 0% to about 1%. Alternatively, the serum concentration of the first medium may be about 0.5%.

When culturing the pluripotent stem cells with activin A and a Wnt ligand using at least two culture media, the time of culturing in the first culture medium may range from about 1 day to about 3 days.

Activin A may be used at any concentration suitable to cause differentiation of the pluripotent stem cells. The concentration maybe from about 1 pg/ml to about 100 μg/ml. In an alternate embodiment, the concentration may be about 1 pg/ml to about 1 μg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The choice of the Wnt ligand may be optimized to improve the efficiency of the differentiation process. The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The Wnt ligand may be at a concentration of about 1 ng/ml to about 1000 ng/ml. In an alternate embodiment, the concentration may be about 10 ng/ml to about 100 ng/ml.

The first culture medium may also contain a GSK-3B inhibitor. The GSK-3B inhibitor may be added to the first culture medium, to the second culture medium, or to both the first and second culture media.

The GSK-3B inhibitor may be selected from the group consisting of GSK-3B inhibitor IX and GSK-3B inhibitor XI. In one embodiment, the GSK-3B inhibitor is GSK-3B inhibitor IX.

When culturing pluripotent stem cells with a GSK-3B inhibitor, the concentration of the GSK-3B inhibitor may be from about 1 nM to about 1000 nM. In an alternate embodiment, the pluripotent stem cells are cultured with the GSK-3B inhibitor at a concentration of about 10 nM to about 100 nM.

The first culture medium may also contain at least one other additional factor that may enhance the formation of cells expressing markers characteristic of the definitive endoderm lineage from pluripotent stem cells. Alternatively, the at least one other additional factor may enhance the proliferation of the cells expressing markers characteristic of the definitive endoderm lineage formed by the methods of the present invention. Further, the at least one other additional factor may enhance the ability of the cells expressing markers characteristic of the definitive endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valproic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Second Culture Medium: The second culture medium should contain certain factors, such as, for example, insulin and IGF (as disclosed in WO2006020919), at a sufficient concentration to promote the survival of the cultured cells. This may be achieved by increasing the serum concentration, or, alternatively, by using chemically defined media where the concentrations of insulin and IGF are increased relative to the first culture medium. Examples of chemically defined media are disclosed in Wiles et al (Exp Cell Res. 1999 Feb. 25; 247(1):241-8).

In a second culture medium having higher concentrations of serum, the serum concentration of the second culture medium may be in the range about 0.5% to about 10%. Alternatively, the serum concentration of the second culture medium may be in the range of about 0.5% to about 5%. Alternatively, the serum concentration of the second culture medium may be in the range of about 0.5% to about 2%. Alternatively, the serum concentration of the second culture medium may be about 2%. When culturing pluripotent stem cells with the second culture medium, the time of culturing may range from about 1 day to about 4 days.

Similar to the first culture medium, Activin A may be used at any concentration suitable to cause differentiation of the pluripotent stem cells. The concentration maybe from about 1 pg/ml to about 100 µg/ml. In an alternate embodiment, the concentration may be about 1 pg/ml to about 1 µg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The Wnt ligand may be at a concentration of about 1 ng/ml to about 1000 ng/ml. In an alternate embodiment, the concentration may be about 10 ng/ml to about 100 ng/ml.

The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The second culture medium may also contain a GSK-3B inhibitor. The GSK-3B inhibitor may be added to the first culture medium, to the second culture medium, or to both the first and second culture media.

The GSK-3B inhibitor may be selected from the group consisting of GSK-3B inhibitor IX and GSK-3B inhibitor XI. In one embodiment, the GSK-3B inhibitor is GSK-3B inhibitor IX.

When culturing pluripotent stem cells with a GSK-3B inhibitor, the concentration of the GSK-3B inhibitor may be from about 1 nM to about 1000 nM. In an alternate embodiment, the pluripotent stem cells are cultured with the GSK-3B inhibitor at a concentration of about 10 nM to about 100 nM.

Similar to the first culture medium, the second culture medium may also contain at least one other additional factor that may enhance the formation of cells expressing markers characteristic of the definitive endoderm lineage from pluripotent stem cells. Alternatively, the at least one other additional factor may enhance the proliferation of the cells expressing markers characteristic of the definitive endoderm lineage formed by the methods of the present invention. Further, the at least one other additional factor may enhance the ability of the cells expressing markers characteristic of the definitive endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valproic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Differentiation of Cells Expressing Markers Characteristic of the Definitive Endoderm Lineage Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

For example, characteristics of pluripotent stem cells are well known to those skilled in the art, and additional characteristics of pluripotent stem cells continue to be identified. Pluripotent stem cell markers include, for example, the expression of one or more of the following: ABCG2, cripto, FoxD3, Connexin43, Connexin45, Oct4, Sox2, Nanog, hTERT, UTF-1, ZFP42, SSEA-3, SSEA-4, Tra1-60, Tra1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Formation of Cells Expressing Markers Characteristic of the Pancreatic Endoderm Lineage Cells expressing markers characteristic of the definitive endoderm lineage may be differentiated into cells expressing markers characteristic of the pancreatic endoderm lineage by any method in the art or by any method proposed in this invention.

For example, cells expressing markers characteristic of the definitive endoderm lineage may be differentiated into cells expressing markers characteristic of the pancreatic endoderm lineage according to the methods disclosed in D'Amour et al, Nature Biotechnology 24, 1392-1401 (2006).

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006).

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time. That period of time may be from about one to about six days.

In an alternate aspect of the present invention, cells expressing markers characteristic of the definitive endoderm lineage are further differentiated into cells expressing markers characteristic of the pancreatic endoderm lineage, by treating the cells with retinoic acid for a period of time. That period of time maybe from about one to about three days. The retinoic acid is subsequently removed and the cells are treated with at least one fibroblast growth factor for another period of time. That period of time may be from about one to about three days.

In one embodiment, the present invention provides a method for differentiating cells expressing markers characteristic of the definitive endoderm lineage into cells expressing markers characteristic of the pancreatic endoderm lineage, comprising the steps of:
a. Culturing cells expressing markers characteristic of the definitive endoderm lineage, and
b. Treating the cells expressing markers characteristic of the definitive endoderm lineage with retinoic acid and at least one fibroblast growth factor.

Any cell expressing markers characteristic of the definitive endoderm lineage is suitable for differentiating into a cell expressing markers characteristic of the pancreatic endoderm lineage using this method.

In one embodiment, the cells expressing markers characteristic of the definitive endoderm are treated with retinoic acid and at least one fibroblast growth factor for about one to about six days. In one embodiment, the cells expressing markers characteristic of the definitive endoderm are treated with retinoic acid and at least one fibroblast growth factor for about six days.

The at least one fibroblast growth factor is selected from the group consisting of FGF-2, FGF-4 and FGF-10.

Any cell expressing markers characteristic of the definitive endoderm lineage is suitable for differentiating into a cell expressing markers characteristic of the pancreatic endoderm lineage using this method.\

In an alternate embodiment, the present invention provides a method for differentiating cells expressing markers characteristic of the definitive endoderm lineage into cells expressing markers characteristic of the pancreatic endoderm lineage, comprising the steps of:
a. Culturing cells expressing markers characteristic of the definitive endoderm lineage,
b. Treating the cells expressing markers characteristic of the definitive endoderm lineage treating the cells with retinoic acid, and
c. Removing the retinoic acid and subsequently treating the cells with at least one fibroblast growth factor.

Any cell expressing markers characteristic of the definitive endoderm lineage is suitable for differentiating into a cell expressing markers characteristic of the pancreatic endoderm lineage using this method.

In one embodiment, the cells expressing markers characteristic of the definitive endoderm are treated with retinoic acid for about one to about three days. In one embodiment, the cells expressing markers characteristic of the definitive endoderm are treated with retinoic acid for about three days. In one embodiment, the cells expressing markers characteristic of the definitive endoderm are treated with at least one fibroblast growth factor for about one to about three days. In one embodiment, the cells expressing markers characteristic of the definitive endoderm are treated with at least one fibroblast growth factor for about three days.

The at least one fibroblast growth factor is selected from the group consisting of FGF-2, FGF-4 and FGF-10.

Any cell expressing markers characteristic of the definitive endoderm lineage is suitable for differentiating into a cell expressing markers characteristic of the pancreatic endoderm lineage using this method. In one embodiment, the cells expressing markers characteristic of the definitive endoderm lineage are treated with retinoic acid. Alternatively, the cells expressing markers characteristic of the definitive endoderm lineage are treated with FGF-2, or alternatively FGF-4, or alternatively FGF-10. In an alternate embodiment, the cells expressing markers characteristic of the definitive endoderm lineage are treated with at least one of the following factors: retinoic acid, FGF-2, FGF-4 or FGF-10. In an alternate embodiment, the cells expressing markers characteristic of the definitive endoderm lineage are treated with retinoic acid and at least one of the following fibroblast growth factors: FGF-2, FGF-4 or FGF-10. In one embodiment, the cells expressing markers characteristic of the definitive endoderm lineage are treated with retinoic acid and FGF-2. In another embodiment, the cells expressing markers characteristic of the definitive endoderm lineage are treated with retinoic acid and FGF-4. In a further embodiment, the cells expressing markers characteristic of the definitive endoderm lineage are treated with retinoic acid and FGF-10.

Retinoic acid may be used at a concentration from about 1 nM to about 1 mM. In one embodiment, retinoic acid is used at a concentration of 1 µM.

FGF-2 may be used at a concentration from about 50 pg/ml to about 50 µg/ml. In one embodiment, FGF-2 is used at a concentration of 50 ng/ml.

FGF-4 may be used at a concentration from about 50 pg/ml to about 50 µg/ml. In one embodiment, FGF-4 is used at a concentration of 50 ng/ml.

FGF-10 may be used at a concentration from about 50 pg/ml to about 50 µg/ml. In one embodiment, FGF-10 is used at a concentration of 50 ng/ml.

Cells expressing markers characteristic of the definitive endoderm lineage may be treated with at least one other additional factor that may enhance the formation of cells expressing markers characteristic of the pancreatic endoderm lineage. Alternatively, the at least one other additional factor may enhance the proliferation of the cells expressing markers characteristic of the pancreatic endoderm lineage formed by the methods of the present invention. Further, the at least one other additional factor may enhance the ability of the cells expressing markers characteristic of the pancreatic endoderm lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valproic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

Detection of Cells Expressing Markers Characteristic of the Pancreatic Endoderm Lineage Markers characteristic of the pancreatic endoderm lineage are well known to those skilled in the art, and additional markers characteristic of the pancreatic endoderm lineage continue to be identified. These markers can be used to confirm that the cells treated in accordance with the present invention have differentiated to acquire the properties characteristic of the pancreatic endoderm lineage. Pancreatic endoderm lineage specific markers include the expression of one or more transcription factors such as, for example, Hlxb9, PTF-1a, PDX-1, HNF-6, HNF-1beta.

The efficiency of differentiation may be determined by exposing a treated cell population to an agent (such as an antibody) that specifically recognizes a protein marker expressed by cells expressing markers characteristic of the pancreatic endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

Formation of Cells Expressing Markers Characteristic of the Pancreatic Endocrine Lineage Cells expressing markers characteristic of the pancreatic endoderm lineage may be differentiated into cells expressing markers characteristic of the pancreatic endocrine lineage by any method in the art or by any method disclosed in this invention.

For example, cells expressing markers characteristic of the pancreatic endoderm lineage may be differentiated into cells expressing markers characteristic of the pancreatic endocrine lineage according to the methods disclosed in D'Amour et al, Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4, then removing the medium containing DAPT and exendin 4 and subsequently culturing the cells in medium containing exendin 1, IGF-1 and HGF. An example of this method is disclosed in Nature Biotechnology 24, 1392-1401 (2006).

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D'Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing DAPT and exendin 4. An example of this method is disclosed in D'Amour et al, Nature Biotechnology, 2006.

For example, cells expressing markers characteristic of the pancreatic endoderm lineage are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al, Nature Biotechnology, 2006.

In one aspect of the present invention, cells expressing markers characteristic of the pancreatic endoderm lineage are further differentiated into cells expressing markers characteristic of the pancreatic endocrine lineage, by treating the cells expressing markers characteristic of the pancreatic endoderm lineage with a factor that inhibits the Notch signaling pathway. The factor that inhibits the Notch signaling pathway may be an antagonist for the Notch extracellular receptor. Alternatively, the factor may inhibit the biological activity of the Notch receptor. Alternatively, the factor may inhibit or be an antagonist of an element in the Notch signal transduction pathway within a cell.

In one embodiment the factor that inhibits the Notch signaling pathway is a γ-secretase inhibitor. In one embodiment, the γ-secretase inhibitor is 1S-Benzyl-4R-[1-(1S-carbamoyl-2-phenethylcarbamoyl)-1S-3-methylbutylcarbamoyl]-2R-hydrozy-5-phenylpentyl] carbamic Acid tert-butyl Ester, also known as L-685,458.

L-685,458 may be used at a concentration from about 0.1 μM to about 100 μM. In one embodiment, L-685,458 is used at a concentration of about 90 μM. In one embodiment, L-685,458 is used at a concentration of about 80 μM. In one embodiment, L-685,458 is used at a concentration of about 70 μM. In one embodiment, L-685,458 is used at a concentration of about 60 μM. In one embodiment, L-685,458 is used at a concentration of about 50 μM. In one embodiment, L-685,458 is used at a concentration of about 40 μM. In one embodiment, L-685,458 is used at a concentration of about 30 μM. In one embodiment, L-685,458 is used at a concentration of about 20 μM. In one embodiment, L-685,458 is used at a concentration of about 10 μM.

In one embodiment, the present invention provides a method for differentiating cells expressing markers characteristic of the pancreatic endoderm lineage into cells expressing markers characteristic of the pancreatic endocrine lineage, comprising the steps of:
a. Culturing cells expressing markers characteristic of the pancreatic endoderm lineage, and
b. Treating the cells with a factor that inhibits the Notch signaling pathway.

Any cell expressing markers characteristic of the pancreatic endoderm lineage is suitable for differentiating into a cell expressing markers characteristic of the pancreatic endocrine lineage using this method.

In one embodiment, factor that inhibits the Notch signaling pathway is a γ-secretase inhibitor. In one embodiment, the γ-secretase inhibitor is 1S-Benzyl-4R-[1-(1S-carbamoyl-2-phenethylcarbamoyl)-1S-3-methylbutylcarbamoyl]-2R-hydrozy-5-phenylpentyl] carbamic Acid tert-butyl Ester, also known as L-685,458.

The cells expressing markers characteristic of the pancreatic endoderm lineage are treated with the factor that inhibits the Notch signaling pathway for about one to about five days. Alternatively, the cells expressing markers characteristic of the pancreatic endoderm lineage are treated with the factor that inhibits the Notch signaling pathway for about three to about five days. Alternatively, the cells expressing markers characteristic of the pancreatic endoderm lineage are treated with the factor that inhibits the Notch signaling pathway for about five days.

In one embodiment, factor that inhibits the Notch signaling pathway is a γ-secretase inhibitor. In one embodiment, the γ-secretase inhibitor is 1S-Benzyl-4R-[1-(1S-carbamoyl-2-phenethylcarbamoyl)-1S-3-methylbutylcarbamoyl]-2R-hydrozy-5-phenylpentyl] carbamic Acid tert-butyl Ester, also known as L-685,458.

L-685,458 may be used at a concentration from about 0.1 μM to about 100 μM. In one embodiment, L-685,458 is used at a concentration of about 90 μM. In one embodiment, L-685,458 is used at a concentration of about 80 μM. In one embodiment, L-685,458 is used at a concentration of about 70 μM. In one embodiment, L-685,458 is used at a concentration of about 60 μM. In one embodiment, L-685,458 is used at a concentration of about 50 μM. In one embodiment, L-685,458 is used at a concentration of about 40 μM. In one embodiment, L-685,458 is used at a concentration of about 30 μM. In one embodiment, L-685,458 is used at a concentration of about 20 μM. In one embodiment, L-685,458 is used at a concentration of about 10 μM.

Cells expressing markers characteristic of the pancreatic endoderm lineage may be treated with at least one other additional factor that may enhance the formation of cells expressing markers characteristic of the pancreatic endocrine lineage. Alternatively, the at least one other additional factor may enhance the proliferation of the cells expressing markers characteristic of the pancreatic endocrine lineage formed by the methods of the present invention. Further, the at least one other additional factor may enhance the ability of the cells expressing markers characteristic of the pancreatic endocrine lineage formed by the methods of the present invention to form other cell types, or improve the efficiency of any other additional differentiation steps.

The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valproic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

In one embodiment, the present invention provides an improved method for differentiating cells expressing markers characteristic of the pancreatic endoderm lineage into cells expressing markers characteristic of the pancreatic endocrine lineage, comprising the steps of:
a. Culturing cells expressing markers characteristic of the pancreatic endoderm lineage, and
b. Treating the cells with a factor capable of differentiating cells expressing markers characteristic of the pancreatic endoderm lineage into cells expressing markers characteristic of the pancreatic endocrine lineage, in medium containing glucose at a concentration from about 10 mM to about 20 mM.

Any cell expressing markers characteristic of the pancreatic endoderm lineage is suitable for differentiating into a cell expressing markers characteristic of the pancreatic endocrine lineage using this method.

Any method capable of differentiating cells expressing markers characteristic of the pancreatic endoderm lineage into cells expressing markers characteristic of the pancreatic endocrine lineage is suitable for the improvement of the present invention.

In one embodiment, the cells expressing markers characteristic of the pancreatic endoderm lineage are treated in a medium containing glucose at a concentration of about 10 mM. In an alternate embodiment, the cells are treated in a medium containing glucose at a concentration of about 20 mM.

Cells expressing markers characteristic of the pancreatic endoderm lineage are treated for about 2 to about 30 days. In one embodiment cells expressing markers characteristic of the pancreatic endoderm lineage are treated for about 2 to about 20 days. In one embodiment, cells expressing markers characteristic of the pancreatic endoderm lineage are treated for about 2 to about 10 days. In one embodiment, cells expressing markers characteristic of the pancreatic endoderm lineage are treated for about 10 days. In one embodiment, cells expressing markers characteristic of the pancreatic endoderm lineage are treated for about 4 days. In one embodiment, cells expressing markers characteristic of the pancreatic endoderm lineage are treated for about 2 days.

Detection of Cells Expressing Markers Characteristic of the Pancreatic Endocrine Lineage Markers characteristic of cells of the pancreatic endocrine lineage are well known to those skilled in the art, and additional markers characteristic of the pancreatic endocrine lineage continue to be identified. These markers can be used to confirm that the cells treated in accordance with the present invention have differentiated to acquire the properties characteristic of the pancreatic endocrine lineage. Pancreatic endocrine lineage specific markers include the expression of one or more transcription factors such as, for example, NGN-3, NeuroD, Islet-1.

Markers characteristic of cells of the β cell lineage are well known to those skilled in the art, and additional markers characteristic of the β cell lineage continue to be identified. These markers can be used to confirm that the cells treated in accordance with the present invention have differentiated to acquire the properties characteristic of the β-cell lineage. β cell lineage specific characteristics include the expression of one or more transcription factors such as, for example, Pdx1 (pancreatic and duodenal homeobox gene-1), Nkx2.2, Nkx6.1, Is11, Pax6, Pax4, NeuroD, Hnf1b, Hnf-6, Hnf-3beta, and MafA, among others. These transcription factors are well established in the art for identification of endocrine cells. See, e.g., Edlund (Nature Reviews Genetics 3: 524-632 (2002)).

The efficiency of differentiation may be determined by exposing a treated cell population to an agent (such as an antibody) that specifically recognizes a protein marker expressed by cells expressing markers characteristic of the pancreatic endocrine lineage. Alternatively, the efficiency of differentiation may be determined by exposing a treated cell population to an agent (such as an antibody) that specifically recognizes a protein marker expressed by cells expressing markers characteristic of the β cell lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

Therapies

In one aspect, the present invention provides a method for treating a patient suffering from, or at risk of developing, Type1 diabetes. This method involves culturing pluripotent stem cells, differentiating the pluripotent stem cells in vitro into a β-cell lineage, and implanting the cells of a β-cell lineage into a patient.

In yet another aspect, this invention provides a method for treating a patient suffering from, or at risk of developing, Type 2 diabetes. This method involves culturing pluripotent stem cells, differentiating the cultured cells in vitro into a β-cell lineage, and implanting the cells of a β-cell lineage into the patient.

If appropriate, the patient can be further treated with pharmaceutical agents or bioactives that facilitate the survival and function of the transplanted cells. These agents may include, for example, insulin, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-1) and II, GLP-1 and 2 mimetibody, Exendin-4, retinoic acid, parathyroid hormone, MAPK inhibitors, such as, for example, compounds disclosed in U.S. Published Application 2004/0209901 and U.S. Published Application 2004/0132729.

The pluripotent stem cells may be differentiated into an insulin-producing cell prior to transplantation into a recipient. In a specific embodiment, the pluripotent stem cells are fully differentiated into β-cells, prior to transplantation into a recipient. Alternatively, the pluripotent stem cells may be transplanted into a recipient in an undifferentiated or partially differentiated state. Further differentiation may take place in the recipient.

Definitive endoderm cells or, alternatively, pancreatic endoderm cells, or, alternatively, β cells, may be implanted as dispersed cells or formed into clusters that may be infused into the hepatic portal vein. Alternatively, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells, additional factors, such as growth factors, antioxidants or anti-inflammatory agents, can be administered before, simultaneously with, or after the administration of the cells. In certain embodiments, growth factors are utilized to differentiate the administered cells in vivo. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In one aspect, this invention provides a method for treating a patient suffering from, or at risk of developing diabetes. This method involves culturing pluripotent stem cells, differentiating the cultured cells in vitro into a β-cell lineage, and incorporating the cells into a three-dimensional support. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. Nos. 5,770,417, 6,022,743, 5,567,612, 5,759,830, 6,626,950, 6,534,084, 6,306,424, 6,365,149, 6,599,323, 6,656,488, U.S. Published Application 2004/0062753 A1, U.S. Pat. Nos. 4,557,264 and 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945.

The support may also be incorporated with at least one pharmaceutical compound that is an inhibitor of fibrosis, such as, for example, compounds disclosed in U.S. Pat. No. 6,331,298.

The support may also be incorporated with at least one pharmaceutical compound that is capable of enhancing angiogenesis, such as, for example, compounds disclosed in U.S. Published Application 2004/0220393 and U.S. Published Application 2004/0209901.

The support may also be incorporated with at least one pharmaceutical compound that is an immunosuppressive compound, such as, for example, compounds disclosed in U.S. Published Application 2004/0171623.

The support may also be incorporated with at least one pharmaceutical compound that is a growth factor, such as, for example, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-I (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a scaffold can be achieved by the simple depositing of cells onto the scaffold. Cells can enter into the scaffold by simple diffusion (J. Pediatr. Surg. 23 (1 Pt 2): 3-9 (1988)). Several other approaches have been developed to enhance the efficiency of cell seeding. For example, spinner flasks have been used in seeding of chondrocytes onto polyglycolic acid scaffolds (Biotechnol. Prog. 14(2): 193-202 (1998)). Another approach for seeding cells is the use of centrifugation, which yields minimum stress to the seeded cells and enhances seeding efficiency. For example, Yang et al. developed a cell seeding method (J. Biomed. Mater. Res. 55(3): 379-86 (2001)), referred to as Centrifugational Cell Immobilization (CCI).

The present invention is further illustrated, but not limited by, the following examples.

BACKGROUND

Example 1

Human Embryonic Stem Cell Culture

The human embryonic stem cell lines H1, H7 and H9 were obtained from WiCell Research Institute, Inc., (Madison, WI) and cultured according to instructions provided by the source institute. Briefly, cells were cultured on mouse embryonic fibroblast (MEF) feeder cells in ES cell medium consisting of DMEM/F12 (Invitrogen/GIBCO) supplemented with 20% knockout serum replacement, 100 nM MEM nonessential amino acids, 0.5 mM betamercaptoethanol, 2 mM L-glutamine with 4 ng/ml human basic fibroblast growth factor (bFGF) (all from Invitrogen/GIBCO). MEF cells, derived from E13 to 13.5 mouse embryos, were purchased from Charles River. MEF cells were expanded in DMEM medium supplemented with 10% FBS (Hyclone), 2 mM glutamine, and 100 mM MEM nonessential amino acids. Sub-confluent MEF cell cultures were treated with 10 µg/ml mitomycin C (Sigma, St. Louis, MO) for 3 h to arrest cell division, then trypsinized and plated at $2 \times 10^4/cm^2$ on 0.1% bovine gelatin-coated dishes. MEF cells from passage two through four were used as feeder layers. Human embryonic stem cells plated on MEF cell feeder layers were cultured at 37° C. in an atmosphere of 5% $CO_2$ within a humidified tissue culture incubator. When confluent (approximately 5-7 days after plating), human embryonic stem cells were treated with 1 mg/ml collagenase type IV (Invitrogen/GIBCO) for 5-10 min and then gently scraped off the surface using a 5-ml pipette. Cells were spun at 900 rpm for 5 min, and the pellet was resuspended and re-plated at a 1:3 to 1:4 ratio of cells in fresh culture medium.

Example 2

Formation of Definitive Endoderm Cells

The effects of activin A on the expression of markers of definitive endoderm were examined. Activin A (100 ng/ml) was added to populations of human embryonic stem cells cultured on mouse embryonic fibroblasts. Cells were cultured continuously in the presence of activin A and harvested at the times indicated. The level of expression of definitive endoderm markers was examined by PCR (FIG. 1), FACS (results summarized in Table II), and immunohistochemistry (FIG. 2).

Figure 1A:
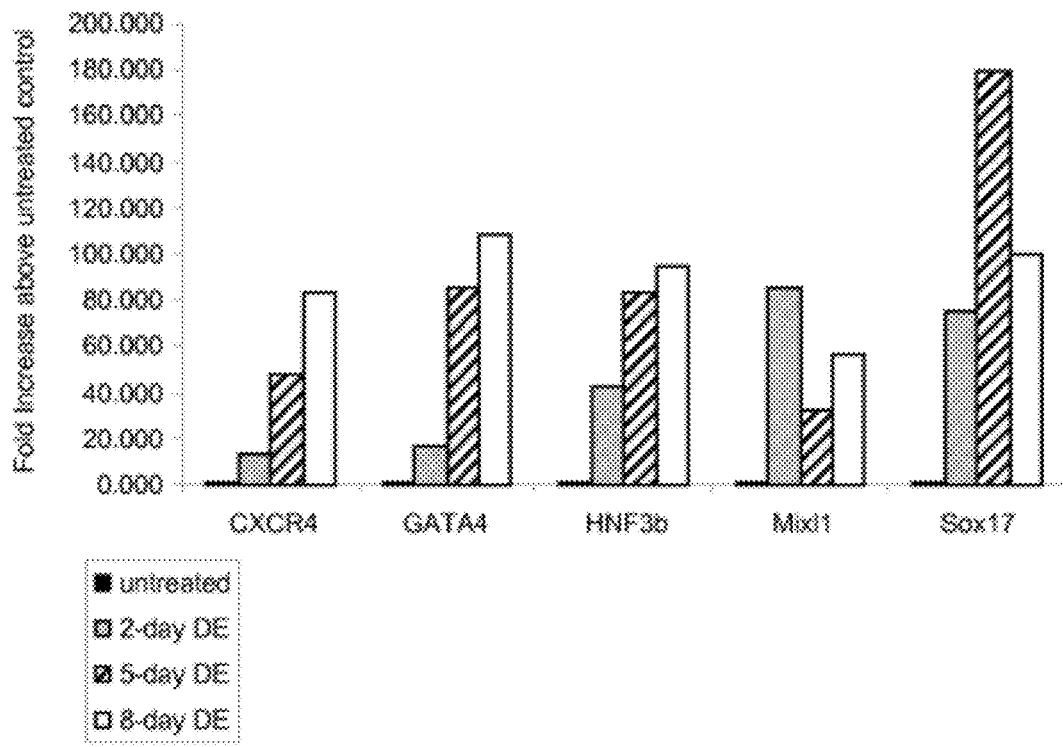
FIG. 1A shows the expression of the definitive endoderm markers CXCR4, GATA4, HNF-3beta, Mix11, Sox-17 in the human embryonic stem cell line H9 following treatment with 100 ng/ml activin A for two, five and eight days. Expression of definitive endoderm markers was assayed at the mRNA level and normalized to expression levels in untreated human embryonic stem cells.
Figure 1B:
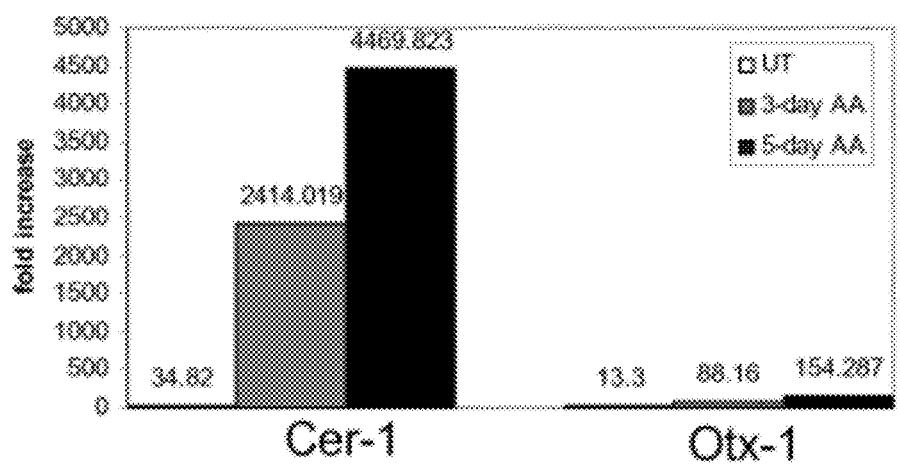
FIG. 1B shows the expression of the anterior endoderm markers Cerberus, Otx-1 and Hex genes in the human embryonic stem cell line H9 following treatment with 100 ng/ml activin A for three and five days.
Figure 2A:
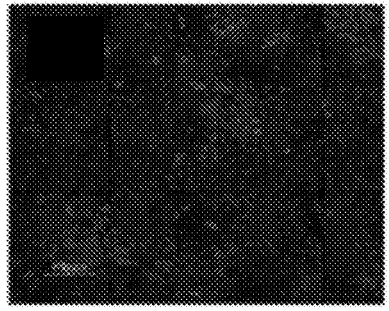
FIGS. 2A-2C show the expression of definitive endoderm markers in the human embryonic stem cell line H9 following treatment with 100 ng/ml activin A for five days. Expression of the definitive endoderm markers was detected by immunohistochemistry.
Figure 2B:
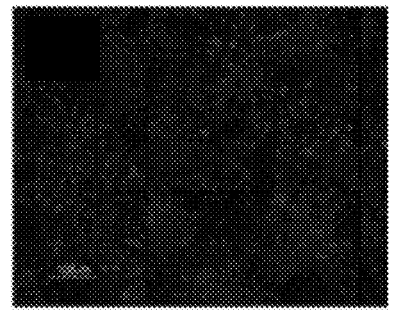
Figure 2C:
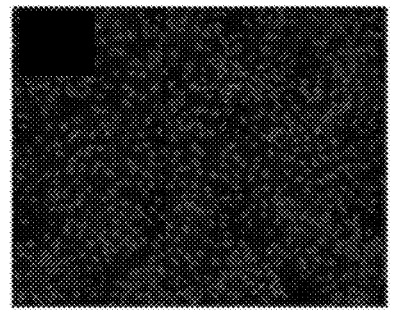

Activin A evoked a time-dependent increase in the expression of CXCR4, GATA4, HNF-3beta, Mix11 and Sox-17 mRNA in the H9 line (FIG. 1A). A significant up regulation of anterior endoderm markers, Cerberus, Otx-1 and Hex genes was also observed (FIG. 1B). An increase in CXCR4 protein was observed by FACS analysis following activin A treatment. The expression of E-cadherin and N-cadherin did not change following activin A treatment (Table IIA). CXCR4 positive cells were also highly positive for C-kit, EPCAM, CD99, and negative for CD9. The expression pattern for these markers was consistent among all three hES cell lines examined (Table IIB for H7 and Table IIC for H1). Immunocytochemistry conducted on cells treated with activin A for five days revealed that 30-40% cells in the treated culture were positive for Sox17 and HNF-3beta. In parallel, almost 100% of the differentiated cells were still Oct4 positive (FIG. 2). With the decrease in expression of surface markers of pluripotency, combined with an increase in the expression of definitive endoderm markers, these data suggest that activin A promotes the differentiation of human embryonic stem cells to definitive endoderm.

Example 3

Formation of Pancreatic Endoderm Cells

Growth factors known to induce the differentiation of human embryonic stem cells to pancreatic endoderm were added to cell cultures. In particular, activin A, bFGF, and retinoic acid, known to induce the formation of pancreatic endoderm, were added to cell cultures.

Figure 3A:
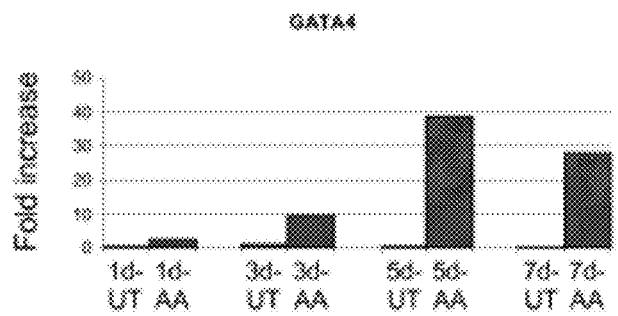
FIGS. 3A-3C show the expression of definitive endoderm markers in the human embryonic stem cell line H9 following a step-wise differentiation protocol. Expression of the definitive endoderm markers was assayed at the mRNA level and normalized to expression levels in untreated human embryonic stem cells.
Figure 3B:
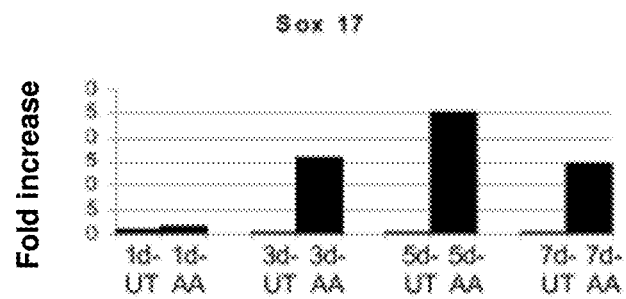
Figure 3C:
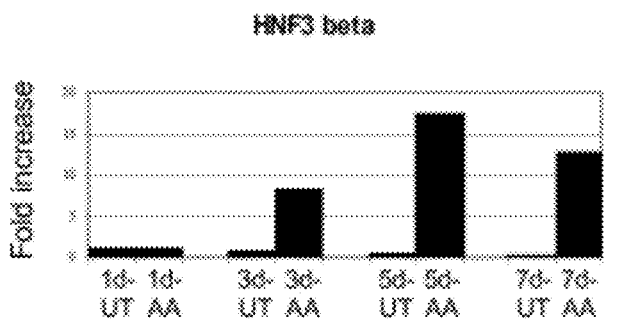
Figure 3D:
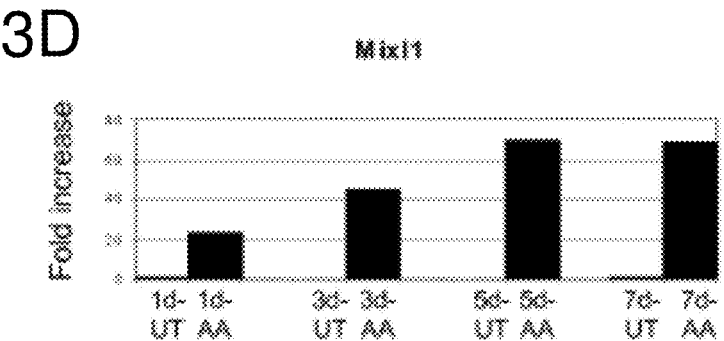
FIG. 3D shows Mix11 expression. Data points marked 'AA' denote activin A treatment for one (1 d), three (3 d), five (5 d), or seven days (7 d). Data points marked 'UT' denote untreated controls cultured for one (1 d), three (3 d), five (5 d), or seven days (7 d).
Figure 4A:
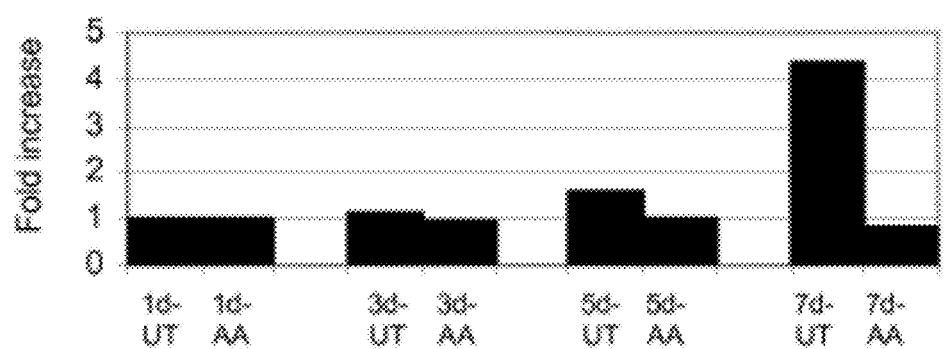
FIGS. 4A-4B show the expression of extra-embryonic endoderm markers in the human embryonic stem cell line H9 following a step-wise differentiation protocol. Expression of the extraembryonic endoderm markers was assayed at the mRNA level and normalized to expression levels in untreated human embryonic stem cells.

In a first series of experiments, activin A, was added to populations of human embryonic stem cells cultured on mouse embryonic fibroblasts for up to seven days in DMEM/F12 supplemented with 0% to 2% serum and Activin A (100 ng/ml). Cells were harvested at the time points indicated in FIG. 3 and assayed by PCR for the expression of genes shown (FIGS. 3, 4 and 5). In FIG. 3, PCR analysis indicated that activin treated cells expressed a broad spectrum of genes associated with endoderm development, including GATA4 (FIG. 3A), Sox-17 (FIG. 3B), HNF-3beta (FIG. 3C), and Mix1-1 (FIG. 3D). However, no Pdx1 gene expression was observed. The same expression pattern of endoderm lineage markers was observed in Activin A treated H7 cells (FIGS. 6A-6F). At this stage, there was no significant decrease of Oct4 expression.

Figure 4B:
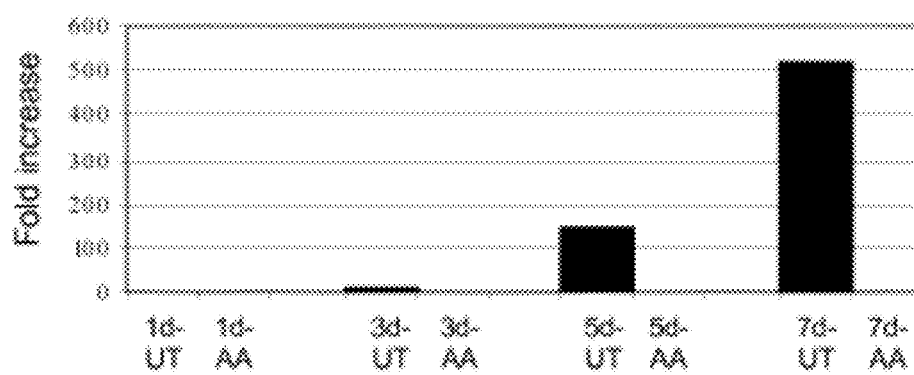
Figure 5A:
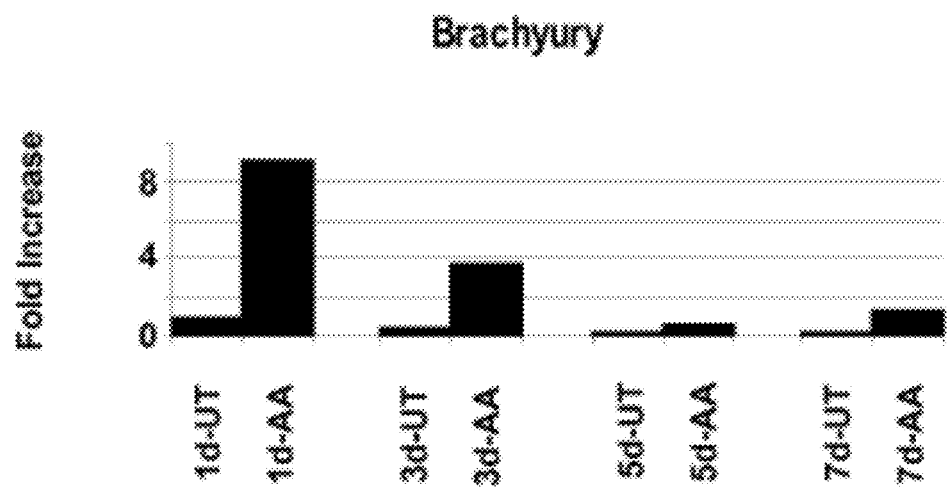
FIGS. 5A-5B show the expression of mesoderm and ectoderm markers in the human embryonic stem cell line H9 following a step-wise differentiation protocol. Expression of the mesoderm and ectoderm markers was assayed at the mRNA level and normalized to expression levels in untreated human embryonic stem cells.
Figure 5B:
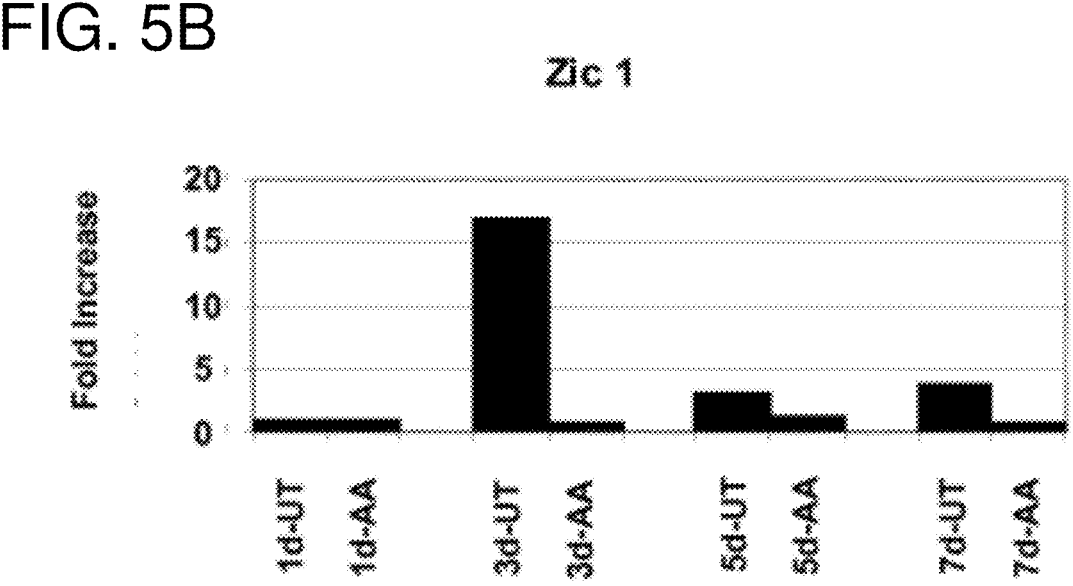
Figure 6A:
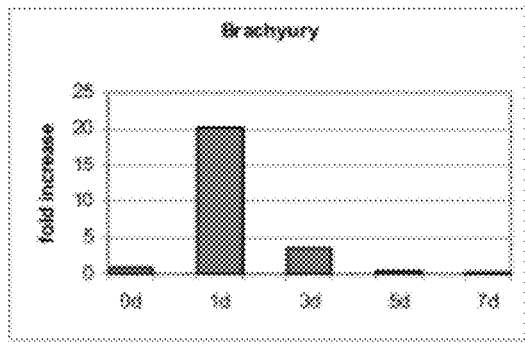
FIGS. 6A-6F show the expression of the definitive endoderm markers Brachyury (FIG. 6A) CXCR4 (FIG. 6B), Mix11 (FIG. 6C), Sox17 (FIG. 6D), HNF-3beta (FIG. 6E), Oct4 (FIG. 6F) in the human embryonic stem cell line H7 following treatment with 100 ng/ml activin A for one, three, five and seven days. Expression of definitive endoderm markers was assayed at the mRNA level and normalized to expression levels in untreated human embryonic stem cells.
Figure 6B:
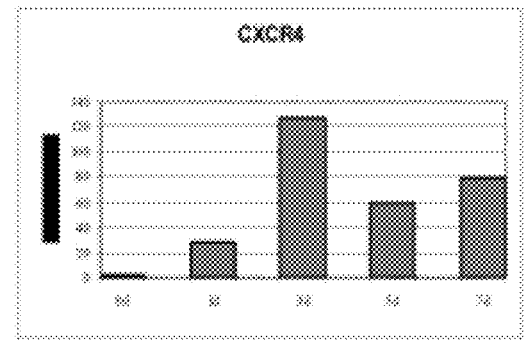
Figure 6C:
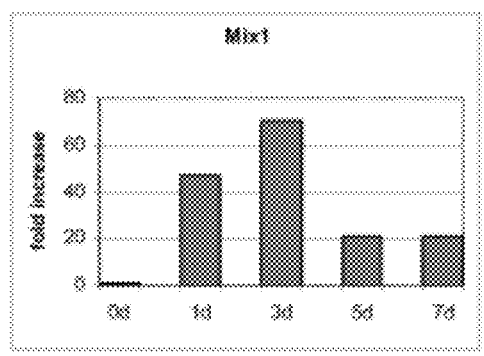
Figure 6D:
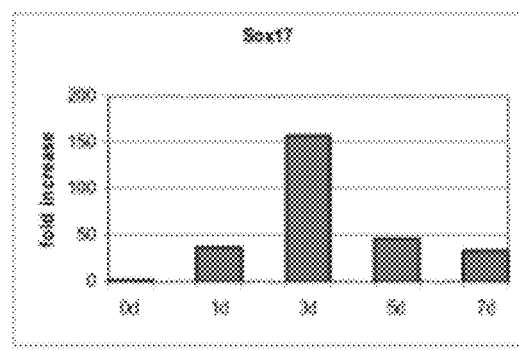
Figure 6E:
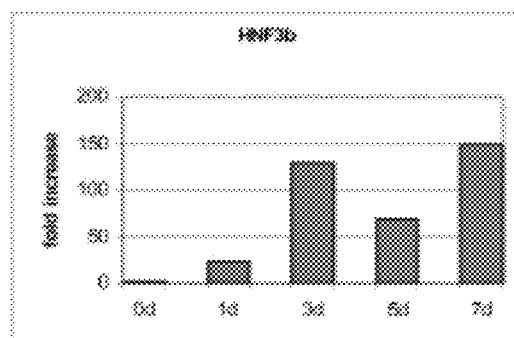
Figure 6F:
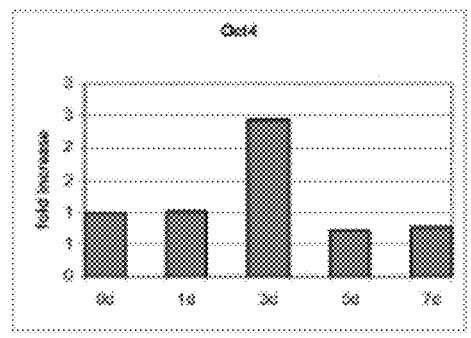
Figure 7A:
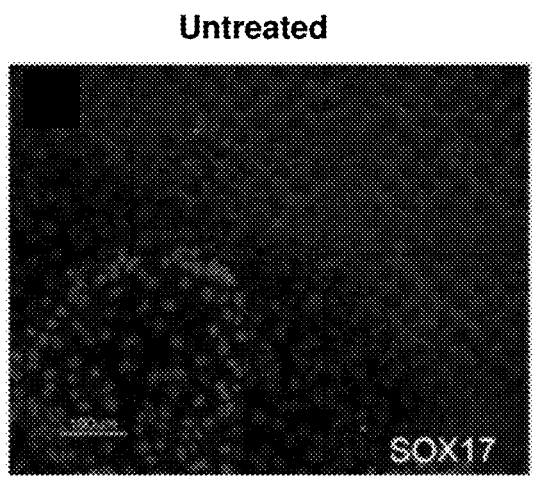
FIGS. 7A-7F show the expression of definitive endoderm markers in the human embryonic stem cell line H9 following application of a differentiation protocol. Expression of the definitive endoderm markers was detected by immunohistochemistry.
Figure 7B:
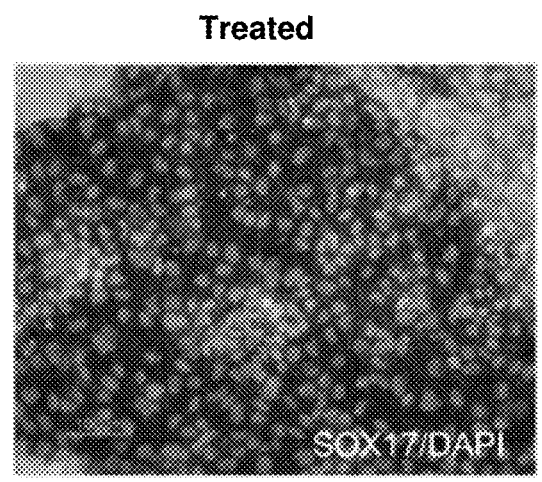
Figure 7C:
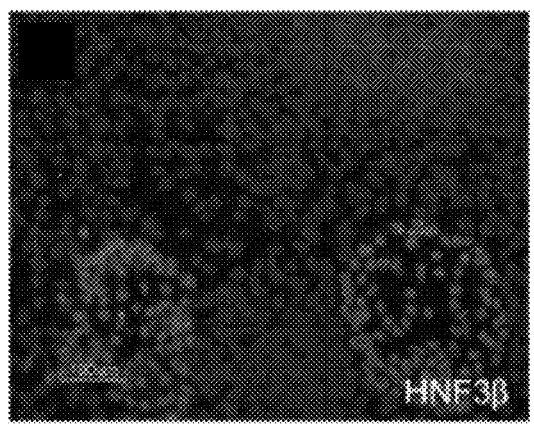
Figure 7D:
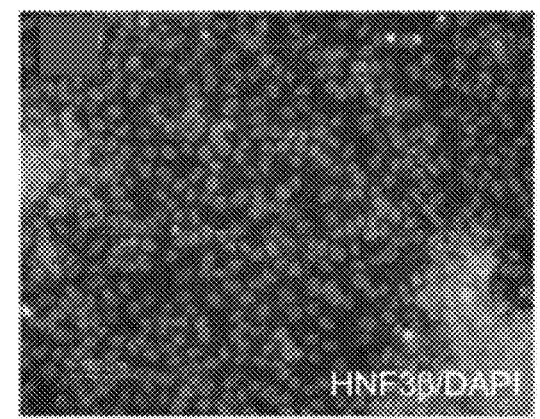
Figure 7E:
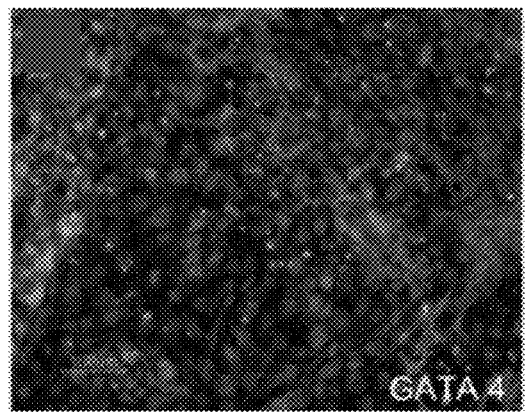
Figure 7F:
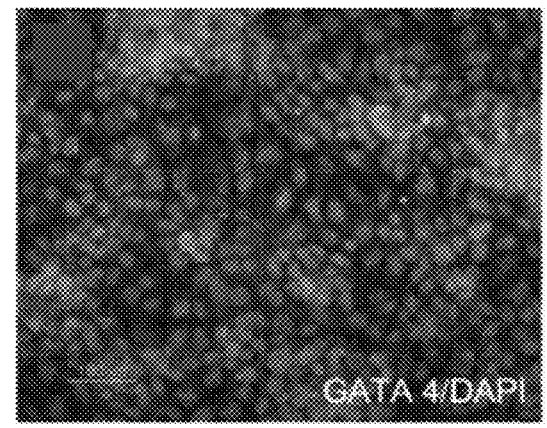

Activin A evoked a time-dependent decrease in the expression of the extraembryonic endoderm markers Sox7 (FIG. 4A) and AFP (FIG. 4B). Activin A decreased the expression of Brachyury (FIG. 5A) but had no effect on expression of the neuronal marker Zic1 (FIG. 5B).

Taken together, these data suggest that the increased expression of Sox-17, Mix11, Gata4, and HNF-3beta together with the up regulation of anterior endoderm markers Otx1, Cer1 and Hex genes, corresponds to the formation of definitive endoderm in response to activin A treatment. Analysis of definitive endoderm markers by immunocytochemistry revealed that protein expression for these genes also reflected the trends observed in mRNA expression. Levels of expression for HNF-3beta, Sox-17, and GATA4 were low in untreated cells, approximately 10 to 20% of all cells. Activin A (100 ng/ml) treatment for five days increased the expression of HNF-3beta, Sox-17, and GATA4 to approximately 50% to 90% of all cells (FIG. 7).

Figure 8A:
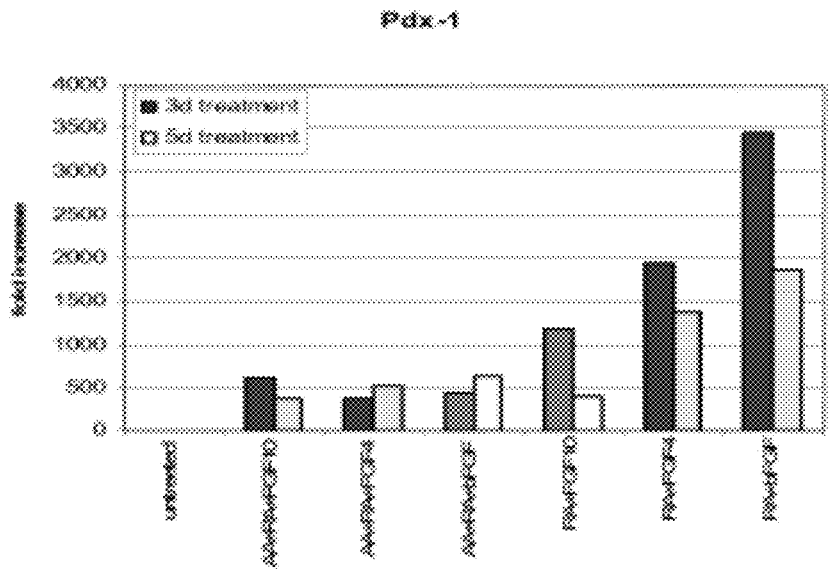
FIGS. 8A-8C show the expression of pancreatic endoderm markers in the human embryonic stem cell line H9 following application of a second differentiation protocol. Expression of the pancreatic endoderm markers was assayed by PCR and normalized to expression levels in activin A treated human embryonic stem cells.
Figure 8B:
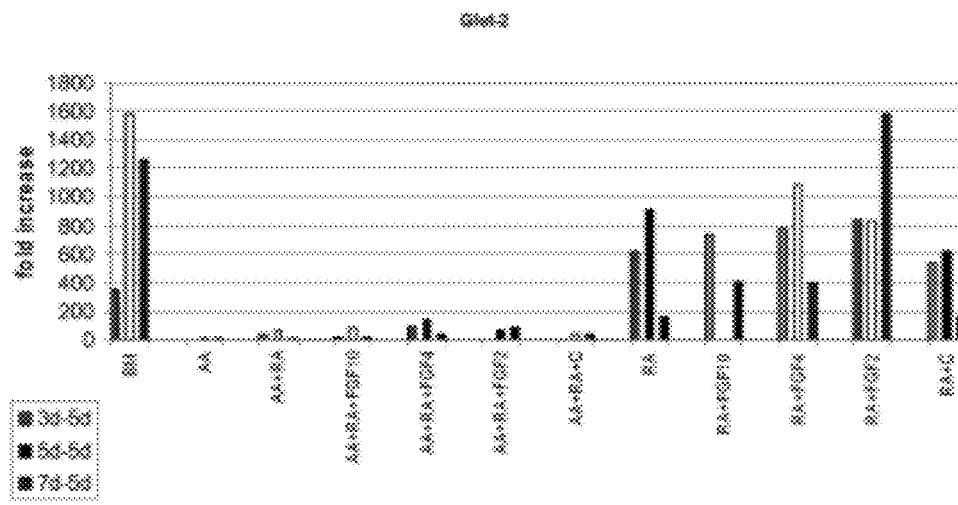
Figure 8C:
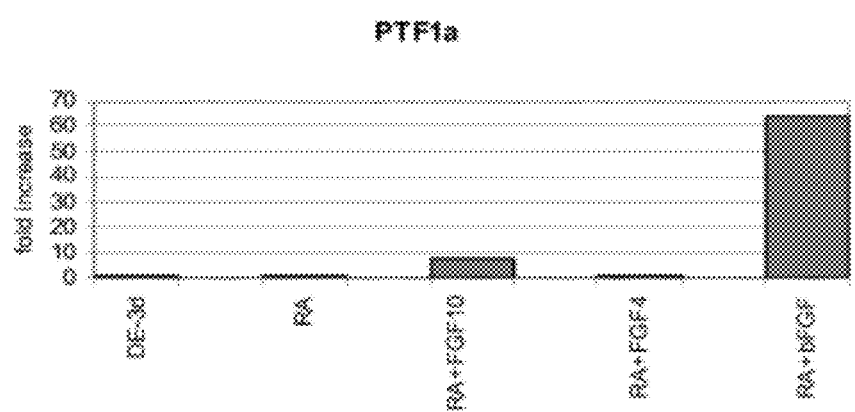

In a second series of experiments, cultures of human embryonic stem cells were maintained in undifferentiated culture conditions for 2-3 days according to the methods described in Example 1. After the cells were 70-80% confluent, the medium was changed to DMEM/F12 with 0 to 2% FBS with addition of activin A at 100 ng/ml and cultured in the presence of activin A for either three, five, or seven days. After this time interval, the cells were then further treated for five to six days with combinations of retinoic acid and bFGF as shown in FIG. 8. Cultures were harvested and samples of mRNA were collected for analysis. Control cultures consisting of cells treated with activin A alone for five days were also included.

Figure 9A:
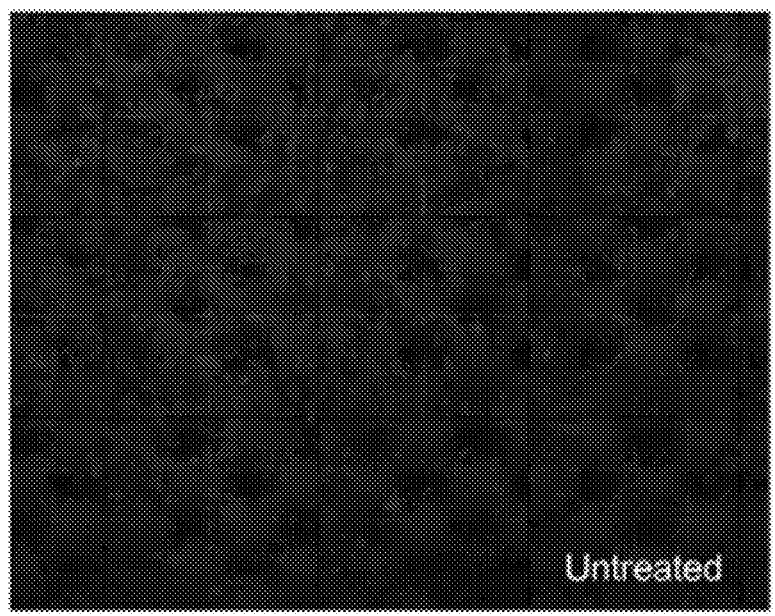
FIGS. 9A-9B show the expression of pancreatic endoderm markers in the human embryonic stem cell line H9 following application of a second differentiation protocol. Expression of the pancreatic endoderm markers was detected by immunohistochemistry.
Figure 9B:
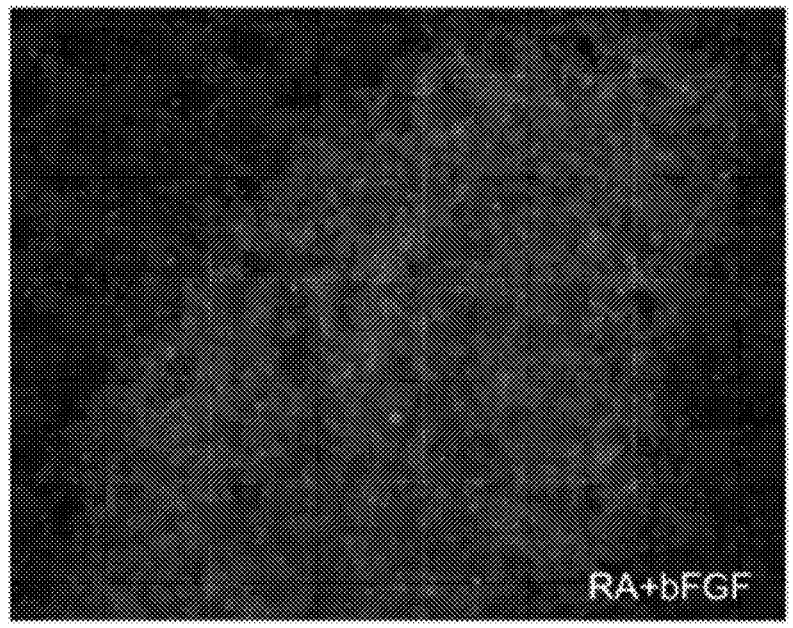

Gene expression analysis revealed that activin A or retinoic acid alone did not induce the expression of Pdx1. Similar results were observed in cultures of cells treated with retinoic acid in combination with FGF and in the presence of activin A (FIG. 8A). However, treatment of cells with retinoic acid and FGF in the absence of activin A increased the expression of Pdx1 still further (FIG. 8A). Cells treated for three days with activin A, then treated for 5 days with 1 µM retinoic acid and 50 ng/ml bFGF (also known as FGF-2) in the absence of activin A showed a level of Pdx1 expression that was approximately 3500-fold higher than that observed in samples with activin A treatment alone for 5 days (FIG. 8A). Immunocytochemistry showed that 5 to 20% of all cells expressed Pdx1 (FIG. 9).

Treatment with 1 µM retinoic acid and bFGF in the absence of activin A also caused an increase in the expression of GLUT-2 and PTF1a (FIG. 8C) that was not observed in cells treated in the presence of activin A alone. The largest increase in expression of GLUT-2 and PTF1a was observed in cells treated with 1 µM retinoic acid and 50 ng/ml bFGF. Taken together, these data suggest that the formation of pancreatic endoderm is further enhanced by removal of activin A from cell cultures after definitive endoderm has been formed.

Example 4

Formation of Pancreatic Endocrine Cells

Cultures of human embryonic stem cells were maintained in undifferentiated culture conditions for 3-4 days according to the methods described in Example 1. After the cells were 50-60% confluent, the medium was changed to DMEM/F12 without FBS, containing activin A at 100 ng/ml, and the cells were cultured in this medium for one day. Following the one day culture, the medium was removed and replaced with medium containing 0.5% FBS with 100 ng/ml activin A, and the cells were cultured for one day. Following the second one-day culture, the medium was removed and replaced with medium containing 2% FBS with 100 ng/ml activin A, and the cells were cultured for one day. After this time interval, the cells were then treated for six days with combinations of retinoic acid and FGF as outlined in Example 23, then the culture medium was removed and replaced with medium comprising DMEM/F12 with 2% FBS, containing the γ-secretase inhibitors L-685,458 at 10 µM for three days. Cultures were harvested and samples of mRNA were collected for analysis. Control cultures consisting of cells treated with activin A alone for five days were also included.

Figure 10A:
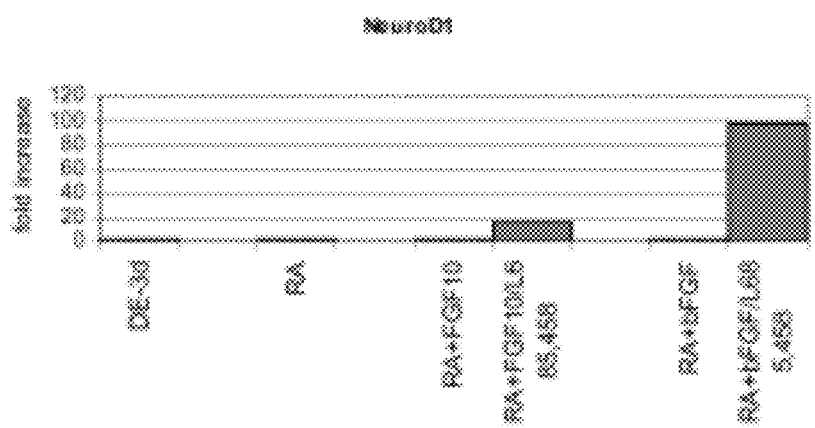
FIGS. 10A-10D show the expression of pancreatic endocrine markers in the human embryonic stem cell line H9 following application of a third differentiation protocol. Expression of the pancreatic endocrine markers was assayed by PCR and normalized to expression levels in activin A treated human embryonic stem cells.
Figure 10B:
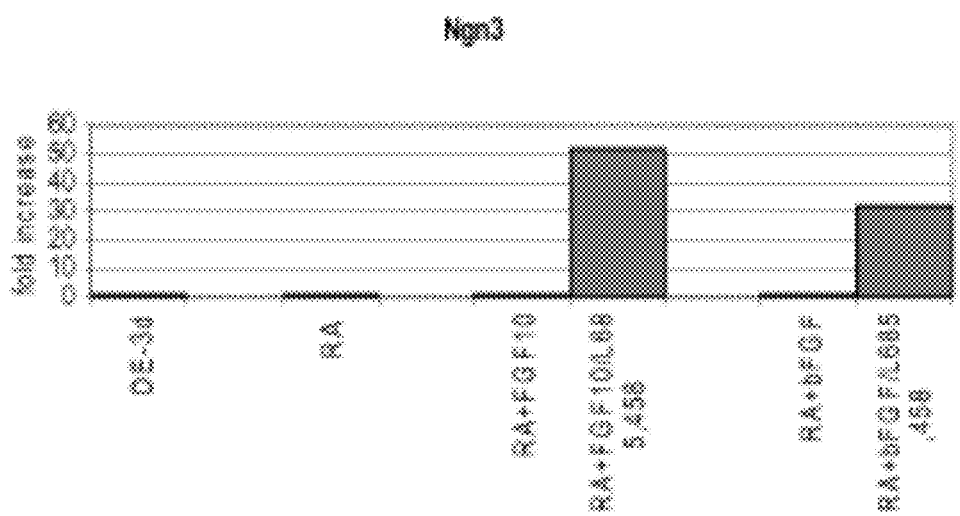
Figure 10C:
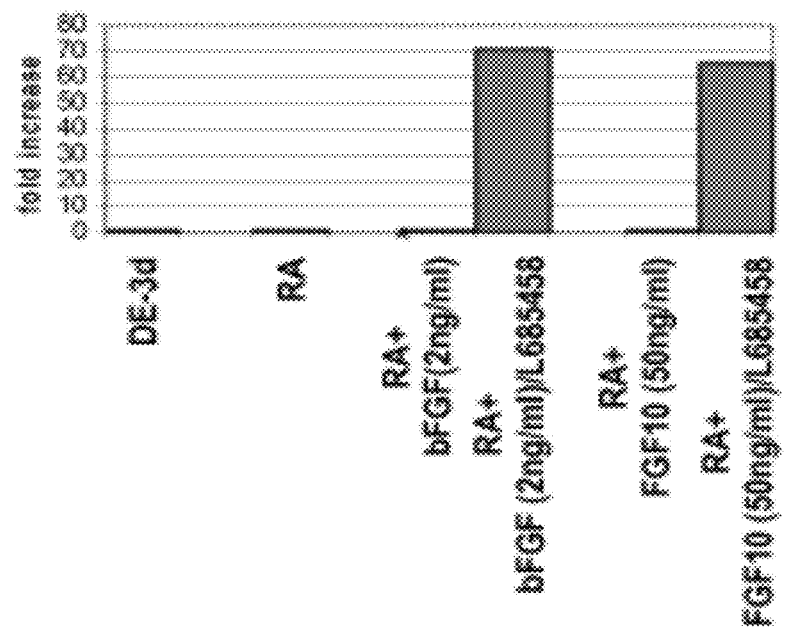
Figure 10D:
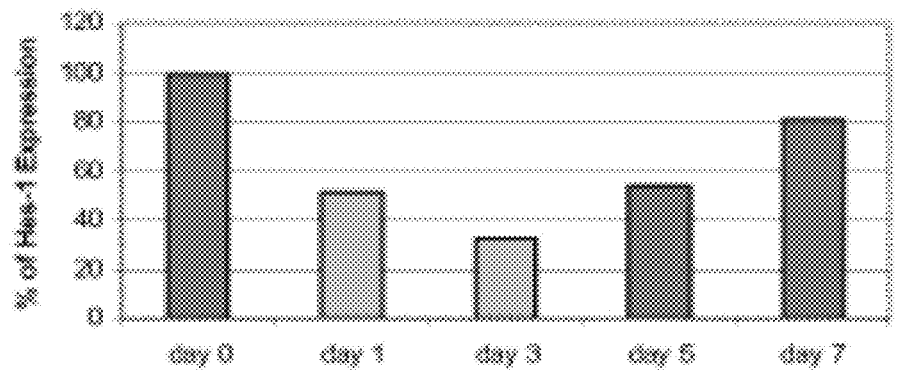

Gene expression analysis revealed that activin A alone or in combination with retinoic acid and FGFs did not induce the expression of Ngn3 or insulin (FIGS. 10A and 10C). A decrease in the expression of Hes-1 was also observed following treatment with L-685,458. The maximal inhibition was observed on day three post treatment (FIG. 10D). However, treatment of cells with L-685,458 induced the expression of Ngn3 to a level approximately 50-fold higher than that observed in samples treated with activin A alone or retinoic acid with FGFs in combination. A 70-fold increase of insulin expression was observed in samples treated with the γ-secretase inhibitor. NeuroD1 expression was also increased further by the L-685,458 treatment (FIG. 10A). Taken together, these data suggest that the formation of endocrine cells is further enhanced by removal of retinoic acid and FGFs from cell culture and the addition of γ-secretase inhibitors after pancreatic endoderm has been formed.

Example 5

Formation of Pancreatic Endocrine Cells Expressing Nkx2.2

Figure 11A:
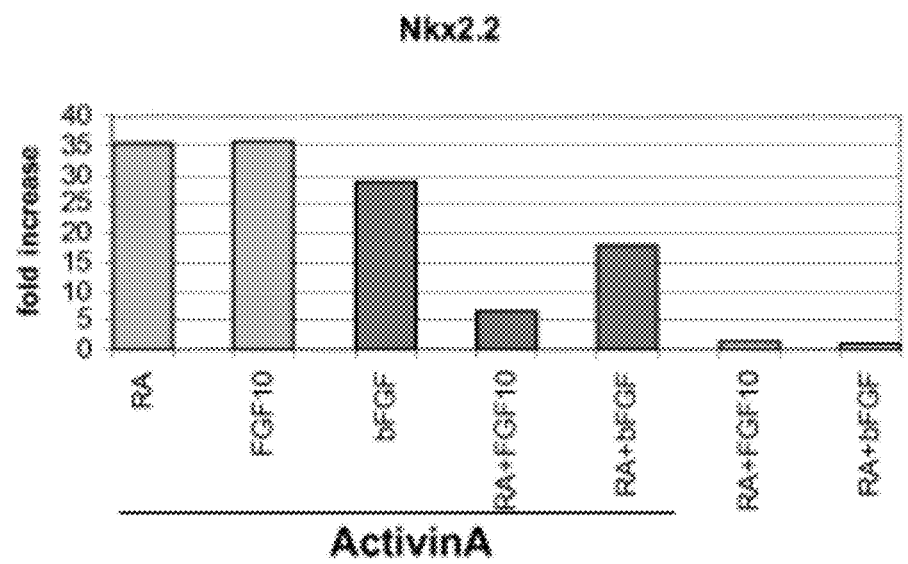
FIGS. 11A-11B show the expression of pancreatic endoderm markers in the human embryonic stem cell line H9 following application of a differentiation protocol. Expression of the pancreatic endoderm markers was assayed by PCR and normalized to expression levels in activin A treated human embryonic stem cells.
Figure 11B:
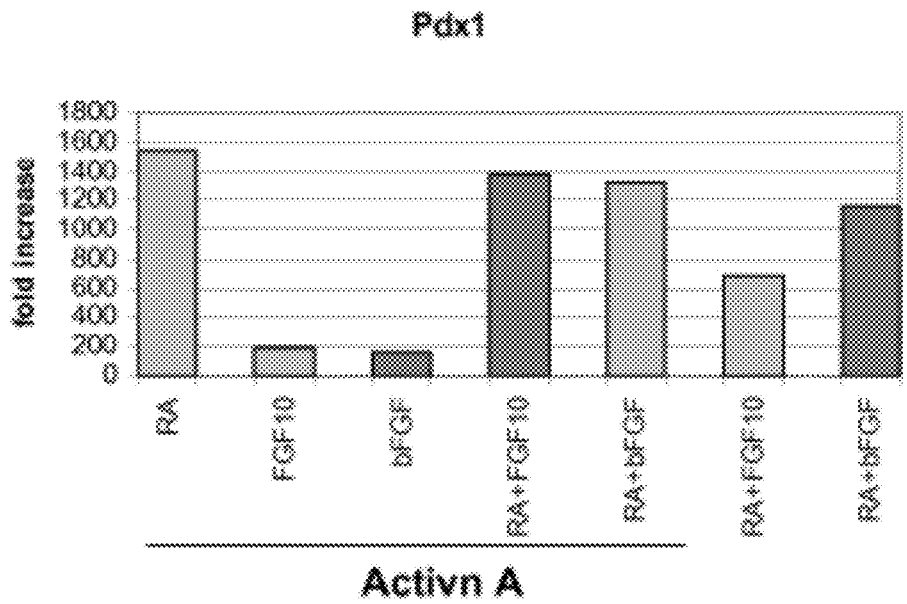

Definitive endoderm cells obtained according to the methods outlined in Example 2 were treated as follows: Cells were cultured in basal medium, comprising DMEM/F12 with 2% FBS plus 50 ng/ml activin A, 50 ng/ml basic FGF and 1 µM of Retinoic Acid for 3 to 5 days. Cells were continuously cultured for another 3 to 5 days in basal medium with retinoic acid at 1 µM, alone or with bFGF. RNA samples were harvested from cells at various time points along this process to help evaluate the directed differentiation of the cells. Furthermore, culture medium and factors were regularly removed and replenished throughout the differentiation protocol. Addition of activin A showed an increase of Nkx2.2 expression about 35-fold compared to samples without activin A. Samples treated with activin A for the first three days of culture maintained Pdx1 expression at a level similar to samples containing no activin A (FIG. 11). Taken together, these data suggest that the expression of the pancreatic endocrine marker Nkx2.2 is further enhanced by adding Activin A to the first three days of retinoic acid and bFGF treatment.

Example 6

Passage and Expansion of Pancreatic Endoderm Cells in Culture

Figure 12:
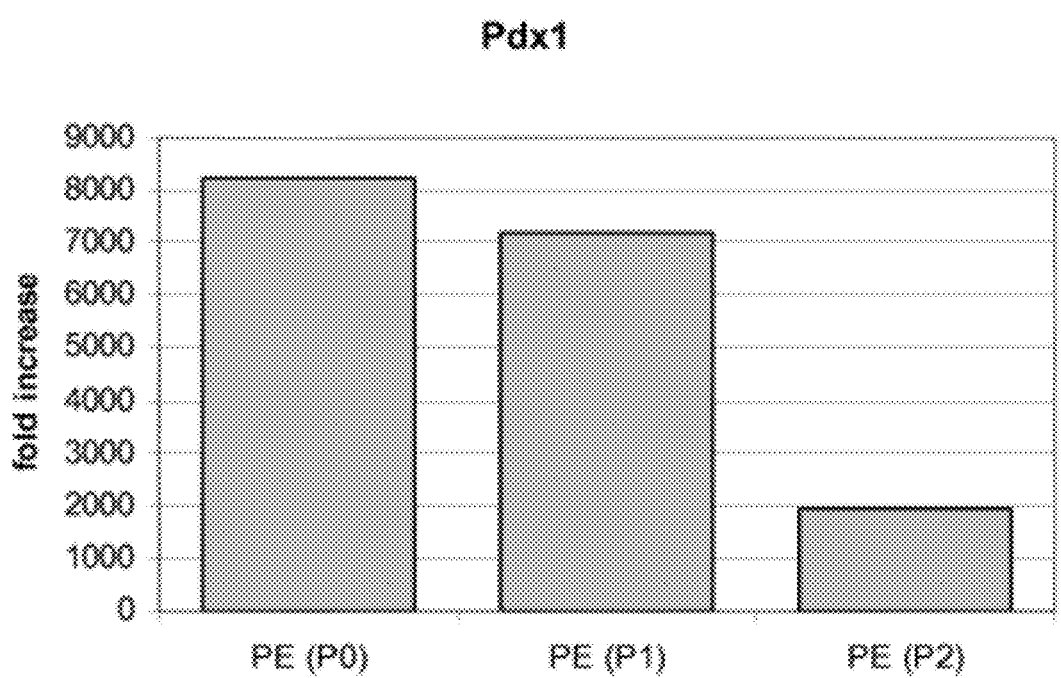
FIG. 12 shows the expression of PDX-1 in cells with each passage (P0, P1 and P2) in culture. Expression of the PDX-1 was assayed by PCR and normalized to expression levels in activin A treated human embryonic stem cells H9.

This example demonstrates that pancreatic endoderm cells derived from human embryonic stem cells herein can be maintained in cell culture and passaged without further differentiation. Pancreatic endoderm cells were differentiated in the presence of 100 ng/ml activin A in low serum DMEM/F12. The low serum DMEM/F12 contained 0% (v/v) fetal bovine serum (FBS) on day 1, 0.5% (v/v) FBS on day two and 2% (v/v) FBS on each day thereafter. After four days of differentiation, the cells were cultured in low serum DMEM/F12 contained 2% (v/v) FBS, 1 µM retinoic acid and 50 ng/ml bFGF for a total of six more days. After the six days of differentiation, the cells were maintained in culture in low serum DMEM/F12 contained 2% (v/v) FBS in the presence of 50 ng/ml FGF10 for a total of 6 days. During the six-day culture period, the pancreatic endoderm cells were passaged twice and cell population-doubling time is about 36 to 48 hours during this 6-day culture. On days 0, 3, and 6 of culture, Q-PCR was used to measure the expression of marker genes indicative of pancreatic endoderm. FIG. 12 shows that cells grown in the presence of 50 ng/ml FGF10 maintained expression of the pancreatic endoderm marker Pdx1 during the 6 day culture period subsequent to their derivation.

Example 7

Derivation of Hepatocytes from Human Embryonic Stem Cells

Figure 13A:
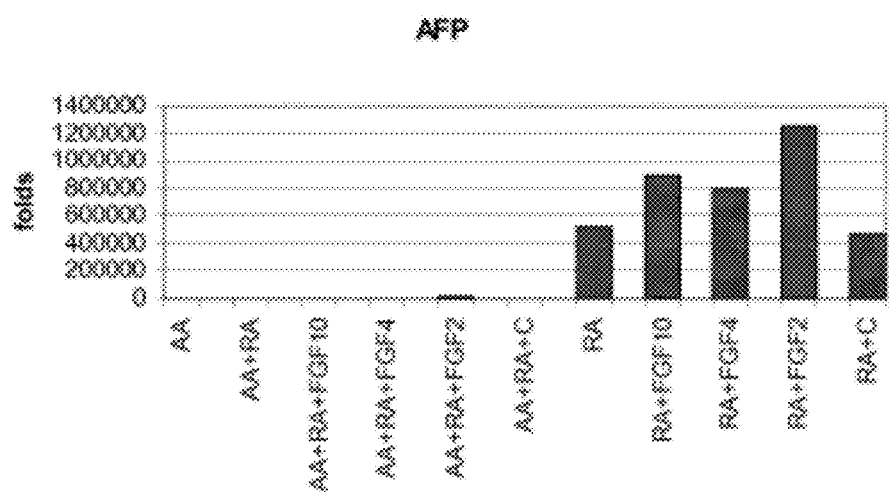
FIGS. 13A-13B shows the expression of hepatocyte markers in the human embryonic stem cell line H9 following application of a third differentiation protocol. Expression of the hepatocyte markers was assayed by PCR and normalized to expression levels in activin A treated human embryonic stem cells.

Cultures of human embryonic stem cells were maintained in undifferentiated culture conditions for 2-3 days according to the methods described in Example 1. After cells were 70-80% confluent, the medium was changed to DMEM/F12 with 2% FBS containing activin A at 100 ng/ml, and cells were cultured in the presence of activin A for seven days. After 7 days treatment with activin A, the cells were then treated for five days with the conditions shown in FIG. 13. After this time, the cells were harvested, and samples of mRNA were collected for analysis.

Figure 13B:
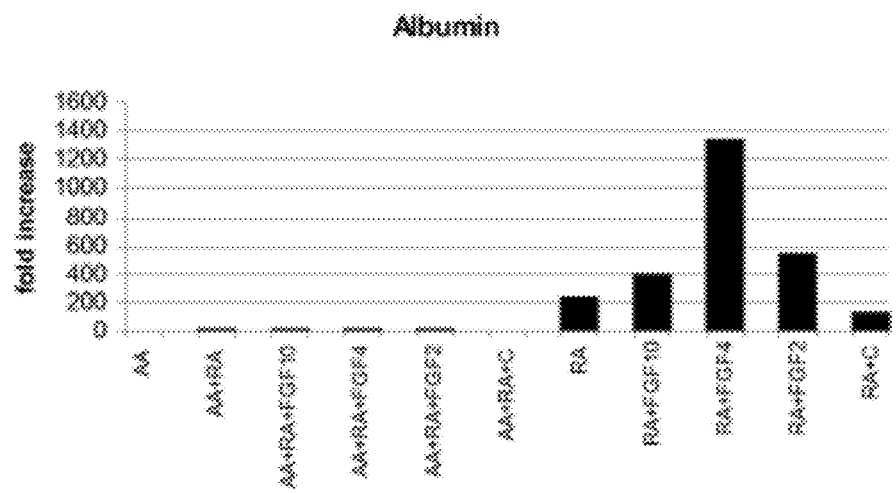

An increase in the expression of α-fetoprotein (AFP) and albumin was observed (FIG. 13A) for cells cultured in the absence of activin A. This was further increased by retinoic acid and FGF-4 (FIG. 13B). Taken together, these data suggest that cultures of human embryonic stem cells are capable of expressing hepatocyte markers following the treatment described above. Furthermore, human embryonic stem cells are capable of being differentiated into cells expressing markers that are characteristic of hepatocytes.

Example 8

Characterization of the H9 Human Embryonic Stem Cell Line

The quality of H9 cells was monitored over time by evaluating expression of several markers expressed by undifferentiated ES cells (Carpenter et al., 2001; Reubinoff et al., 2000; Thomson et al., 1998a). H9 cells exhibited reciprocal expression of stage-specific embryonic antigens (Table III). H9 cells play strong immunoreactivity for SSEA-3, SSEA-4, Tra-1-60, Tra-1-81, AP and CD9 antigens, all of which are characteristic of undifferentiated human embryonic stem cells.

Figure 14:
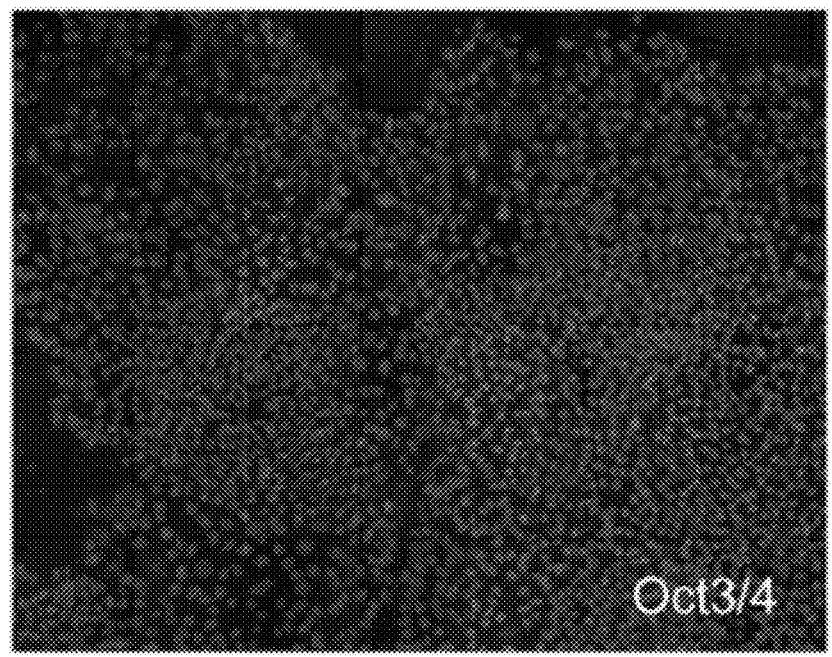
FIG. 14 shows the expression of markers of pluripotency in the human embryonic stem cell line H9. Expression of the markers of pluripotency was assayed by immunohistochemistry. The top panel shows Oct-4 expression. The bottom panel shows alkaline phosphatase expression.
Figure 14:
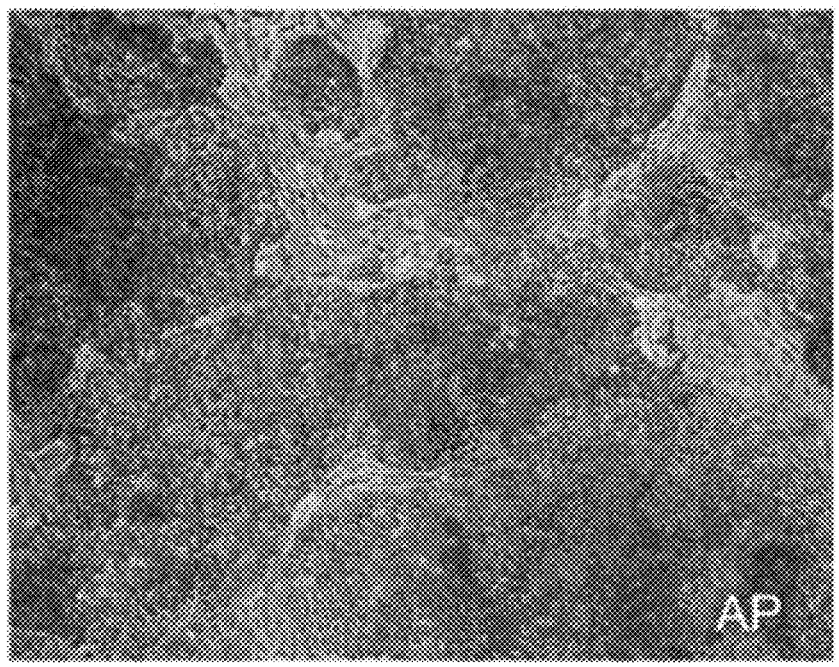

Real-Time PCR was performed to assess the expression of genes characteristic of embryonic stem cells, such as, for example, OCT3/4, SOX-2, UTF-1, REX-1, Cx43, Cx45, ABCG-2 and TERT, confirming that the cells grown in this example appeared similar to previously described undifferentiated embryonic stem cells (Table III). OCT3/4 protein expression and Alkaline Phosphatase activity (Chemicon) were confirmed by immunostaining. A majority of H9 cells were positive for OCT3/4 and AP (FIG. 14). Overall, these results demonstrate that the H9 cells used in this example were not significantly different in morphology, antigen immunostaining, or pluripotency marker expression when compared to reports from other laboratories.

Example 9

Fluorescence-Activated Cell Sorting (FACS) Analysis

Adhered cells were removed from culture plates by five-minute incubation with TrypLE™ Express solution (Invitrogen, CA). Released cells were resuspended in human embryonic stem cell culture medium and recovered by centrifugation, followed by washing and resuspending the cells in a staining buffer consisting of 2% BSA, 0.05% sodium azide in PBS (Sigma, MO). As appropriate, the cells were Fc-receptor blocked for 15 minutes using a 0.1% γ-globulin (Sigma) solution. Aliquots (approximately $10^5$ cells) were incubated with either phycoerythirin (PE) or allophycocyanin (APC) conjugated monoclonal antibodies (5 μl antibody per $10^6$ cells), as indicated in Table I, or with an unconjugated primary antibody. Controls included appropriate isotype matched antibodies, unstained cells, and cells stained only with secondary conjugated antibody. All incubations with antibodies were performed for 30 mins at 4° C. after which the cells were washed with the staining buffer. Samples that were stained with unconjugated primary antibodies were incubated for an additional 30 mins at 4° C. with secondary conjugated PE or—APC labeled antibodies. See Table I for a list of secondary antibodies used. Washed cells were pelleted and resuspended in the staining buffer, and the cell surface molecules were identified using a FACS Array (BD Biosciences) instrument, collecting at least 10,000 events.

Example 10

Immunocytochemistry

Cells seeded on 0.1% Matrigel (BD) coated dishes were fixed with 4% paraformaldheyde for 20 min at room temperature. Fixed cells were blocked for 1 h at room temperature with PBS/0.1% BSA/10% normal chick serum/0.5% Triton X-100 and then incubated overnight with primary antibodies in PBS/0.1% BSA/10% normal chick serum at 4° C. The list of primary antibodies and their working dilutions are shown in Table IB. After three washes in PBS/0.1% BSA, fluorescent secondary antibodies at a 1:100 dilution in PBS were incubated with cells for 1 h at room temperature to allow binding. Control samples included reactions where the primary antibody was omitted or where the primary antibody was replaced with corresponding matched negative control immunoglobulins at the same concentration as the primary antibodies. Stained samples were rinsed; a drop of PROLONG® (Invitrogen, CA) containing diamidino-2-phenylindole, dihydrochloride (DAPI) was added to each sample to counter-stain the nucleus and to function as an anti-fade reagent. Images were acquired using a Nikon Confocal Eclipse C-1 inverted microscope (Nikon, Japan) and a 10-60×objective.

Example 11

PCR Analysis of Undifferentiated Cells

RNA extraction, purification, and cDNA synthesis: RNA samples were purified by binding to a silica-gel membrane (Rneasy Mini Kit, Qiagen, CA) in the presence of an ethanol-containing, high-salt buffer followed by washing to remove contaminants. The RNA was further purified using a TURBO DNA-free kit (Ambion, INC), and high-quality RNA was then eluted in water. Yield and purity were assessed by A260 and A280 readings on a spectrophotometer. cDNA copies were made from purified RNA using an ABI (ABI, CA) high capacity cDNA archive kit.

Real-time PCR amplification and quantitative analysis: Unless otherwise stated, all reagents were purchased from Applied Biosystems. Real-time PCR reactions were performed using the ABI PRISM® 7900 Sequence Detection System. TAQMAN® UNIVERSAL PCR MASTER MIX® (ABI, CA) was used with 20 ng of reverse transcribed RNA in a total reaction volume of 20 µl. Each cDNA sample was run in duplicate to correct for pipetting errors. Primers and FAM-labeled TAQMAN® probes were used at concentrations of 200 nM. The level of expression for each target gene was normalized using a human glyceraldehyde-3-phosphate dehydrogenase (GAPDH) endogenous control previously developed by Applied Biosystem. Primer and probe sets are listed as follows: Oct3/4 (Hs00742896), SOX-2 (Hs00602736), UTF-1 (Hs00747497), Rex-1 (Hs00399279), Connexin 43 (Hs00748445), Connexin 45 (Hs00271416), ABCG2 (Hs00184979), Tert (Hs00162669), HNF 3β (Hs00232764), GATA-4 (Hs00171403), Mix11 (Hs00430824), Sox7 (Hs00846731), AFP (Hs00173490), Brachyury (Hs00610080), GSC (Hs00418279_m1), Pdx-1 (Hs00426216), PTF1a (Hs00603586), Ngn3 (Hs00360700), NeuroD1 (Hs00159598), Insulin (Hs00355773) and Glu2 (Hs00165775). Sox17 primers were designed using the PRIMERS program (ABI, CA) and were the following sequences: Sox17: TGGCGCAGCAGATACCA (SEQ ID NO: 1), AGCGCCTTCCACGACTTG (SEQ ID NO: 2) and CCAGCATCTTGCTCAACTCGGCG (SEQ ID NO: 3). After an initial incubation at 50° C. for 2 min followed by 95° C. for 10 min, samples were cycled 40 times in two stages—a denaturation step at 95° C. for 15 sec followed by an annealing/extension step at 60° C. for 1 min. Data analysis was carried out using GENEAMP®7000 Sequence Detection System software. For each primer/probe set, a Ct value was determined as the cycle number at which the fluorescence intensity reached a specific value in the middle of the exponential region of amplification. Relative gene expression levels were calculated using the comparative Ct method. Briefly, for each cDNA sample, the endogenous control Ct value was subtracted from the gene of interest Ct to give the delta Ct value (ΔCt). The normalized amount of target was calculated as 2-ΔCt, assuming amplification to be 100% efficiency. Final data were expressed relative to a calibrator sample.

Example 12

Karyotype Analysis

Figure 15:
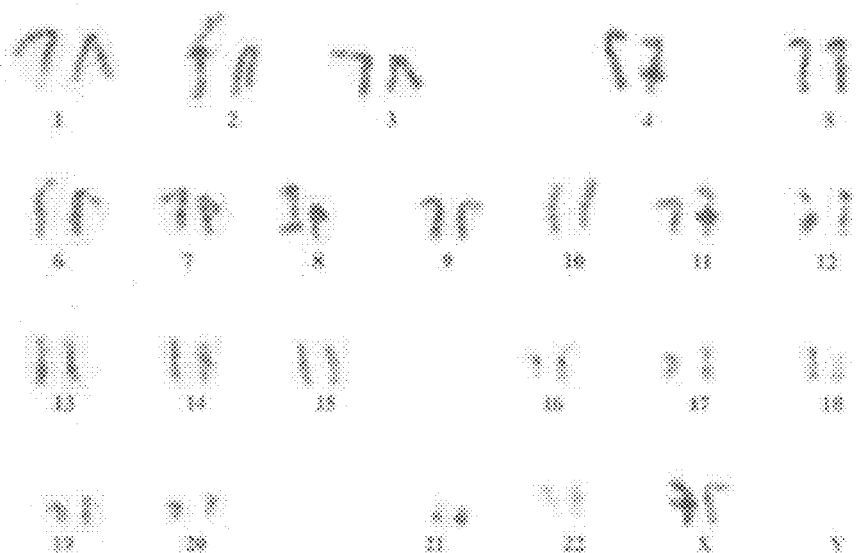
FIG. 15 shows the karyotype of the human embryonic cell line H9. The Karyotype was determined on cells at passage number P36 that were cultured on mouse embryonic fibroblast feeder cells.

The karyotype of H9 cells was determined by standard G-banding karyotype analysis. A total of 100 metaphase spreads were evaluated (Applied Genetics Laboratories, Inc.). No chromosome aberrations were found in 100 cells analyzed. Cytogenetic analysis showed that the cells had a normal number of autosomes and a modal chromosome number of 46. FIG. 15 depicts a typical karyotype obtained from the human embryonic stem cell line H9.

Example 13

Human Embryonic Stem Cell Culture on Tissue Culture Substrate Coated with Extracellular Matrix The human embryonic stem cell lines H1, H7, and H9 were obtained from WiCell Research Institute, Inc., (Madison, WI) and cultured according to instructions provided by the source institute. Briefly, cells were cultured on mouse embryonic fibroblast (MEF) feeder cells in ES cell medium consisting of DMEM/F12 (Invitrogen/GIBCO) supplemented with 20% knockout serum replacement, 100 nM MEM nonessential amino acids, 0.5 mM betamercaptoethanol, 2 mM L-glutamine with 4 ng/ml human basic fibroblast growth factor (bFGF). MEF cells, derived from E13 to 13.5 mouse embryos, were purchased from Charles River. MEF cells were expanded in DMEM medium supplemented with 10% FBS (Hyclone), 2 mM glutamine, and 100 mM MEM nonessential amino acids. Sub-confluent MEF cell cultures were treated with 10 µg/ml mitomycin C (Sigma, St. Louis, MO) for 3 h to arrest cell division, then trypsinized and plated at 2×10$^4$/cm$^2$ on 0.1% bovine gelatin coated dishes. MEF cells from passage two through four were used as feeder layers. Human embryonic stem cells plated on MEF cell feeder layers were cultured at 37° C. in an atmosphere of 5% $CO_2$ within a humidified tissue culture incubator. When confluent (approximately 5 to 7 days after plating), human embryonic stem cells were treated with 1 mg/ml collagenase type IV (Invitrogen/GIBCO) for 5 to 10 min and then gently scraped off the surface using a 5 ml glass pipette. Cells were centrifuged at 900 rpm for 5 min, and the pellet was resuspended and re-plated at a 1:3 to 1:4 ratio of cells on plates coated with a 1:30 dilution of growth factor reduced MATRIGEL™ (BD Biosciences). Cells were subsequently cultured in MEF-conditioned media supplemented with 8 ng/ml bFGF and collagenase passaged on MATRIGEL coated plates for at least five passages. The cells cultured on MATRIGEL™ were routinely passaged with collagenase IV (Invitrogen/GIBCO), Dispase (BD Biosciences) or Liberase enzyme (Roche, IN).

Example 14

Differentiation of Human Embryonic Stem Cells Cultured on Tissue Culture Substrate Coated with Extracellular Matrix to Definitive Endoderm Differentiation of embryonic stem cells to definitive endoderm was carried out as previously described in Nature Biotechnology 23, 1534-1541 (December 2005). Briefly, H9 cultures at approximately 60 to 70% confluency were exposed to DMEM:/F12 medium supplemented with 0.5% FBS and 100 ng/ml activin A for two days, followed by treatment with DMEM/F12 medium supplemented with 2% FBS and 100 ng/ml activin A (AA) for an additional three days. H9 cells were cultured on plates coated with growth factor reduced MATRIGEL at a 1:30 to 1:10 dilution or on regular MATRIGEL at a1:30 to 1:10 dilution The plates were coated with MATRIGEL for 1 hr at room temperature.

At day 5, the cultures were analyzed by FACS for CXCR4, E-cadherin, CD9, and N-cadherin expression and by real time PCR for SOX-17, SOX-7, Alphafetal protein (AFP), CXCR4, Brychyury (Bry), goosecoid (GSC), HNF-3 beta, and GATA4. AFP and SOX-7 are regarded as visceral endoderm markers, while GATA4, HNF-3 beta and SOX-17 represent definite endoderm markers, and GSC, Bry, and CXCR4 represent markers of primitive streak. FIG. 17 depicts the expression of CXCR4 by FACS. There was a significant increase in expression of CXCR4 by cells cultured on plates coated with MATRIGEL at a 1:10 dilution as compared to lower concentrations of MATRIGEL. Furthermore, growth factor reduced MATRIGEL was not as effective in formation of definitive endoderm cells as compared to regular MATRIGEL.

FIG. 18 shows the real-time PCR results verifying that cells cultured on plates coated with a 1:10 dilution of MATRIGEL showed a significant up regulation of definitive endoderm markers as compared to cells cultured on a 1:30 dilution of MATRIGEL.

Example 15

Microarray Analysis of Changes in Gene Expression in Human Embryonic Stem Cells Following Formation of Definitive Endoderm Total RNA was isolated from the following human embryonic stem cell cultures using an RNeasy mini kit (Qiagen): H9P83 cells cultured on MATRIGEL—coated plates and exposed to DMEM/F12 medium supplemented with 0.5% FBS and 100 ng/ml activin A for two days followed by treatment with DMEM/F12 medium supplemented with 2% FBS and 100 ng/ml Activin A (AA) for an additional three days; H9P44 cells cultured on MEFs and exposed to DMEM/F12 medium supplemented with 0.5% FBS and 100 ng/ml activin A for two days followed by treatment with DMEM/F12 medium supplemented with 2% FBS and 100 ng/ml activin A for an additional three days. Controls for each group included cells plated on MATRIGEL-coated dishes and cultured in MEF-conditioned medium or cells plated on MEFs and cultured in ES medium.

Sample preparation, hybridization, and image analysis were performed according to the Affymetrix Human Genome U133 Plus 2.0 Array. Following normalization and a log transformation, data analysis was performed using OmniViz® software (MA) and GENESIFTER (VizXLabs, WA). The variability within each treatment and among the different treatments was compared using the Pearson correlation coefficient. Variance in gene expression profiles between the different treatments along with the correlation coefficient between the lines are depicted in FIG. 19. Significant differences in gene expression between the samples were evaluated using analysis of variance and an F-test with adjusted P-value (Benjamini and Hochberg correction) of less-than or equal to 0.05. Only genes with a present call were included in the analysis. Table IV lists the genes that are differentially expressed with a difference at least 5-fold between the various samples. The normalized intensity value of the genes that are significantly expressed along with the standard error of the mean (SEM) for each gene are listed.

Example 16

Differentiation of Human Embryonic Stem Cells Cultured on Tissue Culture Substrate Coated with MATRIGEL to Definitive Endoderm Differentiation of embryonic stem cells to definitive endoderm was carried out as previously described in Nature Biotechnology 23, 1534-1541 (December 2005). Briefly, H9, H7, or H1 cells seeded on growth factor reduced MATRIGEL™ (1:30 dilution) cultures at approximately 60 to 70% confluency were exposed to DMEM/F12 medium supplemented with 0.5% FBS and 100 ng/ml activin A (R&D Systems, MN)) for two days followed by treatment with DMEM/F12 media supplemented with 2% FBS and 100 ng/ml activin A (AA) for an additional three days. In all subsequent examples unless otherwise noted, this treatment regimen will be referred to as the definite endoderm (DE) protocol.

In parallel, H9, H7, or H1 cells cultured on MEF feeders were also exposed to the same DE protocol outlined above.

At day 5, the cultures were analyzed by FACS for CXCR4, E-cadherin, CD9, CD99, and N-cadherin (CD56) expression and by real time PCR for SOX-17, SOX-7, Alpha-fetal protein (AFP), CXCR4, Brychyury (Bry), gooscecoid (GSC), HNF-3 beta, and GATA4. AFP and SOX-7 are regarded as visceral endoderm markers while GATA4, HNF-3beta and SOX-17 represent definite endoderm markers and GSC, Bry, and CXCR4 represent markers of primitive streak.

H-lines cultured on mouse feeders and exposed to the DE protocol resulted in a robust expression of DE markers and expression of CXCR4 by FACS (FIG. 20). There was also a significant decrease in expression of E-cadherin following treatment with the DE protocol. Lastly, the CXCR4+ population also stained positive for CD117. FIG. 21 shows a significant up regulation of definitive endoderm markers as compared to untreated H7 (FIG. 21A) and H9 cells (FIG. 21B).

Unlike H-lines cultured on MEF feeders, H-lines cultured on MATRIGEL™ (1:30 dilution) and treated with the definitive endoderm protocol failed to show robust expression of definitive endoderm markers. In particular, the expression of CXCR4 by FACS and by real-time PCR was significantly lower for cells cultured on MATRIGEL™ as compared to cells cultured on mouse embryonic fibroblasts. Expression of definitive endoderm markers follows a general response pattern with H1 being greater than H9, which is greater than H7 (FIGS. 22 and 23). From FIG. 22, H1 cells showed a significant increase in CXCR4 expression as compared to H7 and H9 lines. Note that in all cases, the expression of CXCR4 was lower for cells cultured on MATRIGEL™ (1:30 dilution) as compared to cells cultured on mouse embryonic fibroblasts. FIG. 23 (A-C) shows the real-time PCR results showing that there was modest increase in up regulation of definitive endoderm markers in H7 (FIG. 23A) and H9 (FIG. 23B) lines. However, H1 (FIG. 23C) line showed a more robust up regulation of definitive endoderm markers as compared to H7 and H9 lines.

Example 17

Differentiation of Human Embryonic Stem Cells Cultured on Tissue Culture Substrate Coated with MATRIGEL to Definitive Endoderm—Role of Wnt Ligands H7P44 and H9P46 embryonic stem cells were cultured on MATRIGEL™ (1:10 dilution) coated dishes and exposed to DMEM/F12 medium supplemented with 0.5% FBS, and 100 ng/ml activin A (R&D Systems, MN) for two days followed by treatment with DMEM/F12 media supplemented with 2% FBS and 100 ng/ml activin A (AA) for an additional three days. In some of the cultures 20 ng/ml Wnt-3a (Catalog #1324-WN-002, R&D Systems, MN), 20 ng/ml Wnt-5a (Catalog #654-WN-010, R&D Systems, MN), 25 ng/ml Wnt-7a (Catalog #3008-WN-025, R&D Systems, MN), or 25 ng/ml Wnt-5b (Catalog #3006-WN-025, R&D Systems, MN) was added throughout the five day treatment. FIG. 24 depicts phase contrast images of H9P46 definitive endoderm culture in the presence of high concentration of (a) AA or (b) AA+20 ng/ml Wnt-3a. FIG. 25 depicts the expression of CXCR4 by FACS at day 5 for H7P44, and H9P46 lines cultured on MATRIGEL™ (1:30 dilution) and exposed to the DE protocol+Wnt-3a (FIGS. 25A and 25D) and –Wnt-3a (FIGS. 25A and 25C). Presence of Wnt-3a in DE cultures resulted in robust expression of CXCR4 (CD184) as compared to DE cultures treated with low serum plus high concentration of AA. FIG. 26 displays the real-time PCR data for a) H7 and b) H9 cultures treated with low serum+AA+/–Wnt ligands. For both H lines, addition of WNT-3a resulted in significant up regulation of definitive endoderm markers. In contrast, Wnt 5a, Wnt-5b and Wnt-7a had minimal impact on expression of definitive endoderm markers.

Example 18

Differentiation of Human Embryonic Stem Cells Cultured on Tissue Culture Substrate Coated with MATRIGEL to Definitive Endoderm—Effective Dose of Wnt-3a H9P46 embryonic stem cells were cultured on MATRIGEL™ coated dishes (1:10 dilution) and exposed to DMEM/F12 medium supplemented with 0.5% FBS, 100 ng/ml Activin A (AA), and 10-50 ng/ml WNt-3a (R&D Systems, MN) for two days followed by treatment with DMEM/F12 media supplemented with 2% FBS, 100 ng/ml activin A (AA), and 10-50 ng/ml Wnt-3a for an additional three days. Control cultures were not treated with Wnt-3a. FIG. 27A depicts the expression of CXCR4 by FACS at day 5 in the absence of Wnt-3a, b) 10 ng/ml Wnt-3a, c) 20 ng/ml Wnt-3a and d) 50 ng/ml Wnt-3a. In the absence of Wnt-3a the expression of CXCR4 was very low. In contrast, addition of 10-50 ng/ml of Wnt-3a significantly increased the number of CXCR4 positive cells. Furthermore, addition of 10 ng/ml of Wnt-3a was as effective as addition of 50 ng/ml of Wnt-3a. Real-time PCR results (FIG. 28A) also confirm this finding.

In a separate study, H9p52 cells were plated on 1:30 low growth factor MATRIGEL™. For the first 2 days of the DE protocol a range of Wnt-3a doses was used: 10 ng/ml, 5 ng/ml and 1 ng/ml. FIG. 28B shows PCR analysis of the DE markers after 5 days of treatment. The number of cells at the end of the experiment is noted in FIG. 28C. This indicates that cells are proliferating when higher doses of Wnt-3a are used. Extension to 5 days of Wnt-3a treatment (5 D) had little effect on DE markers by PCR and did not significantly increase cell numbers (FIG. 28C). These data indicate that 10 ng/ml Wnt3a for 2 days is sufficient to reach optimal cell expansion and definitive endoderm differentiation.

Example 19

Differentiation of Human Embryonic Stem Cells Cultured on Tissue Culture Substrate Coated with MATRIGEL to Definitive Endoderm—Effect of GSK-3B Inhibitors In order to confirm that the effect of Wnt-3a was through the Wnt pathway, a GSK-3 inhibitor was used to activate the downstream targets of Wnt, such as beta catenin. H9P46-P48 embryonic stem cells were cultured on MATRIGEL™ coated dishes (1:10 dilution) and exposed to DMEM/F12 medium supplemented with 0.5% FBS, 100 ng/ml activin-A (AA), and 10-1000 nM GSK-3B inhibitor IX (Catalog #361550, Calbiochem, CA) for two days followed by treatment with DMEM/F12 media supplemented with 2% FBS, 100 ng/ml activin A (AA), and 0-1000 nM GSK-3B inhibitor IX (Catalog #361550, Calbiochem, CA) for an additional three days. Control cultures were treated with low serum plus high dose of activin A+/−Wnt-3a. FIG. 29A depicts the expression of CXCR4 by FACS at day 5 in the absence of Wnt-3a or GSK-3B inhibitor, b) +20 ng/ml Wnt-3a, c) +1000 nM GSK-3B inhibitor IX, d) +500 nM GSK-3B inhibitor IX, e) +100 nM GSK-3B inhibitor IX, f) +10 nM GSK-3B inhibitor IX, g) +100 nM GSK-3B inhibitor IX for days 1-2, and h) +10 nM GSK-3B inhibitor IX for days 1-2.

In the absence of Wnt-3a or at 10 nm GSK-3B inhibitor the expression of CXCR4 was very low. In contrast, addition of 20 ng/ml of Wnt-3a or 100-1000 nM GSK-3B inhibitor significantly increased the number of CXCR4 positive cells. Furthermore, addition of 100 nM GSK-3B inhibitor for days 1-2 was as effective as addition of 100 nM GSK-3B inhibitor for the entire five day period. FIG. 30 depicts the gene expression of definitive endoderm markers for (FIG. 30A) H9P48 cells and (FIG. 30B) H9P46 cells.

Figure 16:
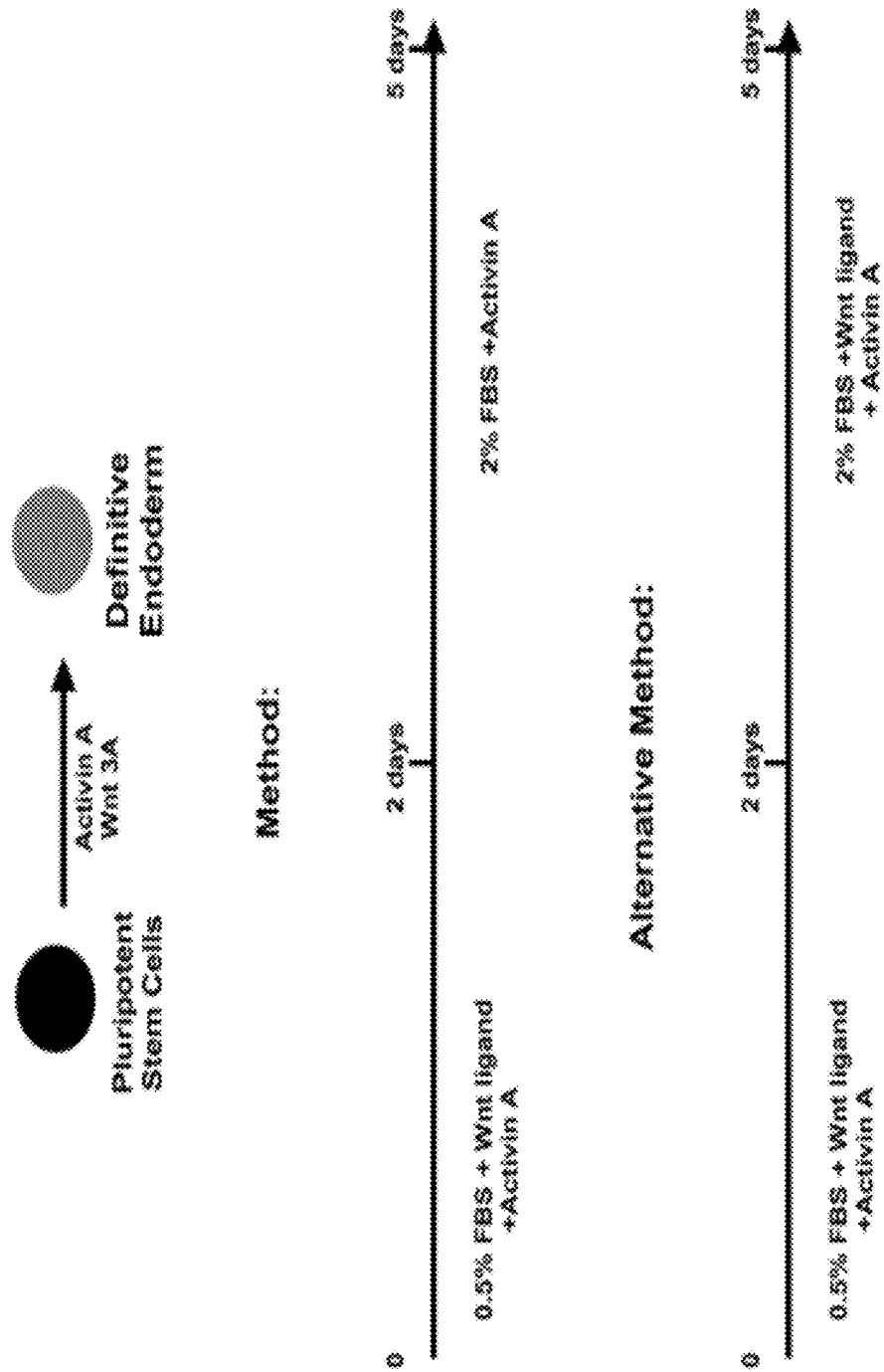
FIG. 16 depicts the outline of a differentiation protocol in this invention, where human embryonic stem cells are differentiated into definitive endoderm in a feeder free system.
Figure 17A:
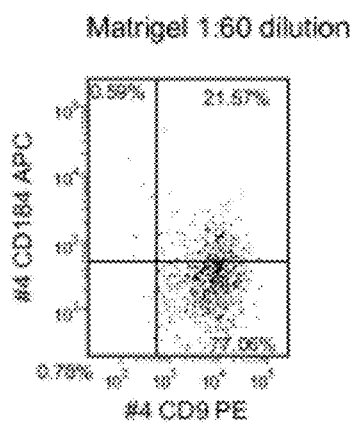
FIGS. 17A-17F depict the FACS profile of human embryonic stem cell line H9 at passage number 44, cultured on varying concentrations of MATRIGEL and exposed to (0.5-2%) low serum and high activin A (100 ng/ml) for 5 days. The expression of definite endoderm marker CXCR4
Figure 17B:
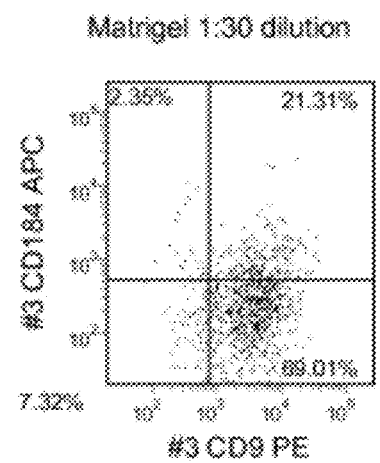
Figure 17C:
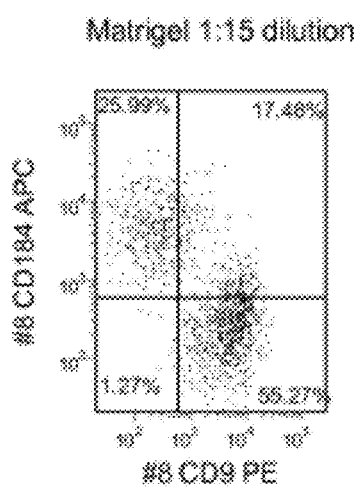
Figure 17D:
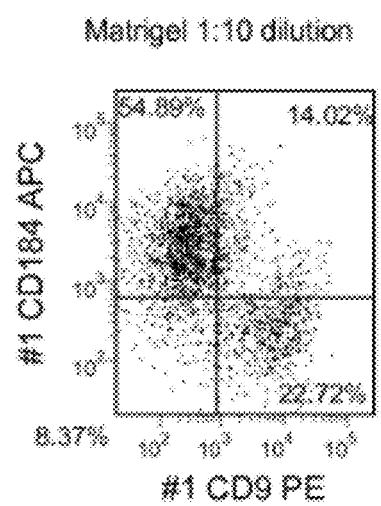
Figure 17E:
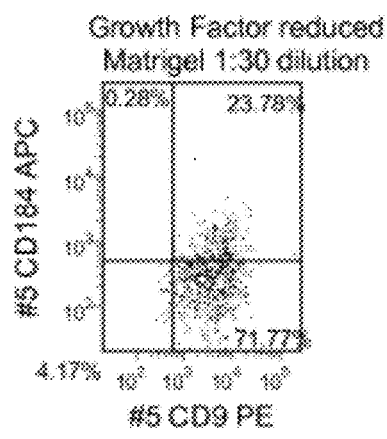
Figure 17F:
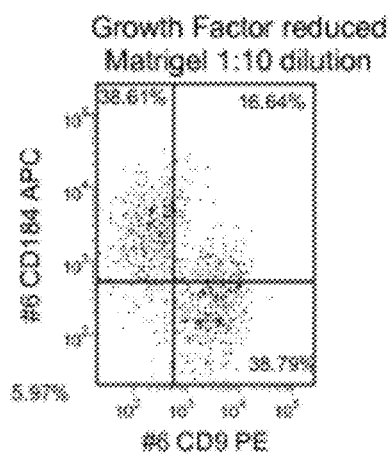

FIG. 16 depicts the outline of a differentiation protocol in this invention, where embryonic stem cells are differentiated into definitive endoderm in a feeder free system.

Example 20

Differentiation of Human Embryonic Stem Cells Cultured on Tissue Culture Substrate Coated with MATRIGEL to Definitive Endoderm—Effective Dose of Activin A in the Presence of a GSK-3B Inhibitor or Wnt-3a H9P49 and H1P46 embryonic stem cells were cultured on MATRIGEL™ coated dishes (1:10 dilution) and exposed to DMEM/F12 medium supplemented with 0.5% FBS, 10-100 ng/ml activin A (AA), and 100 nM GSK-3B inhibitor IX (Catalog #361550, Calbiochem, CA) or 20 ng/ml Wnt-3a for two days followed by treatment with DMEM/F12 media supplemented with 2% FBS, 10-100 ng/ml activin A (AA) for an additional three days. Control cultures were treated with low serum plus 100 ng/ml of activin A. FIG. 31 depicts the expression of CXCR4 by FACS for H9P49 and H1P46 at day 5 with a) 10 ng/ml activin A for all five days plus 20 ng/ml of Wnt-3A for the first two days, b) 100 ng/ml activin A for all five days plus 20 ng/ml of Wnt-3A for the first two days c) 100 ng/ml activin A for all five days plus 100 nM of GSK-3B inhibitor IX for the first two days d) 10 ng/ml activin A for all five days plus 100 nM of GSK-3B inhibitor IX for the first two days, e) 100 ng/ml activin A for all five days plus 20 ng/ml of Wnt-3A for the first two days, and f) 10 ng/ml activin A for all five days plus 20 ng/ml of Wnt-3A for the first two days. FIGS. 31A-31D are for H9P49 cells and FIGS. 31E-31F are for H1P46 cells. FIG. 32 depicts the gene expression of definitive endoderm markers for H9P49 cultures treated with 10, 50, or 100 ng/ml of activin A plus 20 ng/ml of Wnt-3a: FIG. 32A: expression of AFP, Bry, CXCR4, GSC, HNF-3B, and POU5F (Oct-4) and FIG. 32B: SOX-17 and GATA4. It appears that robust expression of definitive endoderm markers can be obtained by using 50 ng/ml of AA+20 ng/ml of Wnt-3A or 100 nM GSK-3B inhibitor IX. Lower doses of activin A lead to formation of extraembryonic endoderm.

Example 16

Differentiation of Human Embryonic Stem Cells Cultured on Tissue Culture Substrate Coated with MATRIGEL to Definitive Endoderm—Combination of Wnt-3a and GSK-3B Inhibitors H9P53 embryonic stem cells were cultured on MATRIGEL™ coated dishes (1:30 dilution) and exposed to DMEM/F12 medium supplemented with 0.5% FBS, 100 ng/ml activin A (AA), and 100 nM GSK-3B inhibitor IX (Catalog #361550, Calbiochem, CA) +/−20 ng/ml Wnt-3a for two days followed by treatment with DMEM/F12 media supplemented with 2% FBS, 10-100 ng/ml activin-A (AA) for an additional three days. In parallel, H9P53 cultures were treated with 25 ng/ml BMP-4 (Catalog #314-BP-010, R&D Systems, MN) +/−20 ng/ml Wnt-3A+/−100 ng/ml activin A. Control cultures were treated with low serum plus 100 ng/ml of activin A. FIG. 33 depicts the expression of CXCR4 by FACS at day 5 with a) 100 ng/ml activin A for all five days plus 20 ng/ml of Wnt-3A for the first two days and 25 ng/ml BMP-4 for days 3-5, b) 100 ng/ml activin A for all five days plus 20 ng/ml of Wnt-3A for the first two days c) 100 ng/ml activin A for all five days plus 100 nM of GSK-3B inhibitor IX for the first two days d) 20 ng/ml Wnt-3a+25 ng/ml BMP-4 for all five days, e) 100 ng/ml activin A for all five days plus 20 ng/ml of Wnt-3A+100 nm GSK-3B inhibitor IX for the first two days, and f) 100 ng/ml activin A+25 ng/ml BMP-4 for all five days. FIG. 34 depicts the gene expression of definitive endoderm markers, as determined by real-time PCR for cultures of the human embryonic stem cell line H1 at passage 46, treated with 10 or 100 ng/ml of activin A plus 20 ng/ml of Wnt-3a or 100 NM GSK-3B inhibitor: FIG. 34A: expression of AFP, Bry, CXCR4, GSC, and POU5F (Oct-4) and FIG. 34B: SOX-17, HNF-3B, and GATA4. Results are expressed as fold increase over untreated cells. FIG. 35 depicts the gene expression of definitive endoderm markers, as determined by real-time PCR for cultures of the human embryonic stem cell line H9 at passage 49, treated with 50 or 100 ng/ml of activin A plus 10 or 100 nM GSK-3B inhibitor: FIG. 35A: expression of AFP, Bry, CXCR4, GSC, HNF-3B, and POU5F (Oct-4) and FIG. 35B: SOX-17 and GATA4. Results are expressed as fold increase over untreated cells. FIG. 36 depicts the gene expression of definitive endoderm markers for H9P53 culture treated with combinations of activin A, Wnt-3a, GSK-3 inhibitor, and BMP-4: a) expression of AFP, Bry, CXCR4, GSC, HNF-3B, and SOX7 and b) SOX-17, HNF-3B and GATA4. Addition of BMP-4 to the DE protocol appears to induce formation of mesoderm marker BRY and combination of Wnt-3A and GSK-4B inhibitor did not lead to significant up regulation of definitive endoderm markers as compared to addition of each agent by itself in the presence of activin A.

Example 22

Differentiation of Human Embryonic Stem Cells Cultured on MEFs to Definitive Endoderm—Combination of Wnt-3a, Activin A, Wnt-5a, BMP-2, BMP-4, BMP-6, BMP-7, IL-4, and SDF-1 in Low Serum H9P44 cells were plated onto 6 well plates previously coated with mitomycin treated mouse embryonic fibroblasts (MEF). Cells were grown until 70 to 80% confluency in ES cell medium consisting of DMEM/F12 (Invitrogen/GIBCO) supplemented with 20% knockout serum replacement, 100 nM MEM nonessential amino acids, 0.5 mM beta-mercaptoethanol, 2 mM L-glutamine (all from Invitrogen/GIBCO) and 8 ng/ml human basic fibroblast growth factor (bFGF) (R&D Systems).

For DE formation, cells were treated in the presence or absence of Activin A (100 ng/ml) in addition to other growth factors detailed below. Growth factors were added to increasing concentration of FBS in a stepwise manner as indicated in the following regimen:
Day 0: 0% FBS in DMEM/F12
Day 1: 0.5% FBS in DMEM/F12
Day 2: 2% FBS in DMEM/F12.

Day 3: Cells were harvested for FACS analysis and RT-PCR.

All growth factors were purchased from R&D Systems, MN. A detailed description and concentration of growth factors for each treatment group is shown below.
 1. Control—No growth factor added
 2. Activin A (100 ng/ml)
 3. Activin A (100 ng/ml)+Wnt-3a (10 ng/ml)+Wnt5a (10 ng/ml)
 4. Activin A (100 ng/ml)+Wnt-3a (10 ng/ml)+Wnt5a (10 ng/ml)+BMP2 (100 ng/ml)
 5. Activin A (100 ng/ml)+BMP-4 (100 ng/ml)
 6. Activin A (100 ng/ml)+BMP-6 (100 ng/ml)
 7. Activin A (100 ng/ml)+BMP-7 (100 ng/ml)
 8. Activin A (100 ng/ml)+BMP-4 (100 ng/ml)+BMP-6 (100 ng/ml)+BMP-7 (100 ng/ml)
 9. IL-4 (10 ng/ml)
 10. SDF1a (20 ng/ml)
 11. Activin A (100 ng/ml)+IL-4 (10 ng/ml)+SDF1a (20 ng/ml)
 12. BMP2 (100 ng/ml)+BMP-4 (100 ng·ml)+BMP-6 (100 ng/ml)+BMP-7 (100 ng/ml)
 13. Activin A (100 ng/ml) BMP-2 (100 ng/ml)+BMP-4 (100 ng·ml)+BMP-6 (100 ng/ml)+BMP-7 (100 ng/ml)
 14. Activin A (100 ng/ml)+IL-4 (10 ng/ml)
 15. Activin A (100 ng/ml)+(SDF1a (20 ng/ml)
 16. Activin A (100 ng/ml)+Wnt-3a (10 ng/ml)+Wnt-5a (10 ng/ml)+Wnt-7a (10 ng/ml)
 17. Activin A (100 ng/ml)+IL-4 (10 ng/ml)+SDF1a (20 ng/ml)+BMP-4 (100 ng/ml)

Results:

Cells were harvested on Day 3 of DE protocol treatment. For analysis, an aliquot of treated cells was used for RNA preparation for RT-PCR and the rest of cells used for FACS analysis. The frequency (%) of CXCR4 is shown in FIG. 37. Addition of the above growth factor(s) did not enhance expression of CXCR4 above treatment with 100 ng/ml AA in low serum.

For RT-PCR analysis, cells were analyzed for expression of selected panel of definitive endoderm markers. Results shown were calibrated against cells grown in the base medium but not treated with Activin A or any of the other growth factors. In agreement with the FACS data, Table V shows that there was no significant up regulation of definitive endoderm markers by addition of growth factors, such as Wnt-3a to cultures treated with a high dose of activin A in low serum. This is in contrast to the previous examples showing a significant increase in DE markers for ES cells cultured on feeder-free conditions in the presence of activin A, WNT3A, and low serum.

Example 23

Differentiation of Human Embryonic Stem Cells Cultured on Tissue Culture Substrate Coated with MATRIGEL or Human Fibronectin to Definitive Endoderm H9P55 cells were grown and differentiated on human fibronectin or regular growth factor MATRIGEL™ (BD Biosciences). 1 ml of DMEM/F12 (Invitrogen/GIBCO) containing 1 ug/ml of human fibronectin (R&D systems, MN) was added to each well of 6 well tissue culture treated dish. Alternatively, regular growth factor MATRIGEL™ was diluted 1:10 in DMEM/F12 and 1 ml of diluted MATRIGEL™ was added to each well of 6 well tissue culture treated dish. Cells were passed with collagenase. After cells reached 80% confluency, there were treated as follows: 2 days 0.5% FBS containing 10 ng/ml mouse recombinant Wnt3a (R&D) and 100 ng/ml Activin A (R&D). This was followed by 3 days 2% FBS plus 100 ng/ml Activin A. FIGS. 38A-38B depict the expression of CXCR4 by embryonic stem cells cultured on fibronectin and MATRIGEL, respectively. Real-time PCR results (FIG. 39) confirm that formation of definitive endoderm was equivalent on fibronectin and MATRIGEL™ coated plates.

Example 24

Differentiation of Human Embryonic Stem Cells Cultured on Tissue Culture Substrate Coated with Varying Concentrations of MATRIGEL to Definitive Endoderm H9 cultures at approximately 60 to 70% confluency were exposed to DMEM/F12 medium supplemented with 0.5% FBS, 20 ng/ml Wnt-3a and 100 ng/ml activin A for two days followed by treatment with DMEM/F12 media supplemented with 2% FBS, 20 ng/ml Wnt-3a and 100 ng/ml activin A (AA) for an additional three days. H9 cells were cultured on plates coated with regular MATRIGEL at a 1:60 to 1:10 dilution. The plates were coated with MATRIGEL for 1 hr at room temperature.

Real time PCR results are shown in FIG. 40. Treatment of human embryonic stem cells with low serum, Activin A and Wnt-3a led to the expression of CXCR4, GATA4, Goosecoid, HNF-3beta, and SOX-17 genes, suggesting that the cells were differentiating to the definitive endoderm stage. However, it does not appear that the in the presence of Wnt-3a concentration of the MATRIGEL™ coating plays an important role in differentiation.

Example 25

Differentiation of Human Embryonic Stem Cells Cultured on Tissue Culture Substrate Coated with Extracellular Matrix and Subsequently Cultured on MEFs to Definitive Endoderm—Role of Wnt-3a Cells from the human embryonic stem cell line H9 cultured on MATRIGEL™ for at least five passages were seeded onto MEF feeders in ES media. When the cells reached 60 to 70% confluency they were exposed to DMEM/F12 medium supplemented with 0.5% FBS and 100 ng/ml activin A for two days followed by treatment with DMEM/F12 media supplemented with 2% FBS and 100 ng/ml activin A (AA) for an additional three days. Additional treatment groups include Wnt-3a at 20 ng/ml for all five days +10-100 ng/ml of activin A.

At day 3 and 5, the cultures were analyzed by real time PCR for SOX-17, SOX-7, Alpha-fetal protein (AFP), CXCR4, Brychyury (Bry), goosecoid (GSC), HNF-3 beta, GATA4, hTERT and Oct4. AFP and SOX-7 are regarded as visceral endoderm markers while GATA4, HNF-3beta and SOX-17 represent definite endoderm markers and GSC, Bry, and CXCR4 represent markers of primitive streak. hTERT and Oct-4 are markers for self renewal and pluripotency respectively. Real time-PCR results are shown in FIG. 41A-41D. FACS analysis was also performed at day 3 and 5. Expression levels of CXCR-4, and CD9 were analyzed and reported in FIG. 41E.

In the absence of Wnt-3a, AFP expression levels of cells cultured in 100 ng/ml Activin A are similar to those seen in untreated controls. However, with the addition of Wnt-3a to cells cultured in 100 ng/ml activin A, there is an increase in the expression of AFP that increases over time. When a lower concentration of Activin A is used, AFP expression is very high, regardless of the presence of Wnt3a (FIG. 41A). This suggests that a high concentration of Activin A is necessary to keep the cells from differentiating to extra-embryonic tissues.

By FACS analysis, CXCR4 positive cells ranged from 32-42% of the population in samples treated with a high concentration of Activin A but not treated with Wnt-3a as compared to 23-33% of the population in samples treated with a high concentration of Activin A and Wnt3a at day 3 (FIG. 41E). By day 5 of treatment, 28-32% of cells treated with a high concentration of activin A but not treated with Wnt-3a expressed CXCR4 as compared to 43-51% of cells treated with a high concentration of Activin A and Wnt-3a (FIG. 41F). In cells treated with a low concentration of Activin A, there were more CXCR4 positive cells in the treatment group without Wnt-3a (11 to 20%) as compared to the Wnt-3a treated group (3 to 4%) (FIG. 41G). Overall, Wnt-3a does not appear to play a significant role in differentiation of human embryonic stem cells, cultured on MEFs, to definitive endoderm. This suggests that the feeder layer is probably secreting sufficient Wnt-3a or analogous ligand to enhance activin A induced definitive—endoderm formation.

Example 26

Differentiation of Human Embryonic Stem Cells Cultured on Tissue Culture Substrate Coated with Extracellular Matrix to Definitive Endoderm Following Treatment with the Wnt Inhibitor DKK-1

To determine if the addition of Wnt-3a was causing the increase in differentiation, an inhibitor of Wnt-3 signaling was added to the cultures. H9 cultures at approximately 60 to 70% confluency were exposed to DMEM/F12 medium supplemented with 0.5% FBS, 20 ng/ml Wnt3a, 100 ng/ml Dikkopf-1 (DKK-1) and 100 ng/ml activin A for two days followed by treatment with DMEM/F12 media supplemented with 2% FBS and 100 ng/ml activin A (AA) for an additional three days. H9 cells were cultured on plates coated with Growth Factor Reduced MATRIGEL at a 1:30 dilution. The plates were coated with MATRIGEL for 1 hr at room temperature.

At day 5, the cultures were analyzed by real time PCR for SOX-17, SOX-7, Alpha-fetal protein (AFP), CXCR4, Brychyury (Bry), goosecoid (GSC), HNF-3 beta, GATA4, hTERT and Oct4. AFP and SOX-7 are regarded as visceral endoderm markers while GATA4, HNF-3beta and SOX-17 represent definite endoderm markers and GSC, Bry, and CXCR4 represent markers of primitive streak. hTERT and Oct-4 are markers for self renewal and pluripotency respectively. Results are shown in FIG. 42.

In the presence of Wnt-3a, cells express CXCR4, GATA4, HNF-3beta and SOX17, all markers of definitive endoderm. Markers of primitive streak formation such as goosecoid were also detected at levels higher than that detected in untreated controls. With the addition of DKK1, the expression level of the aforementioned differentiation markers dramatically decrease to levels similar to that of untreated cells.

Example 27

Immunofluoresence Staining of DE Markers for H9 Embryonic Stem Cells Cultured on Tissue Culture Substrate Coated with MATRIGEL and Differentiated in Low Serum Plus Activin A and ±Wnt-3a Day 5 DE cultures of H9 cells were stained according to Example 10 for SOX-17, HNF-3B, GATA-4, N-cadherin, and E-cadherin. All nuclei were counter stained with DAPI. 20 ng/ml Wnt-3a resulted in significantly larger number of nuclei stained positive for SOX-17, HNF-3beta. and GATA-4 as compared to cultures differentiated in the absence of Wnt-3a. Furthermore, addition of Wnt-3a resulted in significant loss of expression of e-cadherin and enhanced expression of N-cadherin (FIG. 43A and FIG. 43B).

Example 28

Microarray Analysis of Changes in Gene Expression in Embryonic Stem Cells Following Formation of Definitive Endoderm on MEFS or MATRIGEL Total RNA was isolated from the following embryonic stem cell cultures using an RNeasy mini kit (Qiagen): A) H9P33 cells cultured on MATRIGEL™—coated plates (1:30 dilution) and exposed to DMEM/F12 medium supplemented with 0.5% FBS and 100 ng/ml activin A for two days followed by treatment with DMEM/F12 medium supplemented with 2% FBS and 100 ng/ml activin A (AA) for an additional three days; B) H9P44 cells cultured on MEFs and exposed to DMEM/F12 medium supplemented with 0.5% FBS and 100 ng/ml Activin A for two days followed by treatment with DMEM/F12 medium supplemented with 2% FBS and 100 ng/ml Activin A for an additional three days, and C) H9P48 cells cultured on MATRIGEL™—coated plates (1:30 dilution) and exposed to DMEM/F12 medium supplemented with 0.5% FBS and 100 ng/ml activin A plus 20 ng/ml Wnt-3a for two days followed by treatment with DMEM/F12 medium supplemented with 2% FBS and 100 ng/ml Activin A (AA) for an additional three days. Controls for each group included cells plated on MATRIGEL-coated dishes and cultured in MEF-conditioned medium or cells plated on MEFs and cultured in ES medium. All groups contained three biological replicates and each biological replicate was repeated on two separate gene chips.

Sample preparation, hybridization, and image analysis were performed according to the Affymetrix Human Genome U133 Plus 2.0 Array. Following normalization and a log transformation, data analysis was performed using OmniViz® software (MA) and GENESIFTER (VizXLabs, WA). Significant differences in gene expression between the samples were evaluated using analysis of variance and an F-test with adjusted P-value (Benjamini and Hochberg correction) of less-than or equal to 0.05. Only genes with a present call in at least one group were included in the analysis. Table VI lists the mean normalized log transformed signal intensity of genes showing at least 5-fold difference between group A, group B, and group C along with the adjusted P-value for each gene.

Example 29

Differentiation of the SA002 ES Line Cultured on Tissue Culture Substrate Coated with MATRIGEL to Definitive Endoderm SA002 P38 cells (Cellartis, Sweden) previously cultured for at least three passages on MATRIGEL—coated plates (1:30 dilution) in MEF-CM supplemented with 8 ng/ml of bFGF were exposed to DMEM/F12 medium supplemented with 0.5% FBS, and 100 ng/ml activin A (R&D Systems, MN) +/−20 ng/ml of Wnt-3a or 100 nm GSK-3B IX inhibitor for two days followed by treatment with DMEM/F12 media supplemented with 2% FBS and 100 ng/ml activin A (AA) for an additional three days. Real time PCR results are shown in FIGS. 44A and 44B. Similar to H1, H7, and H9 lines, SA002 line also required addition of Wnt-3A for robust expression of DE markers. Expression of CXCR4 is depicted in FIG. 45: a) AA treatment b) AA+Wnt-3a c) AA+GSK-3B inhibitor.

Example 25

Differentiation of Human Embryonic Stem Cells Cultured on Tissue Culture Substrate Coated with Human Serum to Definitive Endoderm Cultures of the human embryonic stem cell line H1 at passage 55 were grown and differentiated on human serum (Sigma, #H1388, MO) coated plates. 0.5 ml of human serum was added to each well of 6 well tissue culture treated dish, incubated for 1 hr at room temperature, and aspirated before adding human embryonic stem cells. After cells reached 80% confluency, they were treated as follows: 2 days 0.5% FBS containing 10 ng/ml mouse recombinant Wnt3a (R&D) or 100 nM GSK-3B inhibitor IX (Catalog #361550, Calbiochem, CA) and 100 ng/ml Activin A (R&D). This was followed by 3 days 2% FBS plus 100 ng/ml Activin A. Cultures were then analyzed by real-time PCR (FIGS. 46A and 46B). Robust expression of definitive endoderm markers were noted for cells treated with activin A+GSK-3B inhibitor or Wnt-3A as compared to cells treated with activin A only. These findings parallel our findings for human embryonic stem cells cultured on MATRIGEL™ or human fibronectin coated plates.

Example 31

Differentiation of Human Embryonic Stem Cells Cultured on Tissue Culture Substrate Coated with MATRIGEL to Definitive Endoderm—Evaluation of Various GSK-3B Inhibitors The effectiveness of a number of commercially available GSK-3B inhibitors was evaluated in formation of DE from human embryonic stem cells. The following GSK-3B inhibitors were evaluated at 100 nM: GSK-3B inhibitor VIII (Catalog #361549, Calbiochem, CA), GSK-3B inhibitor IX (Catalog #361550, Calbiochem, CA), GSK-3B inhibitor XI (Catalog #361553, Calbiochem, CA), GSK-3B inhibitor XII (Catalog #361554, Calbiochem, CA). H1P54 ES cells were cultured on MATRIGEL™ coated dishes (1:30 dilution) and exposed to DMEM/F12 medium supplemented with 0.5% FBS, 100 ng/ml activin A (AA)+/−various GSK-3B inhibitors for two days followed by treatment with DMEM/F12 media supplemented with 2% FBS, 100 ng/ml activin A (AA) for an additional three days. Control cultures were treated with low serum plus high dose of AA. FIGS. 47A and 47B depict the gene expression of definitive endoderm markers at day 5. GSK-3B inhibitor IX and XI were both effective in inducing DE formation as compared to GSK-3B inhibitor VIII and XII.

Example 32

Formation of Pancreatic Endoderm by Human Embryonic Stem Cells Cultured Under Feeder-Free Conditions—Evaluation of Retinoic Acid Analogues H9P49 embryonic stem cells were cultured on MATRIGEL™ (1:30 dilution) coated dishes and exposed to DMEM/F12 medium supplemented with 0.5% FBS, 20 ng/ml Wnt-3a (Catalog #1324-WN-002, R&D Systems, MN), and 100 ng/ml activin A (R&D Systems, MN) for two days followed by treatment with DMEM/F12 media supplemented with 2% FBS and 100 ng/ml activin A (AA) for an additional three days. At day 5, cells were collected for evaluation by FACS and real-time PCR. As indicated in previous examples, this protocol resulted in robust up regulation of definitive endoderm markers, such as CXCR4 and SOX-17. The resulting definitive endoderm cells at day 5 were exposed to the following media conditions to induce pancreatic endoderm formation: culturing in DMEM/F12 media supplemented with 2% FBS and 1 µM all-trans retinoic acid (RA) (Catalog #R2625, Sigma, MO), or 0.1-10 µM AM-580 (4-[(5,6,7,8-Tetrahydro-5,5,8,8-tetramethyl-2-naphthalenyl)carboxamido]benzoic acid, Catalog #A8843, Sigma, MO), or 0.1-1 µM TTNPB (4-[(E)-2-(5,6,7,8-Tetrahydro-5,5,8,8-tetramethyl-2-naphthalenyl)-1-propenyl]benzoic acid Arotinoid acid, Catalog #T3757, Sigma, MO) for 3 days. AM-580 and TTNPB are retinoic acid analogs with affinity for retinoic acid receptors. RA treatment was followed by additional three day treatment in DMEM/F12 media supplemented with 2% FBS and 20-50 ng/ml bFGF (Catalog #F0291, Sigma, MO). Cultures were harvested and samples of mRNA were collected for analysis.

Gene expression analysis revealed that (FIGS. 48A-48D) addition of 1 µM RA followed by exposure to bFGF significantly upregulates pancreatic endoderm markers, such as PDX-1. Furthermore, this protocol resulted in robust expression of foregut endoderm markers, such as CDX-2 and AFP. At 1 µM concentration, addition of RA analogs resulted in equivalent pancreatic endoderm and foregut markers. However, addition of 1 µM RA analogs resulted in more robust expression of AFP as compared to all-trans retinoic acid. However, addition of 10 µM AM-580 suppressed AFP and CDX-2 expression while maintaining a high expression of PDX-1.

Example 34

The Effect of Wnt-3a Treatment on Cytokine Expression in Human Embryonic Stem Cells The effect that Wnt-3a treatment has on cytokine expression was analyzed using a protein array. Cells of the human embryonic stem cell line H9 were cultured according to the methods described in Example 15. At passage 54, cells were differentiated in the presence of 100 ng/ml Activin A+/−10 ng/ml Wnt3a for 2 days in 0.5% FBS DMEM/F12. Cells were subsequently cultured for an additional three days in 100 ng/ml Activin A and 2% FBS DMEM/F12. At the end of the 5th day, CXCR4 expression was determined by FACS for each treatment group. Cells treated with Activin A only had 1% of cells expressing CXCR4. Cells treated with Activin A and Wnt3a had 73% of cells positive for CXCR4 expression.

Cell lysates were prepared from cells of each treatment group, with a mammalian cell lysis kit (Sigma-Aldrich, MO). Conditioned media from each treatment group was collected and concentrated. Cytokine array analysis was completed using Cytokine Array panels provided by RayBiotech, GA (http://www.raybiotech.com/). Table VII lists cytokine, growth factor, and receptor expression following normalization of the data and background subtraction. For each panel, positive and negative controls are also included. The data shown are two independent samples per cell treatment group (1,2).

Noticeable upregulation of Angiogenin, IGFBP-1 and EGF are seen in the Wnt-3a treated cell conditioned media. Numerous proteins are upregulated in the Wnt-3a treated cell lysates including IGFBP-1, TGFbeta-1 and TGFbeta-3. These upregulated proteins can be added back into the differentiation media to replace or enhance Wnt-3a effects on definitive endoderm formation.

Example 35

Differentiation of Human Embryonic Stem Cells Cultured on Tissue Culture Substrate Coated with MATRIGEL to Definitive Endoderm: Role of Wnt1

H1P55 ES cells were cultured on MATRIGEL™ (1:30 dilution) coated dishes and exposed to DMEM/F12 medium supplemented with 0.5% FBS, and 100 ng/ml activin A+/−10-20 ng/ml of WNT-1 (PeproTech, NJ, Catalogue #120-17) for two days followed by treatment with DMEM/F12 media supplemented with 2% FBS, 100 ng/ml activin A (AA) and +/−10 or 20 ng/ml of WNT-1 for an additional three days. The following combinations of WNT1+AA were tested:

a) 20 ng/ml of WNT1+100 ng/ml AA in 0.5% FBS+DM-F12 for days 1-2 followed by 2% FBS+DM-F12+100 ng/ml AA for day three, b) 20 ng/ml of WNT1+100 ng/ml AA in 0.5% FBS+DM-F12 for days 1-2 followed by 2% FBS+DM-F12+100 ng/ml AA for days 3-5, c) 10 ng/ml of WNT1+100 ng/ml AA in 0.5% FBS+DM-F12 for days 1-2 followed by 2% FBS+DMF12+100 ng/ml AA for day three, d) 10 ng/ml of WNT1+100 ng/ml AA in 0.5% FBS+DM-F12 for days 1-2 followed by 2% FBS+DM-F12+100 ng/ml AA for days 3-5, e) 20 ng/ml of WNT1+100 ng/ml AA in 0.5% FBS+DM-F12 for days 1-2 followed by 2% FBS+DM-F12+100 ng/ml AA+20 ng/ml of WNT1 for day three, f) 20 ng/ml of WNT1+100 ng/ml AA in 0.5% FBS+DM-F12 for days 1-2 followed by 2% FBS+DM-F12+100 ng/ml AA+20 ng/ml of WNT1 for days 3-5. FIGS. 49A and 49B displays the real-time PCR data for definitive endoderm markers following treatment of the H1 cells with low serum, AA and Wnt-1. Addition of 20 ng/ml of Wnt1 in the presence of 100 ng/ml of AA resulted in significant up regulation of definitive endoderm markers (Bry, CXCR4, GSC, SOX17, HNF-3B, and GATA-4).

Example 36

The Effect of Glucose on Pancreatic Endocrine Differentiation

The efficiency of differentiating pancreatic endoderm cells into pancreatic endocrine cells depends on many factors, including, for example, the choice of basal media, or the concentration of glucose. The effect of glucose concentration on the differentiation of pancreatic endoderm cells, derived from embryonic stem cells, into pancreatic endocrine cells was examined.

Alteration of glucose concentration by changing the basal media: Cultures of undifferentiated human embryonic stem cells (H1 and H9) were cultured according to the methods described in Example 1, prior to differentiation into pancreatic endoderm cells. Embryonic stem cells were differentiated into pancreatic endoderm cells by culturing the embryonic stem cells in RPMI containing activin A at 100 ng/ml in the absence of serum for one day. After this time, the cells were cultured in RPMI containing activin A at 100 ng/ml and 0.2% FBS for an additional two days. Following this treatment, the medium was replaced with RPMI containing 2% FBS, FGF10 (50 ng/ml) and KAAD-cyclopamine (250 nM). Cells were cultured in this medium for four days. After this time, the medium was replaced with medium supplemented with 1× B27, containing all-trans retinoic acid (2 µM), FGF10 (50 ng/ml) and KAAD-cyclopamine (0.25 µM) for four days to induce the formation of pancreatic endoderm cells. The yield of pancreatic endoderm cells was not significantly different in cultures treated with low-glucose DMEM or DMEM/F12.

Pancreatic endoderm cells were differentiated into pancreatic endocrine cells by treating the cells with Exendin 4 and HGF. Exendin 4 (50 ng/ml) and HGF (50 ng/ml) were added for ten days in either low-glucose DMEM or DMEM/F12 for 10 days. Both media were supplemented with 1× B27. Cultures were harvested and samples of mRNA were collected for analysis. Samples were normalized to pancreatic endoderm obtained according to the methods disclosed in Nature Biotechnology 24, 1392-1401 (2006).

Insulin expression was analyzed by real-time PCR. As shown in FIGS. 50A and 50B, both insulin and glucagon gene expression were strongly increased in cells treated DMEM/F12, compared to cells treated in DMEM-low glucose. Insulin expression was also analyzed by immunohistochemistry (FIG. 51). Treatment in DMEM/F12 resulted in a larger percentage of insulin positive cells, compared to DMEM-low glucose (FIGS. 51A and 51B). Insulin positive cells were also positive for PDX-1 (FIG. 51C).

Figure 52A:
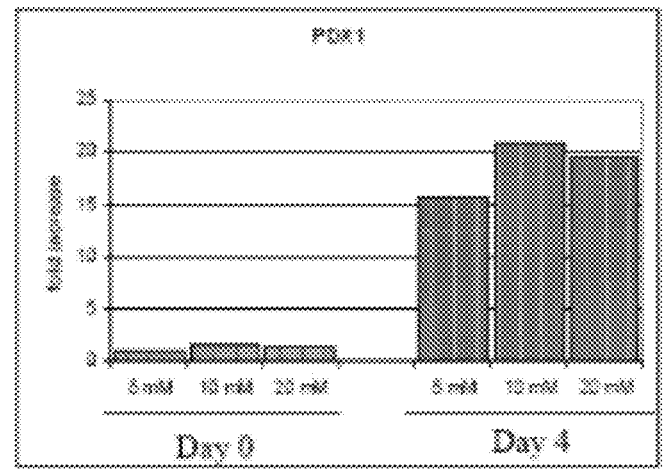
Figure 52B:
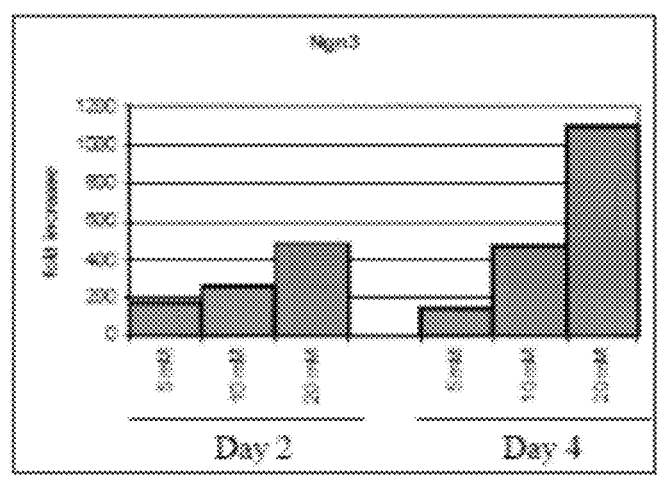
Figure 52C:
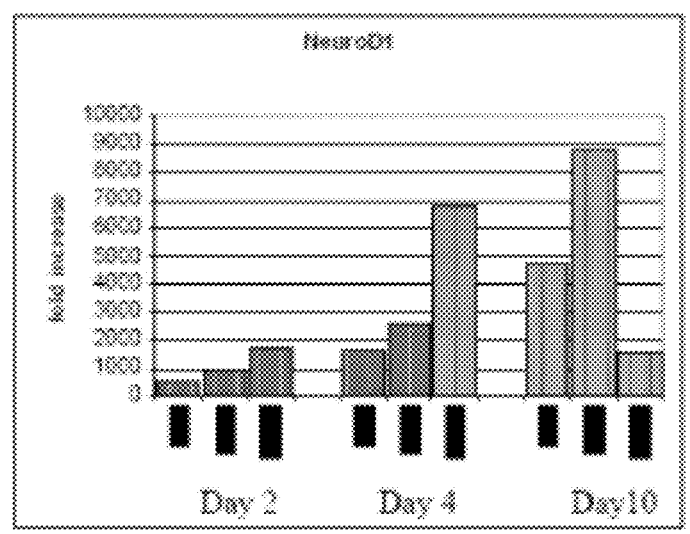

Alteration of glucose concentration: Cultures of undifferentiated human embryonic stem cells (H1 and H9) were cultured according to the methods described in Example 1, prior to differentiation into pancreatic endoderm cells. Embryonic stem cells were differentiated into pancreatic endoderm cells by culturing the embryonic stem cells in RPMI containing activin A at 100 ng/ml in the absence of serum for one day. After this time, the cells were cultured in RPMI containing activin A at 100 ng/ml and 0.2% FBS for an additional two days. Following this treatment, the medium was replaced with RPMI containing 2% FBS, FGF10 (50 ng/ml) and KAAD-cyclopamine (250 nM). Cells were cultured in this medium for four days. After this time, the medium was replaced with CMRL supplemented with 1× B27, containing all trans retinoic acid (2 µM), FGF10 (50 ng/ml) and KAAD-cyclopamine (0.25 µM) for four days to induce the formation of pancreatic endoderm cells. The media was supplemented with 5, 10 or 20 mM glucose. The yield of pancreatic endoderm cells was not significantly different in cultures derived from H9 embryonic stem cells treated with 5, 10 or 20 mM glucose (FIG. 52A).

Pancreatic endoderm cells were differentiated into pancreatic endocrine cells by treating the cells with CMRL supplemented with 1× B27, Exendin 4 (50 ng/ml) and HGF (50 ng/ml) for two, four or 10 days in 5, 10 or 20 mM glucose. Cultures were harvested and samples of mRNA were collected for analysis. Samples were normalized to pancreatic endoderm obtained according to the methods disclosed in Nature Biotechnology 24, 1392-1401 (2006).

Figure 52D:
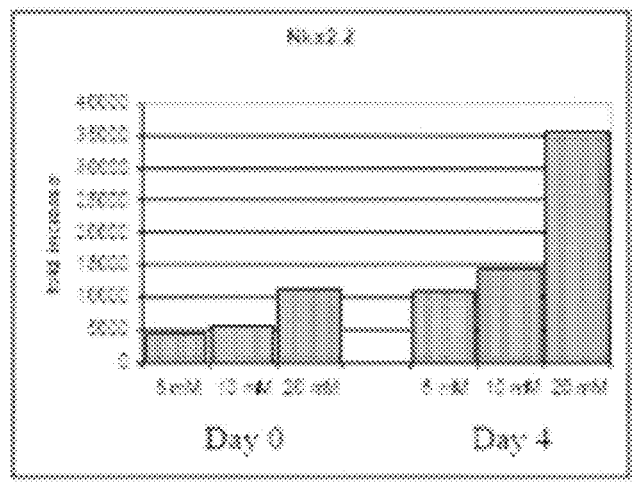
Figure 52E:
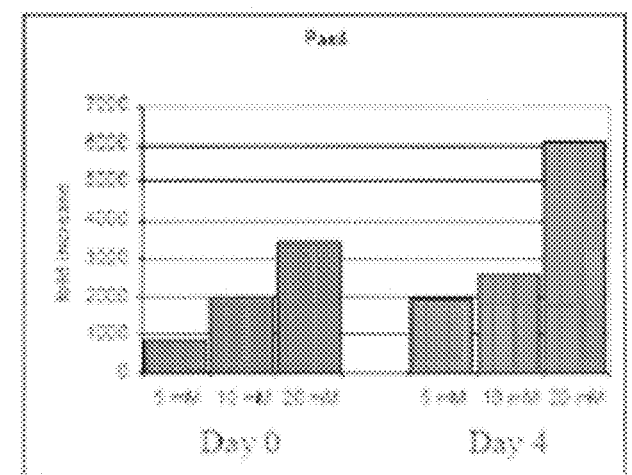
Figure 52F:
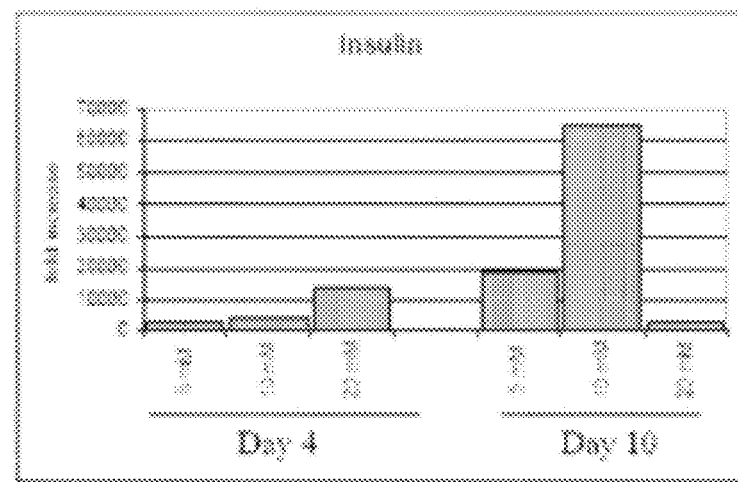
Figure 52G:
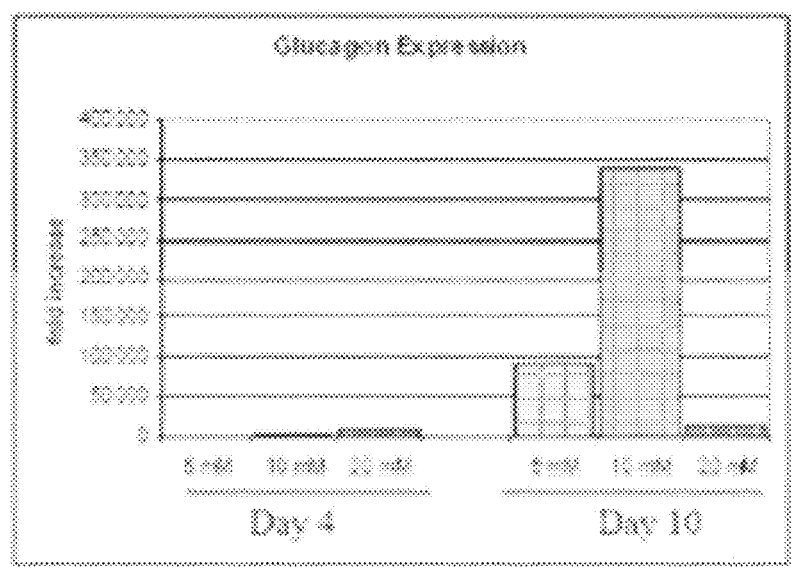

FIGS. 52B-52G show the effect of glucose on the expression of Ngn-3, NeuroD-1, Nkx2.2, Pax-4, insulin and glucagon, in cells derived from the human embryonic stem cell line H9. Ngn3 is the first transcription factor involved in determining the pancreatic endocrine fate and NeuroD1 is a direct target of Ngn3. Glucose stimulates a does-dependent increase in both Ngn3 and NeuroD1 mRNA levels. Another two critical pancreatic markers, Nkx2.2 and Pax4, also showed the similar expression pattern (FIGS. 52D and 52E). Optimal insulin and glucagon expression was observed in cells treated with 10 mM glucose for 10 days (FIGS. 52F and 52G).

Similar results for Ngn-3, NeuroD-1, Nkx2.2, Pax-4 were observed in cultures derived from the human embryonic stem cell line H1 (Table VIII). However, optimal insulin and synaptophysin expression was observed in cells treated with 20 mM glucose for 10 days (Table VIII).

C-peptide release from insulin expressing cells formed by the methods of the present invention: Glucose-mediated c-peptide release was monitored in insulin positive cells derived from H1 cells, that were treated in 2, 10 or 20 mM glucose. To evoke c-peptide release, cells were first incubated with Krebs-Ringer solution with bicarbonate and HEPES (KRBH; 129 mM NaCl, 4.8 mM KCl, 2.5 mM $CaCl_2$, 1.2 mM $KH_2PO_4$, 1.2 mM $MgSO_4$, 5 mM $NaHCO_3$, 10 mM HEPES, 0.1% BSA), for 1 hr. The medium was discarded and replaced with Krebs-Ringer solution containing 2 mM D-glucose. Cells were stimulated with either 20 mM glucose or 0.5 mM IBMX for 1 hr (all purchased from Sigma). The fold stimulation was calculated for each culture by dividing the C-peptide concentration in the simulation supernatant by the C-peptide concentration in the basal supernatant.

BMX stimulated C-peptide release 1.2 to 3 fold (FIG. 53). 20 mM glucose did not stimulate C-peptide release. There was no significant difference in C-peptide secretion observed between insulin positive cells formed in 2, 10 and 20 mM glucose.

Taken together, our data suggest that glucose induces the dose-dependant up regulation of the endocrine markers, Ngn3 and NeuroD1, suggesting that glucose induces the dose-dependent differentiation of human embryonic cells into pancreatic endocrine cells. The expression of insulin is also regulated by glucose in a dose-dependant manner.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method for generating human pancreatic endocrine cells, comprising:
   differentiating human pluripotent stem cells into definitive endoderm cells by culturing the pluripotent cells in a medium supplemented with activin A, then removing the medium supplemented with activin A;
   differentiating the definitive endoderm cells into pancreatic endoderm cells by culturing the definitive endoderm cells in a medium supplemented with retinoic acid and fibroblast growth factor-2 (FGF-2), then removing the medium supplemented with retinoic acid and FGF-2; and
   differentiating the pancreatic endoderm cells into pancreatic endocrine cells by culturing the pancreatic endoderm cells in a medium supplemented with 1S-Benzyl-4R41-(1S-carbamoyl-2-phenethylcarbamoyl)-1S-3-methylbutylcarbamoyl]-2R-hydrozy-5-phenylpentyl] carbamic Acid tert-butyl Ester (L-685,458), thereby generating the pancreatic endocrine cells, wherein FGF-2 is used at a concentration of about 20 ng/ml to about 50 ng/ml.

2. The method of claim 1, wherein the pancreatic endoderm cells are cultured with the L-685,458 for about 1 to about 5 days.

3. The method of claim 1, wherein the pancreatic endoderm cells are cultured with the L-685,458 for about 3 to about 5 days.

4. The method of claim 1, wherein the pancreatic endoderm cells are cultured with the L-685,458 for about 3 days.

5. The method of claim 1, wherein the pancreatic endoderm cells are cultured with the L-685,458 for about 5 days.

6. The method of claim 1, wherein the L-685,458 is used at a concentration of about 0.1 μM to about 100 μM.

7. The method of claim 6, wherein the L-685,458 is used at a concentration of about 10 μM.

8. The method of claim 6, wherein the L-685,458 is used at a concentration of about 20 μM.

9. The method of claim 6, wherein the L-685,458 is used at a concentration of about 90 μM.

10. The method of claim 1, wherein the FGF-2 is used at a concentration of about 50 ng/ml.

11. The method of claim 1, wherein the retinoic acid is used at a concentration of about 1 μM.

12. The method of claim 4, wherein the definitive endoderm cells are cultured with the retinoic acid and the FGF-2 for about 6 days.

13. The method of claim 12, wherein the L-685,458 is used at a concentration of about 10 μM, the FGF-2 is used at a concentration of about 50 ng/ml, and the retinoic acid is used at a concentration of about 1 μM.

14. The method of claim 1, wherein the medium supplemented with retinoic acid and FGF-2 does not comprise activin A.

* * * * *